United States Patent
Schwarz et al.

(10) Patent No.: US 7,932,283 B2
(45) Date of Patent: Apr. 26, 2011

(54) FUNGICIDE N-CYCLOPROPYL-SULFONYLAMIDE DERIVATIVES

(75) Inventors: Hans-Georg Schwarz, Langelfeld (DE); Sandra Gassmann, Thannenkirch (FR); Karl-Heinz Kuck, Langelfeld (DE); Peter Dahmen, Neuss (DE); Ulrike Wachendorff-Neumann, Neuwied (DE); Stéphane Carbonne, Lyons (FR); Stéphanie Gary, Lyons (FR); Christopher Steele, Lyons (FR); Alain Villier, Collonges au Mont d'Or (FR); Jean-Pierre Vors, Sainte Foy les Lyon (FR)

(73) Assignee: Bayer Cropscience AG (DE)

( * ) Notice: Subject to any disclaimer, the term of this patent is extended or adjusted under 35 U.S.C. 154(b) by 143 days.

(21) Appl. No.: 12/225,968

(22) PCT Filed: Apr. 5, 2007

(86) PCT No.: PCT/EP2007/053387
§ 371 (c)(1),
(2), (4) Date: Oct. 3, 2008

(87) PCT Pub. No.: WO2007/113327
PCT Pub. Date: Oct. 11, 2007

(65) Prior Publication Data
US 2009/0137611 A1 May 28, 2009

(30) Foreign Application Priority Data
Apr. 5, 2006 (EP) ..................................... 06356039

(51) Int. Cl.
*A01N 43/56* (2006.01)

(52) U.S. Cl. ........ 514/406; 514/443; 514/444; 514/445; 548/374.1; 548/375.1; 548/365.7; 548/136; 540/215; 549/50; 549/70

(58) Field of Classification Search .................. 514/406, 514/443, 445, 444; 548/374.1, 375.1, 365.7, 548/136; 540/215; 549/50, 70
See application file for complete search history.

(56) References Cited

U.S. PATENT DOCUMENTS 6,706,748 B2 * 3/2004 Kitagawa et al. ............. 514/372

FOREIGN PATENT DOCUMENTS

| JP | 08-277277 | 10/1996 |
| JP | 08277277 | 10/1996 |
| JP | 08 277277 A | 2/1997 |
| JP | 09-031069 | 2/1997 |
| WO | WO 01/77090 | 10/2001 |

* cited by examiner

*Primary Examiner* — Yong Chu
*Assistant Examiner* — Valerie Rodriguez-Garcia
(74) *Attorney, Agent, or Firm* — Ostrolenk Faber LLP

(57) ABSTRACT

The present invention relates to N-cyclopropyl-sulfonylamide derivatives of formula (I) wherein the substituents are cyclic groups, their process of preparation, their use as fungicide active agents, particularly in the form of fungicide compositions, and methods for the control of phytopathogenic fungi, notably of plants, using these compounds or compositions:

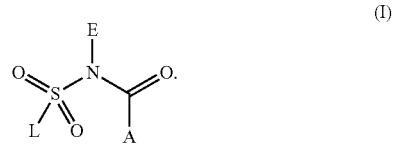

(I)

21 Claims, No Drawings

FUNGICIDE N-CYCLOPROPYL-SULFONYLAMIDE DERIVATIVES

CROSS REFERENCE TO RELATED APPLICATION(S)

The present application is a 35 U.S.C. §371 national phase conversion of International Application No. PCT/EP2007/053887 filed Apr. 5, 2007, which claims priority of European Application No. 06356039.5 filed Apr. 5, 2006.

The present invention relates to N-cyclopropyl-sulfonylamide derivatives, their process of preparation, their use as fungicide active agents, particularly in the form of fungicide compositions, and methods for the control of phytopathogenic fungi, notably of plants, using these compounds or compositions.

In international patent application WO-01/77090, there are disclosed isothiazole derivatives of the following formula:

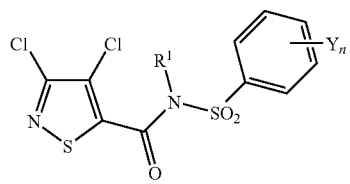

wherein $R^1$ may represent a cycloalkyl group. Preferred cycloalkyl groups are $C_{5-6}$-cycloalkyl groups, in particular cyclohexyl groups. Two examples are disclosed with such cyclohexyl groups. These two examples numbered Ia-88 and Ia-101 show insufficient or no activity on plant pathogen fungi.

In Japanese patent application JP-931069, there are disclosed 8 particular (2-bromo or 2-chloro)-(4-methyl or 4-ethyl)-1,3-thiazol-5-yl-(4-chloro-phenyl or phenyl)-N-cyclopropyl-sulfonylamide derivatives that are excluded from the scope of the present invention. Indeed, these 8 compounds have not been prepared and no activity is reported.

It is always of high-interest in agriculture to use novel pesticide compounds in order to avoid or to control the development of resistant strains to the active ingredients. It is also of high-interest to use novel compounds being more active than those already known, with the aim of decreasing the amounts of active compound to be used, whilst at the same time maintaining an effectiveness at least equivalent to the already known compounds.

We have now found a new family of compounds which possess the above mentioned effects or advantages.

Accordingly, the present invention provides N-cyclopropyl-sulfonylamide derivatives of formula (I):

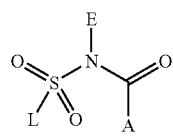

(I)

wherein:

A represents a carbon linked, substituted or non substituted, 5-, 6- or 7-membered, aromatic or non aromatic heterocycle comprising up to three heteroatoms which can be the same or different;

E represents a substituted or non substituted cyclopropyl

L represents a substituted or non substituted phenyl or a substituted or non substituted 5-, 6- or 7-membered aromatic or non aromatic heterocycle comprising up to three heteroatoms which can be the same or different as well as salts, N-oxydes, metallic complexes, metalloidic complexes and optically active isomers thereof; provided that when E represents a non-substituted cyclopropyl, A and L cannot represent simultaneously respectively a 2-bromo-4-methyl-1,3-thiazol-5-yl and a 4-chlorophenyl;

a 2-chloro-4-methyl-1,3-thiazol-5-yl and a 4-chlorophenyl;

a 2-bromo-4-ethyl-1,3-thiazol-5-yl and a 4-chloro-phenyl;

a 2-chloro-4-ethyl-1,3-thiazol-5-yl and a 4-chloro-phenyl;

a 2-bromo-4-methyl-1,3-thiazol-5-yl and a phenyl;
a 2-chloro-4-methyl-1,3-thiazol-5-yl and a phenyl;
a 2-bromo-4-ethyl-1,3-thiazol-5-yl and a phenyl;
a 2-chloro-4-ethyl-1,3-thiazol-5-yl and a phenyl.

Any of the compounds according to the invention can exist in one or more optical or chiral isomer forms depending on the number of asymmetric centres in the compound. The invention thus relates equally to all the optical isomers and to their racemic or scalemic mixtures (the term "scalemic" denotes a mixture of enantiomers in different proportions), and to the mixtures of all the possible stereoisomers, in all proportions. The diastereoisomers and/or the optical isomers can be separated according to the methods which are known per se by the man ordinary skilled in the art.

Any of the compounds according to the invention can also exist in one or more geometric isomer forms depending on the number of double bonds in the compound. The invention thus relates equally to all geometric isomers and to all possible mixtures, in all proportions. The geometric isomers can be separated according to general methods, which are known per se by the man ordinary skilled in the art.

For the compounds according to the invention, halogen atom means either one of fluorine, bromine, chlorine or iodine and heteroatom can be nitrogen, oxygen or sulphur.

For the compounds of formula (I) according to the invention, E can be substituted by up to five groups Z which can be the same or different and are selected in the list consisting of halogen atoms; $C_1$-$C_5$-alkyl; $C_1$-$C_5$-halogenoalkyl comprising up to 5 halogen atoms which can be the same or different; phenyl substituted by up to 5 halogen atoms which can be the same or different and $C_1$-$C_5$-alkoxycarbonyl.

Preferred compounds of formula (I) according to the invention are those wherein E represents a non-substituted cyclopropyl.

Other preferred compounds of formula (I) according to the invention are those wherein A is substituted by up to five groups R which can be the same or different and are selected in the list consisting of halogen atoms; cyano; nitro; hydroxy; amino; sulfanyl; pentafluoro-$\lambda^6$-sulfanyl; formyl; formyloxy; formylamino; carboxy; carbamoyl; N-hydroxycarbamoyl; carbamate; (hydroxyimino)-$C_1$-$C_6$-alkyl; $C_1$-$C_5$-alkylamino; di-$C_1$-$C_5$-alkylamino; tri($C_1$-$C_5$-alkyl)silyl; $C_1$-$C_5$-alkylsulfanyl; $C_1$-$C_5$-halogenoalkylsulfanyl comprising up to 5 halogen atoms which can be the same or different; $C_1$-$C_5$-alkyl; $C_1$-$C_5$-halogenoalkyl comprising up to 5 halogen atoms which can be the same or different; $C_2$-$C_5$-alkenyl; $C_2$-$C_5$-halogenoalkenyl comprising up to 5 halogen atoms which can be the same or different; $C_2$-$C_5$-alkynyl; $C_2$-$C_5$-halogenoalkynyl comprising up to 5 halogen atoms which can be the same or different; $C_1$-$C_5$-alkoxy; $C_1$-$C_5$-halogenoalkoxy comprising up to 5 halogen atoms which can be the same or different; $C_2$-$C_5$-alkenyloxy; $C_2$-$C_5$-halogenoalkenyloxy comprising up to 5 halogen atoms which can be the same or different; $C_2$-$C_5$-alkynyloxy; $C_2$-$C_5$-halogenoalkynyloxy comprising up to 5 halogen atoms which can be the same or different; $C_3$-$C_7$-cycloalkyl; $C_3$-$C_7$-halogenocycloalkyl comprising up to 5 halogen atoms which can be the same or different; $C_1$-$C_5$-alkylcarbonyl; $C_1$-$C_5$-halogenoalkylcarbonyl comprising up to 5 halogen atoms which can be the same or different; $C_1$-$C_5$-alkylcarbamoyl; di-$C_1$-$C_5$-alkylcarbamoyl; N—$C_1$-$C_5$-alkyloxycarbamoyl; $C_1$-$C_5$-alkoxycarbamoyl; N—$C_1$-$C_5$-alkyl-$C_1$-$C_5$-alkoxycarbamoyl; $C_1$-$C_5$-alkoxycarbonyl; $C_1$-$C_5$-halogenoalkoxycarbonyl comprising up to 5 halogen atoms which can be the same or different; $C_1$-$C_5$-alkylcarbonyloxy; $C_1$-$C_5$-halogenoalkylcarbonyloxy comprising up to 5 halogen atoms which can be the same or different; $C_1$-$C_5$-alkylcarbonylamino; $C_1$-$C_5$-halogenoalkylcarbonylamino comprising up to 5 halogen atoms which can be the same or different; $C_1$-$C_5$-alkylaminocarbonyloxy; di-$C_1$-$C_5$-alkylaminocarbonyloxy; $C_1$-$C_5$-alkyloxycarbonyloxy; $C_1$-$C_5$-alkylsulphenyl; $C_1$-$C_5$-halogenoalkylsulphenyl comprising up to 5 halogen atoms which can be the same or different; $C_1$-$C_5$-alkylsulphinyl; $C_1$-$C_5$-halogenoalkylsulphinyl comprising up to 5 halogen atoms which can be the same or different; $C_1$-$C_5$-alkylsulphonyl; $C_1$-$C_5$-halogenoalkylsulphonyl comprising up to 5 halogen atoms which can be the same or different; $C_1$-$C_5$ alkoxyimino; ($C_1$-$C_5$-alkoxyimino)-$C_1$-$C_5$-alkyl; ($C_1$-$C_5$-alkenyloxyimino)-$C_1$-$C_5$-alkyl; ($C_1$-$C_5$-alkynyloxyimino)-$C_1$-$C_5$-alkyl; a (benzyloxyimino)-$C_1$-$C_5$-alkyl; benzyloxy; benzylsulfanyl; benzylamino; naphtyl; halogenophenyl comprising up to 5 halogen atoms which can be the same or different; halogenophenoxy comprising up to 5 halogen atoms which can be the same or different.

More preferred compounds according to the invention are those wherein A is substituted by up to five groups R which can be the same or different and can be selected in the list consisting of: halogen atoms; cyano; $C_1$-$C_5$-alkyl; $C_1$-$C_5$-alkoxy; $C_2$-$C_5$-alkenyloxy; $C_2$-$C_5$-alkynyloxy; $C_3$-$C_5$-cycloalkyl; $C_1$-$C_5$-alkoxycarbonyl $C_1$-$C_5$-alkylsulfanyl; $C_1$-$C_5$-alkylamino; di($C_1$-$C_5$-alkyl)amino; phenyl; phenoxy; benzyl; $C_1$-$C_5$-halogenoalkyl comprising up to 5 halogen atoms which can be the same or different; $C_1$-$C_5$-halogenocycloalkyl comprising up to 5 halogen atoms which can be the same or different; $C_1$-$C_5$-halogenoalkoxy comprising up to 5 halogen atoms which can be the same or different; halogenophenyl comprising up to 5 halogen atoms which can be the same or different and halogenophenoxy comprising up to 5 halogen atoms which can be the same or different.

Examples of preferred compounds according to the invention are compounds wherein A represents a five membered heterocycle, advantageously A can be selected in the list consisting of:
a heterocycle of formula ($A^1$)

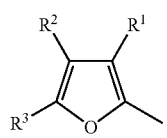

wherein
$R^1$ to $R^3$ which can be the same or different represent a hydrogen atom; a halogen atom; a $C_1$-$C_5$-alkyl or a $C_1$-$C_5$-halogenoalkyl comprising up to 5 halogen atoms which can be the same or different;

a heterocycle of formula ($A^2$)

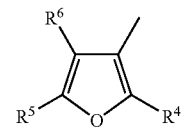

wherein:
$R^4$ represents a hydrogen atom; a halogen atom; a $C_1$-$C_5$-alkyl or a $C_1$-$C_5$-halogenoalkyl comprising up to 5 halogen atoms which can be the same or different;
$R^5$ represents a hydrogen atom or $C_1$-$C_5$-alkyl;
$R^6$ represents a hydrogen or a halogen atom;
a heterocycle of formula ($A^3$)

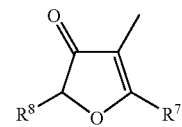

wherein:
$R^7$ and $R^8$ which can be the same or different represent a hydrogen atom or $C_1$-$C_5$-alkyl;
a heterocycle of formula ($A^4$)

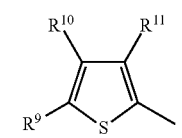

wherein:
$R^9$ represents a hydrogen; a halogen atom; a $C_1$-$C_5$-alkyl; an amino or a $C_1$-$C_5$-halogenoalkyl comprising up to 5 halogen atoms which can be the same or different;
$R^{10}$ represents a hydrogen or a halogen atom;
$R^{11}$ represents a hydrogen atom, a halogen atom, a $C_1$-$C_5$-alkyl or a $C_1$-$C_5$-alkoxy;
a heterocycle of formula ($A^5$)

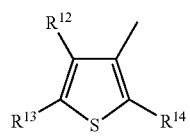

wherein:
$R^{12}$ represents a hydrogen atom; a halogen atom; a $C_1$-$C_5$-alkyl; a $C_1$-$C_5$-alkoxy; an amino or a $C_1$-$C_5$-halogenoalkyl comprising up to 5 halogen atoms which can be the same or different;
$R^{13}$ represents a hydrogen atom, a halogen atom or a $C_1$-$C_5$-alkyl;
$R^{14}$ represents a hydrogen atom, a halogen atom; a $C_1$-$C_5$-alkyl; an amino or a $C_1$-$C_5$-halogenoalkyl comprising up to 5 halogen atoms which can be the same or different;

a heterocycle of formula ($A^6$)

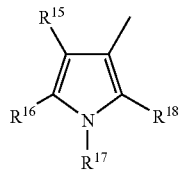

wherein:
$R^{15}$ represents a $C_1$-$C_5$-alkyl or a $C_1$-$C_5$-halogenoalkyl comprising up to 5 halogen atoms which can be the same or different;
$R^{16}$ represents a hydrogen atom or $C_1$-$C_5$-alkoxycarbonyl;
$R^{17}$ and $R^{18}$ which can be the same or different represent a hydrogen atom or $C_1$-$C_5$-alkyl;
a heterocycle of formula ($A^7$)

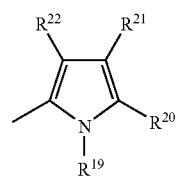

wherein:
$R^{19}$ represents a $C_1$-$C_5$-alkyl;
$R^{20}$ to $R^{22}$ which can be the same or different represent a hydrogen atom; a halogen atom or a $C_1$-$C_5$-alkyl;
a heterocycle of formula ($A^8$)

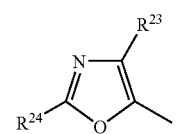

wherein:
$R^{23}$ represents a hydrogen atom; a $C_1$-$C_5$-alkyl or a $C_1$-$C_5$-halogenoalkyl comprising up to 5 halogen atoms which can be the same or different;
$R^{24}$ represents a hydrogen atom or a $C_1$-$C_5$-alkyl;
a heterocycle of formula ($A^9$)

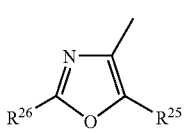

wherein
$R^{25}$ represents a hydrogen atom; a $C_1$-$C_5$-alkyl or a $C_1$-$C_5$-halogenoalkyl comprising up to 5 halogen atoms which can be the same or different;

$R^{26}$ represents a $C_1$-$C_5$-alkyl;
a heterocycle of formula ($A^{10}$)

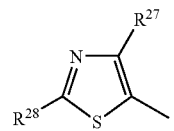

wherein:
$R^{27}$ represents a hydrogen atom; a $C_1$-$C_5$-alkyl or a $C_1$-$C_5$-halogenoalkyl comprising up to 5 halogen atoms which can be the same or different;
$R^{28}$ represents a hydrogen atom; a halogen atom, an amino; a $C_1$-$C_5$-alkyl or a phenyl;
a heterocycle of formula ($A^{11}$)

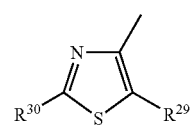

wherein:
$R^{29}$ represents a hydrogen atom; a halogen atom or a $C_1$-$C_5$-alkyl;
$R^{30}$ represents a hydrogen atom; a halogen atom; a $C_1$-$C_5$-alkyl or an amino;
a heterocycle of formula ($A^{12}$)

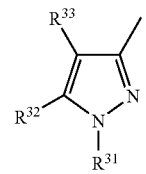

wherein:
$R^{31}$ represents a $C_1$-$C_5$-alkyl or a phenyl;
$R^{32}$ represents a hydrogen atom; a halogen atom; a $C_1$-$C_5$-alkyl or a $C_1$-$C_5$-halogenoalkyl comprising up to 5 halogen atoms which can be the same or different;
$R^{33}$ represents a hydrogen atom; a halogen atom; a nitro or a $C_1$-$C_5$-halogenoalkyl comprising up to 5 halogen atoms which can be the same or different;
a heterocycle of formula ($A^{13}$)

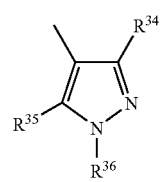

wherein
$R^{34}$ represents a hydrogen atom; a halogen atom; a $C_1$-$C_5$-alkyl; a $C_3$-$C_5$-cycloalkyl; a $C_1$-$C_5$-halogenoalkyl comprising up to halogen atoms which can be the same or different; a $C_1$-$C_5$-alkoxy; a $C_2$-$C_5$-alkynyloxy or a phenyl;

$R^{35}$ represents a hydrogen atom; a halogen atom; a $C_1$-$C_5$-alkyl; a cyano; a $C_1$-$C_5$-alkoxy; a $C_1$-$C_5$-alkylthio; a $C_1$-$C_5$-halogenoalkyl comprising up to 5 halogen atoms which can be the same or different; a $C_1$-$C_5$-alkylamino; a di($C_1$-$C_5$-alkyl)amino or a halogenophenoxy comprising up to 5 halogen atoms which can be the same or different;

$R^{36}$ represents a hydrogen atom; a $C_1$-$C_5$-alkyl or a phenyl;

a heterocycle of formula ($A^{14}$)

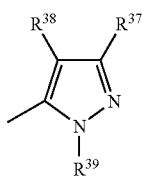

wherein:
$R^{37}$ and $R^{38}$ which can be the same or different represent a hydrogen atom; a halogen atom or a $C_1$-$C_5$-alkyl;
$R^{39}$ represents a $C_1$-$C_5$-alkyl;
a heterocycle of formula ($A^{15}$)

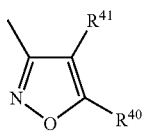

wherein:
$R^{40}$ and $R^{41}$ which can be the same or different represent a hydrogen atom; a halogen atom or a $C_1$-$C_5$-alkyl;
a heterocycle of formula ($A^{16}$)

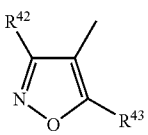

wherein:
$R^{42}$ represents a hydrogen atom or a $C_1$-$C_5$-alkyl;
$R^{43}$ represents a hydrogen atom; a $C_1$-$C_5$-alkyl; a $C_1$-$C_5$-halogenoalkyl comprising up to 5 halogen atoms which can be the same or different or an amino;
a heterocycle of formula ($A^{17}$)

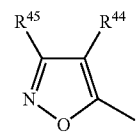

wherein:
$R^{44}$ and $R^{45}$ which can be the same or different represent a hydrogen atom; a halogen atom or a $C_1$-$C_5$-alkyl;

a heterocycle of formula ($A^{18}$)

wherein:
$R^{46}$ represents a hydrogen atom; a $C_1$-$C_5$-alkyl; a $C_1$-$C_5$-halogenoalkyl comprising up to 5 halogen atoms which can be the same or different or $C_1$-$C_5$-alkylsulfanyl;
$R^{47}$ represents a hydrogen atom; a halogen atom or a $C_1$-$C_5$-alkyl;
a heterocycle of formula ($A^{19}$)

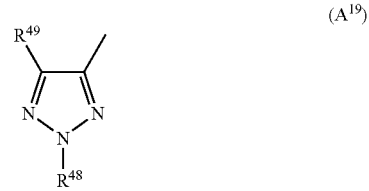

wherein
$R^{48}$ represents a hydrogen atom or a halogenophenyl comprising up to 5 halogen atoms which can be the same or different;
$R^{49}$ represents a hydrogen atom; a halogen atom or a $C_1$-$C_5$-alkyl;
a heterocycle of formula ($A^{20}$)

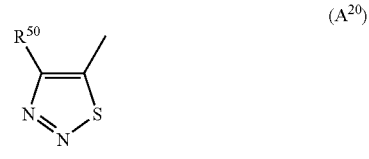

wherein:
$R^{50}$ represents a hydrogen atom or a $C_1$-$C_5$-alkyl;
a heterocycle of formula ($A^{21}$)

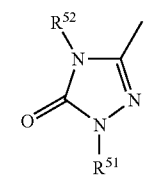

wherein:
$R^{51}$ and $R^{52}$ which can be the same or different represent a $C_{1-5}$-alkyl;

a heterocycle of formula ($A^{22}$)

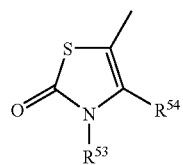

wherein
$R^{53}$ represents a $C_1$-$C_5$-alkyl;
$R^{54}$ represents a $C_1$-$C_5$-alkyl; a benzyl or a $C_1$-$C_5$-alkoxy-$C_1$-$C_5$-alkyl.

Examples of more preferred compounds according to the invention are compounds wherein A represents a five membered heterocycle of formula ($A^{13}$)
wherein:
$R^{34}$ represents a $C_1$-$C_5$-alkyl;
$R^{35}$ represents a fluorine atom;
$R^{36}$ represents a $C_1$-$C_5$-alkyl; or
wherein:
$R^{34}$ represents a $C_1$-$C_5$-halogenoalkyl comprising up to 5 halogen atoms;
$R^{35}$ represents a hydrogen or fluorine atom;
$R^{36}$ represents a $C_1$-$C_5$-alkyl; or
wherein:
$R^{34}$ represents a $C_1$-$C_5$-alkoxy;
$R^{35}$ represents hydrogen;
$R^{36}$ represents a $C_1$-$C_5$-alkyl.

Other examples of preferred compounds according to the invention are compounds wherein A represents a six membered heterocycle, advantageously A can be selected in the list consisting of:
a heterocycle of formula ($A^{23}$)

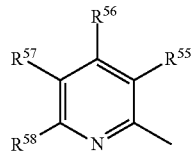

wherein
$R^{55}$, $R^{56}$ and $R^{58}$ which can be the same or different represent a hydrogen atom; a halogen atom or $C_1$-$C_5$-alkyl;
$R^{57}$ represents a hydrogen atom; a halogen atom; a $C_1$-$C_5$-alkyl or a $C_1$-$C_5$-halogenoalkyl comprising up to 5 halogen atoms which can be the same or different;
a heterocycle of formula ($A^{24}$)

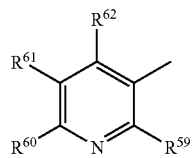

wherein:
$R^{59}$ to $R^{62}$ which can be the same or different represent a hydrogen atom; a halogen atom, a $C_1$-$C_5$-alkyl or a $C_1$-$C_5$-halogenoalkyl comprising up to 5 halogen atoms which can be the same or different;

a heterocycle of formula ($A^{25}$)

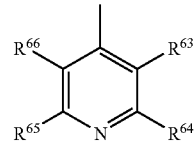

wherein:
$R^{63}$ to $R^{65}$ which can be the same or different represent a hydrogen atom; a halogen atom or a $C_1$-$C_5$-alkyl;
a heterocycle of formula ($A^{26}$)

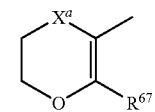

wherein:
$R^{67}$ represents a $C_1$-$C_5$-alkyl or a $C_1$-$C_5$-halogenoalkyl comprising up to 5 halogen atoms;
$X^a$ represents a sulphur atom; —SO—; —SO$_2$— or —CH$_2$—;
a heterocycle of formula ($A^{27}$)

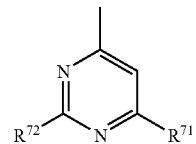

wherein:
$R^{71}$ represents a hydrogen atom or a $C_1$-$C_5$-alkyl;
$R^{72}$ represents a hydrogen atom or a halogen atom.
a heterocycle of formula ($A^{28}$)

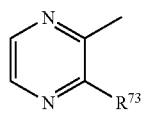

wherein:
$R^{73}$ represents hydrogen atom; a halogen atom or a $C_1$-$C_5$ alkyl.

Still other examples of preferred compounds according to the invention are compounds wherein A represents a fused heterocycle, advantageously A can be selected in the list consisting of:

a heterocycle of formula (A²⁹)

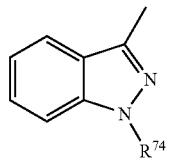

wherein
R⁷⁴ represents a $C_1$-$C_5$-alkyl;

a heterocycle of formula (A³⁰)

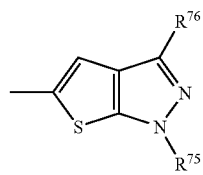

wherein
R⁷⁵ and R⁷⁶ which can be the same or different represent a $C_1$-$C_5$-alkyl.

Still other preferred compounds of formula (I) according to the invention are those wherein L represents a phenyl substituted by up to five groups X which can be the same or different and can be selected in the list consisting of halogen atom; cyano; nitro; hydroxy; amino; sulfanyl; pentafluoro-λ⁶-sulfanyl; formyl; formyloxy; formylamino; carboxy; carbamoyl; N-hydroxycarbamoyl; carbamate; (hydroxyimino)-$C_1$-$C_6$-alkyl; $C_1$-$C_5$-alkylamino; di-$C_1$-$C_5$-alkylamino; tri($C_1$-$C_5$-alkyl)silyl; $C_1$-$C_5$-alkylsulfanyl; $C_1$-$C_5$-halogenoalkylsulfanyl comprising up to 5 halogen atoms which can be the same or different; $C_1$-$C_5$-alkyl; $C_1$-$C_5$-halogenoalkyl comprising up to 5 halogen atoms which can be the same or different; $C_1$-$C_5$-alkenyl; $C_2$-$C_5$-halogenoalkenyl comprising up to 5 halogen atoms which can be the same or different; $C_2$-$C_5$-alkynyl; $C_2$-$C_5$-halogenoalkynyl comprising up to 5 halogen atoms which can be the same or different; $C_1$-$C_5$-alkoxy; $C_1$-$C_5$-halogenoalkoxy comprising up to 5 halogen atoms which can be the same or different; $C_2$-$C_5$-alkenyloxy; $C_2$-$C_5$-halogenoalkenyloxy comprising up to 5 halogen atoms which can be the same or different; $C_2$-$C_5$-alkynyloxy; $C_2$-$C_5$-halogenoalkynyloxy comprising up to 5 halogen atoms which can be the same or different; $C_3$-$C_7$-cycloalkyl; $C_3$-$C_7$-halogenocycloalkyl comprising up to 5 halogen atoms which can be the same or different; $C_1$-$C_5$-alkylcarbonyl; $C_1$-$C_5$-halogenoalkylcarbonyl comprising up to 5 halogen atoms which can be the same or different; $C_1$-$C_5$-alkylcarbamoyl; di-$C_1$-$C_5$-alkylcarbamoyl; N—$C_1$-$C_5$-alkyloxycarbamoyl; $C_1$-$C_5$-alkoxycarbamoyl; N—$C_{1-5}$-alkyl-$C_1$-$C_5$-alkoxycarbamoyl; $C_1$-$C_5$-alkoxycarbonyl; $C_1$-$C_5$-halogenoalkoxycarbonyl comprising up to 5 halogen atoms which can be the same or different; $C_1$-$C_5$-alkylcarbonyloxy; $C_1$-$C_5$-halogenoalkylcarbonyloxy comprising up to 5 halogen atoms which can be the same or different; $C_1$-$C_5$-alkylcarbonylamino; $C_1$-$C_5$-halogenoalkylcarbonylamino comprising up to 5 halogen atoms which can be the same or different; $C_1$-$C_5$-alkylaminocarbonyloxy; di-$C_1$-$C_5$-alkylaminocarbonyloxy; $C_1$-$C_5$-alkyloxycarbonyloxy; $C_1$-$C_5$-alkylsulphenyl; $C_1$-$C_5$-halogenoalkylsulphenyl comprising up to 5 halogen atoms which can be the same or different; $C_1$-$C_5$-alkylsulphinyl; $C_1$-$C_5$-halogenoalkylsulphinyl comprising up to 5 halogen atoms which can be the same or different; $C_1$-$C_5$-alkylsulphonyl; $C_1$-$C_5$-halogenoalkylsulphonyl comprising up to 5 halogen atoms which can be the same or different; $C_1$-$C_6$-alkoxyimino; ($C_1$-$C_6$-alkoxyimino)-$C_1$-$C_6$-alkyl; ($C_1$-$C_6$-alkenyloxyimino)-$C_1$-$C_6$-alkyl; ($C_1$-$C_6$-alkynyloxyimino)-$C_1$-$C_6$-alkyl; (benzyloxyimino)-$C_1$-$C_6$-alkyl; benzylsulfanyl; benzylamino; naphtyl; phenyl which can be substituted by up to five groups Q which can be the same or different; phenoxy which can be substituted by up to five groups Q which can be the same or different; benzyloxy which can be substituted by up to five groups Q which can be the same or different; phenylamino which can be substituted by up to five groups Q which can be the same or different, phenylsulfanyl which can be substituted by up to five groups Q which can be the same or different; phenylmethylene which can be substituted by up to five groups Q which can be the same or different; pyridinyl which can be substituted by up to four groups Q which can be the same or different and pyndinyloxy which can be substituted by up to four groups Q which can be the same or different.

More preferred compounds of formula (I) according to the invention are those wherein L represents a phenyl substituted by up to five groups X which can be the same or different and are selected in the list consisting of halogen atom; cyano; nitro; $C_1$-$C_5$-alkyl; $C_2$-$C_5$-alkenyl; $C_2$-$C_5$-alkynyl; $C_1$-$C_5$-halogenoalkyl comprising up to 5 halogen atoms which can be the same or different; $C_1$-$C_5$-alkoxy; $C_2$-$C_5$-alkenyloxy; $C_2$-$C_5$-alkynyloxy; $C_1$-$C_5$-halogenoalkoxy comprising up to 5 halogen atoms which can be the same or different; tri($C_1$-$C_5$-alkyl)silyl; naphtyl; phenyl which can be substituted by up to five groups Q which can be the same or different; phenoxy which can be substituted by up to five groups Q which can be the same or different; phenylsulfanyl which can be substituted by up to five groups Q which can be the same or different; pyridinyl which can be substituted by up to four groups Q which can be the same or different and pyridinyloxy which can be substituted by up to four groups Q which can be the same or different.

Still more preferred compounds of formula (I) according to the invention are those wherein L represents a 5-, 6 or 7-membered aromatic or non aromatic heterocycle substituted by up to five groups X which can be the same or different and are selected in the list consisting of halogen atom; cyano; nitro; $C_1$-$C_5$-alkyl; $C_2$-$C_8$-alkenyl; $C_2$-$C_5$-alkynyl; $C_1$-$C_5$-halogenoalkyl comprising up to 5 halogen atoms which can be the same or different; $C_1$-$C_5$-alkoxy; $C_2$-$C_5$-alkenyloxy; $C_2$-$C_5$-alkynyloxy; $C_1$-$C_5$-halogenoalkoxy comprising up to 5 halogen atoms which can be the same or different; tri($C_1$-$C_5$-alkyl)silyl; phenyl which can be substituted by up to five groups Q which can be the same or different and phenoxy which can be substituted by up to five groups Q which can be the same or different.

Examples of preferred compounds according to the invention are compounds wherein L represents a five membered heterocycle, advantageously L can be selected in the list consisting of:

a heterocycle of formula ($L^1$):

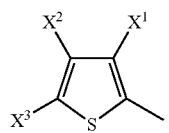
($L^1$)

wherein:
$X^1$ to $X^3$ which can be the same or different represent a hydrogen atom; a halogen atom or a $C_1$-$C_5$-alkyl.

a heterocycle of formula ($L^2$)

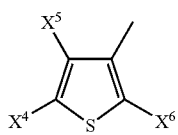
($L^2$)

wherein:
$X^4$ represents a hydrogen atom; a halogen atom; a $C_1$-$C_5$-alkyl or a $C_1$-$C_5$-alkyloxycarbonyl;
$X^5$ represents a hydrogen atom or a halogen atom;
$X^6$ represents a hydrogen atom, a halogen atom or a $C_1$-$C_5$-alkyl;

a heterocycle of formula ($L^3$)

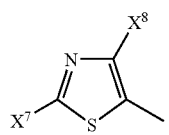
($L^3$)

wherein:
$X^7$ represents a hydrogen atom; a halogen atom or a $C_1$-$C_5$-alkyl;
$X^8$ represents a hydrogen atom or a $C_1$-$C_5$-alkyl.

a heterocycle of formula ($L^4$)

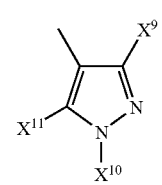
($L^4$)

wherein:
$X^9$ represents a $C_1$-$C_5$-alkyl or a $C_1$-$C_5$-halogenoalkyl comprising up to 5 halogen atoms which can be the same or different;
$X^{10}$ represents a $C_1$-$C_5$-alkyl or a phenyl;
$X^{11}$ represents a hydrogen atom; a halogen atom or a $C_1$-$C_5$-alkyl.

Other examples of preferred compounds according to the invention are compounds wherein L represents a six membered heterocycle, advantageously L can be selected in the list consisting of:

a heterocycle of formula ($L^5$)

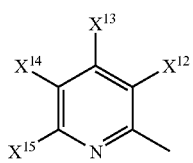
($L^5$)

wherein:
$X^{12}$, $X^{13}$ and $X^{15}$ which can be the same or different represent a hydrogen atom or a halogen atom;
$X^{14}$ represents a hydrogen atom, a halogen atom or a $C_1$-$C_5$-halogenoalkyl comprising up to 5 halogen atoms which can be the same or different;

a heterocycle of formula ($L^6$)

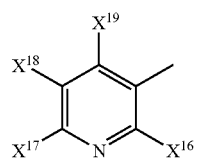
($L^6$)

wherein
$X^{16}$ to $X^{19}$ which can be the same or different represent a hydrogen; a halogen atom or a $C_1$-$C_5$-alkyl.

Still other examples of preferred compounds according to the invention are compounds wherein L represents a fused heterocycle, advantageously L can be selected in the list consisting of:

a heterocycle of formula ($L^7$)

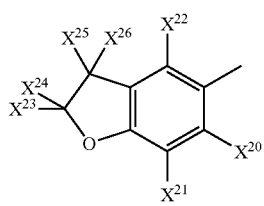
($L^7$)

wherein:
$X^{20}$ to $X^{22}$ which can be the same or different represent a hydrogen atom; a halogen atom or a $C_1$-$C_5$ alkyl;
$X^{23}$ to $X^{25}$ which can be the same or different represent a hydrogen atom or a $C_1$-$C_5$ alkyl;

a heterocycle of formula ($L^8$)

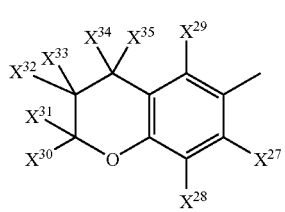
($L^8$)

wherein:
$X^{27}$ to $X^{29}$ which can be the same or different represent a hydrogen atom; a halogen atom or a $C_1$-$C_5$ alkyl;

$X^{30}$ to $X^{35}$ which can be the same or different represent a hydrogen atom or a $C_1$-$C_5$ alkyl;
a heterocycle of formula ($L^9$)

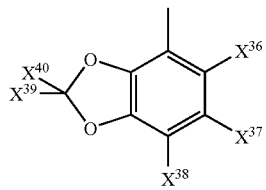

wherein:
$X^{36}$ to $X^{38}$ which can be the same or different represent a hydrogen atom; a halogen atom or a $C_1$-$C_5$ alkyl;
$X^{39}$ and $X^{40}$ which can be the same or different represent a hydrogen atom; a halogen atom or a $C_1$-$C_5$ alkyl;
a heterocycle of formula ($L^{10}$)

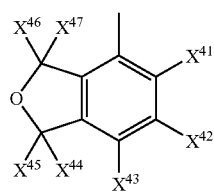

wherein:
$X^{41}$ to $X^{43}$ which can be the same or different represent a hydrogen atom; a halogen atom or a $C_1$-$C_5$ alkyl;
$X^{44}$ to $X^{47}$ which can be the same or different represent a hydrogen atom or a $C_1$-$C_5$ alkyl.

Still other preferred compounds of formula (I) according to the invention are those wherein Q can be selected in the list consisting of: halogen atom; cyano; nitro; $C_1$-$C_5$-alkyl; $C_1$-$C_5$-alkoxy; $C_1$-$C_5$-alkylsulfanyl; benzyloxy; $C_1$-$C_5$-alkylamino; di-$C_1$-$C_5$-alkylamino; $C_1$-$C_5$-halogenoalkyl comprising 1 to 5 halogen atoms which can be the same or different; $C_1$-$C_5$-halogenoalkoxy comprising 1 to 5 halogen atoms which can be the same or different and tri($C_1$-$C_5$)alkylsilyl.

The above mentioned preferences with regard to the substituents of the compounds according to the invention can be combined in various manners. These combinations of preferred features thus provide sub-classes of compounds according to the invention. Examples of such sub-classes of preferred compounds according to the invention can combined:
preferred features of E with preferred features of A;
preferred features of E with preferred features of L;
preferred features of A with preferred features of L;
preferred features of L with preferred features of Q;
preferred features of E with preferred features of A and L;
preferred features of E with preferred features of L and Q;
preferred features of A with preferred features of L and Q;
preferred features of E with preferred features of A, L and Q.

In these combinations of preferred features of the substituents of the compounds according to the invention, the said preferred features can also be selected among the more preferred features of each of E, A, L and Q so as to form most preferred subclasses of compounds according to the invention.

The present invention also relates to a process for the preparation of the compounds of formula (I).

Thus according to a further aspect according to the invention, there is provided a process P1 for the preparation of compound of formula (I) and illustrated according to the following reaction scheme:

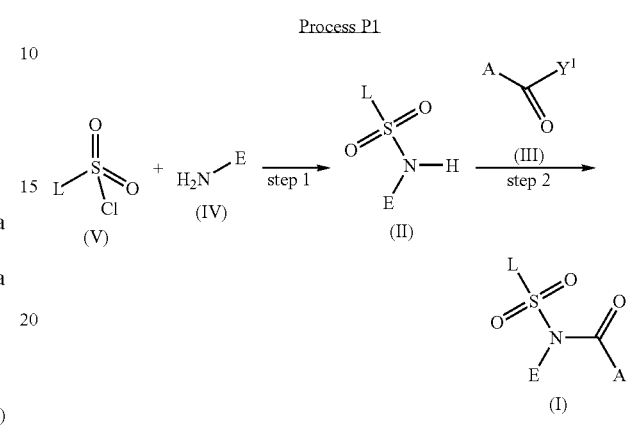

wherein
A, E and L are as defined above;
$Y^1$ represents a halogen atom or a hydroxyl group.

In process P1, step 1 may be performed in the presence of an acid binder and in the presence of a solvent.

In process P1, step 2 may be performed in the presence of a solvent, in the presence of an acid binder and in the presence of a condensing agent.

Sulfonylchloride derivatives of formula (V) are known or can be prepared by known processes (J. Med. Chem., 1983, p 1181; JP11292865; Bioorg. Med. Chem., 2002, p 3649-3661).

Amine derivatives of formula (IV) are also known or can be prepared by known processes (J. Org. Chem., 1998, p 100402-10044; J. Org. Chem., 2003, p 7134-7136).

Carboxylic acids, acid chlorides, acid bromides or acid fluorides of formula (III) are known or can be prepared by known processes (WO9311117, p 16-20; Nucleosides & Nucleotides, 1987, p 737-759; Bioorg. Med. Chem. Lett., 2002, p 2105-2108).

According to the invention, compounds of formula (Ia) are compounds of formula (I) wherein L is substituted by a halogen atom. These compounds of formula (Ia) can be prepared according to process P1.

The present invention also provides a process P2 which permits to prepare compounds of formula (I) starting from compounds of formula (Ia).

Process P2 can be illustrated according to the following reaction scheme:

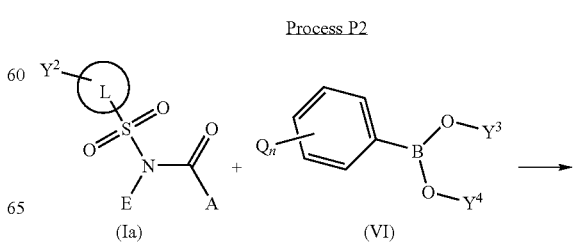

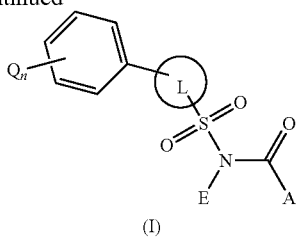

wherein
A, E, L and Q are as defined above;
$Y^2$ is halogen atom;
$Y^3$ and $Y^4$ each represent hydrogen or together represent tetramethylethylene;
Q is as defined above;
n is 0, 1, 2, 3, or 5.

Process P2 may be performed in the presence of a catalyst, in the presence of an acid binder and in the presence of a solvent.

Boronic acid derivatives of formula (VI) are known compounds.

The present invention also provides a process P3 which also permits to prepare compounds of formula (I) starting from compounds of formula (Ia).

Process P3 can be illustrated according to the following reaction scheme:

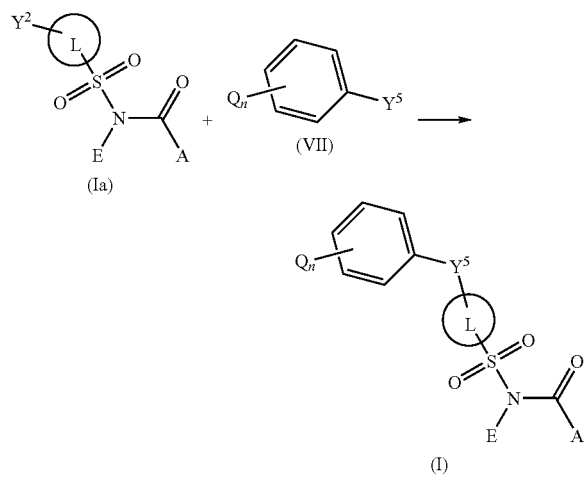

wherein
A, E, L and Q are as defined above;
$Y^2$ is halogen atom;
$Y^5$ is sulphur, oxygen or $C_1$-$C_5$-alkylamino;
n is 0, 1, 2, 3, or 5.

Process P3 may also be performed in the presence of a catalyst in the presence of an acid binder and in the presence of a solvent.

Phenol, thiophenol or aniline derivatives of formula (VII) are known compounds.

Suitable acid binders for carrying out the processes P1, P2 and P3 according to the invention can be inorganic and organic bases which are customary for such reactions. Preference is given to using alkaline earth metal or alkali metal hydroxides, such as sodium hydroxide, calcium hydroxide, potassium hydroxide or other ammonium hydroxide derivatives; alkali metal carbonates, such as sodium carbonate, potassium carbonate, potassium bicarbonate, sodium bicarbonate; alkali metal or alkaline earth metal acetates, such as sodium acetate, potassium acetate, calcium acetate; and also tertiary amines, such as trimethylamine, triethylamine, tributylamine, N,N-dimethylaniline, pyridine, N-methylpiperidine, N,N-dimethylaminopyridine, diazabicyclooctane (DABCO), diazabicyclononene (DBN) or diazabicycloundecene (DBU).

It is also possible to work in the absence of any additional acid binder or to employ an excess of the amine derivative, so that it simultaneously acts as an acid binder.

Suitable solvents for carrying out the processes P1, P2 and P3 according to the invention can be customary inert organic solvents. Preference is given to using optionally halogen atomated aliphatic, alicyclic or aromatic hydrocarbons, such as petroleum ether, hexane, heptane, cyclohexane, methylcyclohexane, benzene, toluene, xylene or decalin; chlorobenzene, dichlorobenzene, dichloromethane, chloroform, carbon tetrachloride, dichlorethane or trichlorethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate, sulphoxides, such as dimethyl sulphoxide, or sulphones, such as sulpholane.

Processes P2 and P3 according to the invention can be carried out in the presence of a catalyst, such as a metal salt or complex. Suitable metal derivatives for this purpose are based on copper or palladium. Suitable metal salts or complexes for this purpose are copper chloride, copper iodide, copper oxide, palladium chloride, palladium acetate, tetrakis(triphenylphosphine)palladium, bis(triphenylphosphine)palladium dichloride or 1,1'-bis(diphenyl-phosphino) ferrocenepalladium(II) chloride.

It is also possible to generate a palladium complex in the reaction mixture by separate addition to the reaction of a palladium salt and a complex ligand, such as triethylphosphine, tri-tert-butylphosphine, tricyclohexylphosphine, 2-(dicyclohexylphosphine)biphenyl, 2-(di-tert-butylphosphine)biphenyl, 2-(dicyclohexylphosphine)-2'-(N,N-dimethylamino)biphenyl, triphenylphosphine, tris-(o-tolyl)phosphine, sodium 3-(diphenylphosphino)benzenesulphonate, tris-2-(methoxyphenylyphosphine, 2,2'-bis(diphenylphosphine)-1,1'-binaphthyl, 1,4-bis(diphenylphosphine)butane, 1,2-bis(diphenylphosphine)ethane, 1,4-bis(dicyclohexylphosphine)butane, 1,2-bis(dicyclohexylphosphine)ethane, 2-(dicyclohexylphosphine)-2'-(N,N-dimethylamino)-biphenyl, bis(diphenylphosphino)ferrocene or tris-(2,4-tert-butylphenyl)phosphite.

When carrying out the processes P1, P2 and P3 according to the invention, the reaction temperatures can be varied within a relatively wide range. In general, these processes are carried out at temperatures from 0° C. to 160° C., preferably from 10° C. to 120° C. A way to control the temperature for the processes according to the invention, notably process P3, is to use micro-wave technology.

Processes P1, P2 and P3 according to the invention are generally carried out under atmospheric pressure. It is also possible to operate under elevated or reduced pressure.

When carrying out step 1 of process P1 according to the invention, 1 mol or an excess of the amine derivative of formula (IV) and from 1 to 3 mol of acid binder can be employed per mole of sulfonyl chloride of formula (V).

It is also possible to employ the reaction components in other ratios. Work-up is carried out by known methods.

In general, the reaction mixture is concentrated under reduced pressure. The residue that remains can be freed by known methods, such as chromatography or recrystallization, from any impurities that may still be present.

When carrying out step 2 of process P1 according to the invention, 1 mol or an excess of the acid halide derivative of formula (III) and from 1 to 3 mol of acid binder can be employed per mole of sulfonamide derivative of formula (II).

It is also possible to employ the reaction components in other ratios. Work-up is carried out by known methods.

In general, the reaction mixture is treated with water and the organic phase is separated off and, after drying, concentrated under reduced pressure. The residue that remains can, if appropriate, be freed by known methods, such as chromatography or recrystallization, from any impurities that may still be present.

When carrying out process P2 according to the invention, 1 mol or an excess of the boronic acid derivative of formula (VI) and from 1 to 5 mol of acid binder and from 0.5 to 5 mol percent of a catalyst can be employed per mole of sulfonylamide of formula (Ia).

It is also possible to employ the reaction components in other ratios. Work-up is carried out by known methods.

In general, the reaction mixture is treated with water and the precipitate is separated off and dried. The residue that remains can, if appropriate, be freed by known methods, such as chromatography or recrystallization, from any impurities that may still be present.

When carrying out process P3 according to the invention, 1 mol or an excess of the phenol, thiophenol or aniline derivative of formula (VII) and from 1 to 10 mol of acid binder and from 0.5 to 5 mol percent of a catalyst can be employed per mole of sulfonylamide derivative of formula (Ia).

It is also possible to employ the reaction components in other ratios. Work-up is carried out by known methods.

In general, the reaction mixture is concentrated under reduced pressure. The residue that remains can, if appropriate, be freed by known methods, such as chromatography or recrystallization, from any impurities that may still be present.

Compounds according to the invention can be prepared according to the above described processes. It will nevertheless be understood that, on the basis of his general knowledge and of available publications, the skilled worker will be able to adapt these processes according to the specifics of each of the compounds which it is desired to synthesise.

In a further aspect, the present invention also relates to a fungicide composition comprising an effective and non-phytotoxic amount of an active compound of formula (I).

The expression "effective and non-phytotoxic amount" means an amount of composition according to the invention which is sufficient to control or destroy the fungi present or liable to appear on the crops, and which does not entail any appreciable symptom of phytotoxicity for the said crops. Such an amount can vary within a wide range depending on the fungus to be controlled, the type of crop, the climatic conditions and the compounds included in the fungicide composition according to the invention.

This amount can be determined by systematic field trials, which are within the capabilities of a person skilled in the art.

Thus, according to the invention, there is provided a fungicide composition comprising, as an active ingredient, an effective amount of a compound of formula (I). as defined above and an agriculturally acceptable support, carrier or filler.

According to the invention, the term "support" denotes a natural or synthetic, organic or inorganic compound with which the active compound of formula (I) is combined or associated to make it easier to apply, notably to the parts of the plant. This support is thus generally inert and should be agriculturally acceptable. The support may be a solid or a liquid. Examples of suitable supports include clays, natural or synthetic silicates, silica, resins, waxes, solid fertilisers, water, alcohols, in particular butanol, organic solvents, mineral and plant oils and derivatives thereof. Mixtures of such supports may also be used.

The composition according to the invention may also comprise additional components. In particular, the composition may further comprise a surfactant. The surfactant can be an emulsifier, a dispersing agent or a wetting agent of ionic or non-ionic type or a mixture of such surfactants. Mention may be made, for example, of polyacrylic acid salts, lignosulphonic acid salts, phenolsulphonic or naphthalenesulphonic acid salts, polycondensates of ethylene oxide with fatty alcohols or with fatty acids or with fatty amines, substituted phenols (in particular alkylphenols or arylphenols), salts of sulphosuccinic acid esters, taurine derivatives (in particular alkyl taurates), phosphoric esters of polyoxyethylated alcohols or phenols, fatty acid esters of polyols, and derivatives of the above compounds containing sulphate, sulphonate and phosphate functions. The presence of at least one surfactant is generally essential when the active compound and/or the inert support are water-insoluble and when the vector agent for the application is water. Preferably, surfactant content may be comprised from 5% to 40% by weight of the composition.

Optionally, additional components may also be included, e.g. protective colloids, adhesives, thickeners, thixotropic agents, penetration agents, stabilisers, sequestering agents. More generally, the active compounds can be combined with any solid or liquid additive, which complies with the usual formulation techniques.

In general, the composition according to the invention may contain from 0.05 to 99% by weight of active compound, preferably 10 to 70% by weight.

Compositions according to the invention can be used in various forms such as aerosol dispenser, capsule suspension, cold fogging concentrate, dustable powder, emulsifiable concentrate, emulsion oil in water, emulsion water in oil, encapsulated granule, fine granule, flowable concentrate for seed treatment, gas (under pressure), gas generating product, granule, hot fogging concentrate, macrogranule, microgranule, oil dispersible powder, oil miscible flowable concentrate, oil miscible liquid, paste, plant rodlet, powder for dry seed treatment, seed coated with a pesticide, soluble concentrate, soluble powder, solution for seed treatment, suspension concentrate (flowable concentrate), ultra low volume (ULV) liquid, ultra low volume (ULV) suspension, water dispersible granules or tablets, water dispersible powder for slurry treatment, water soluble granules or tablets, water soluble powder for seed treatment and wettable powder.

These compositions include not only compositions which are ready to be applied to the plant or seed to be treated by means of a suitable device, such as a spraying or dusting device, but also concentrated commercial compositions which must be diluted before application to the crop.

The compounds according to the invention can also be mixed with one or more insecticide, fungicide, bactericide, attractant, acaricide or pheromone active substance or other compounds with biological activity. The mixtures thus obtained have a broadened spectrum of activity.

The mixtures with other fungicide compounds are particularly advantageous. Examples of suitable fungicide mixing partners can be selected in the list consisting of B1) a compound capable to inhibit the nucleic acid synthesis like benalaxyl, benalaxyl-M, bupirimate, chiralaxyl, clozylacon, dimethirimol, ethirimol, furalaxyl, hymexazol, metalaxyl-M, ofurace, oxadixyl, oxolinic acid;

B2) a compound capable to inhibit the mitosis and cell division like benomyl, carbendazim, diethofencarb, fuberidazole, pencycuron, thiabendazole thiophanate-methyl, zoxamide;

B3) a compound capable to inhibit the respiration for example as CI-respiration inhibitor like diflumetorim;

as CII-respiration inhibitor like boscalid, carboxin, fenfuram, flutolanil, furametpyr, mepronil, oxycarboxine, penthiopyrad, thifluzamide;

as CIII-respiration inhibitor like azoxystrobin, cyazofamid, dimoxystrobin, enestrobin, famoxadone, fenamidone, fluoxastrobin, kresoxim-methyl, metominostrobin, orysastrobin, pyraclostrobin, picoxystrobin, trifloxystrobin;

B4) a compound capable of to act as an uncoupler like dinocap, fluazinam;

B5) a compound capable to inhibit ATP production like fentin acetate, fentin chloride, fentin hydroxide, silthiofam;

B6) a compound capable to inhibit M and protein biosynthesis like andoprim, blasticidin-S, cyprodinil, kasugamycin, kasugamycin hydrochloride hydrate, mepanipyrim, pyrimethanil;

B7) a compound capable to inhibit the signal transduction like fenpiclonil, fludioxonil, quinoxyfen;

B8) a compound capable to inhibit lipid and membrane synthesis like chlozolinate, iprodione, procymidone, vinclozolin, pyrazophos, edifenphos, iprobenfos (IBP), isoprothiolane, tolclofos-methyl, biphenyl, iodocarb, propamocarb, propamocarb-hydrochloride;

B9) a compound capable to inhibit ergosterol biosynthesis like fenhexamid, azaconazole, bitertanol, bromuconazole, cyproconazole, diclobutrazole, difenoconazole, diniconazole, diniconazole-M, epoxiconazole, etaconazole, fenbuconazole, fluquinconazole, flusilazole, flutriafol, furconazole, furconazole-cis, hexaconazole, imibenconazole, ipconazole, metconazole, myclobutanil, paclobutrazol, penconazole, propiconazole, prothioconazole, simeconazole, tebuconazole, tetraconazole, triadimefon, triadimenol, triticonazole, uniconazole, voriconazole, imazalil, imazalil sulfate, oxpoconazole, fenarimol, flurprimidol, nuarimol, pyrifenox, triforine, pefurazoate, prochloraz, triflumizole, viniconazole, aldimorph, dodemorph, dodemorph acetate, fenpropimorph, tridemorph, fenpropidin, spiroxamine, naftifine, pyributicarb, terbinafine;

B10) a compound capable to inhibit cell wall synthesis like benthiavalicarb, bialaphos, dimethomorph, flumorph, iprovalicarb, polyoxins, polyoxorim, validamycin A;

B11) a compound capable to inhibit melanine biosynthesis like carpropamid, diclocymet, fenoxanil, phtalide, pyroquilon, tricyclazole;

B12) a compound capable to induce a host defence like acibenzolar-S-methyl, probenazole, tiadinil;

B13) a compound capable to have a multisite action like captafol, captan, chlorothalonil, copper preparations such as copper hydroxide, copper naphthenate, copper oxychloride, copper sulphate, copper oxide, oxine-copper and Bordeaux mixture, dichlofluanid, dithianon, dodine, dodine free base, ferbam, fluorofolpet, folpet, guazatine, guazatine acetate, iminoctadine, iminoctadine albesilate, iminoctadine triacetate, mancopper, mancozeb, maneb, metiram, metiram zinc, propineb, sulphur and sulphur preparations including calcium polysulphide, thiram, tolylfluanid, zineb, ziram;

B14) a compound selected in the list consisting of: amibromdole, benthiazole, bethoxazin, capsimycin, carvone, chinomethionat, chloropicrin, cufraneb, cyflufenamid, cymoxanil, dazomet, debacarb, diclomezine, dichlorophen, dicloran, difenzoquat, difenzoquat methylsulphate, diphenylamine, ethaboxam, ferimzone, flumetover, flusulfamide, fosetyl-aluminium, fosetyl-calcium, fosetyl-sodium, fluopicolide, fluoroimide, hexachlorobenzene, 8-hydroxyquinoline sulfate, irumamycin, methasulphocarb, metrafenone, methyl isothiocyanate, mildiomycin, natamycin, nickel dimethyldithiocarbamate, nitrothal-isopropyl, octhilinone, oxamocarb, oxyfenthiin, pentachlorophenol and salts, 2-phenylphenol and salts, phosphorous acid and its salts, piperalin, propanosine-sodium, proquinazid, pyrrolnitrine, quintozene, tecloftalam, tecnazene, triazoxide, trichlamide, zarilamid and 2,3,5,6-tetrachloro-(methylsulfonyl)-pyridine, N-(4-Chloro-2-nitrophenyl)-N-ethyl-4-methyl-benzenesulfonamide, 2-amino-4-methyl-N-phenyl-5-thiazolecarboxamide, 2-chloro-N-(2,3-dihydro-1,1,3-trimethyl-1H-inden-4-yl)-3-pyridincarboxamide, 3-[5-(4-chlorophenyl)-2,3-dimethylisoxazolidin-3-yl]pyridine, cis-1-(4-chlorophenyl)-2-(1H-1,2,4-triazole-1-yl)-cycloheptanol, methyl 1-(2,3-dihydro-2,2-dimethyl-1H-inden-1-yl)-1H-imidazole-5-carboxylate, 3,4,5-trichloro-2,6-pyridinedicarbonitrile, Methyl 2-[[[cyclopropyl[(4-methoxyphenyl)imino]methyl]thio]methyl]-.alpha.-(methoxymethylene)-benzeneacetate, 4-Chloro-alpha-propynyloxy-N-[2-[3-methoxy-4-(2-propynyloxy)phenyl]ethyl]-benzeneacetamide, (2S)—N-[2-[4-[[3-(4-chlorophenyl)-2-propynyl]oxy]-3-methoxyphenyl]ethyl]-3-methyl-2-[(methylsulfonyl)amino]-butanamide, 5-chloro-7-(4-methylpiperidin-1-yl)-6-(2,4,6-trifluorophenyl)[1,2,4]triazolo[1,5-a]pyrimidine, 5-chloro-6-(2,4,6-trifluorophenyl)-N-[(1R)-1,2,2-trimethylpropyl][1,2,4]triazolo[1,5-a]pyrimidin-7-amine, 5-chloro-N-[(1R)-1,2-dimethylpropyl]-6-(2,4,6-trifluorophenyl)[1,2,4]triazolo[1,5-a]pyrimidin-7-amine, N-[1-(5-bromo-3-chloropyridin-2-yl)ethyl]-2,4-dichloronicotinamide, N-(5-bromo-3-chloropyridin-2-yl)methyl-2,4-dichloronicotinamide, 2-butoxy-6-iodo-3-propyl-benzopyranon-4-one, N-((Z)-[(cyclopropylmethoxy)imino][6-(difluoromethoxy)-2,3-difluorophanyl]methyl)-2-phenylacetamide, N-(3-ethyl-3,5,5-trimethyl-cyclohexyl)-3-formylamino-2-hydroxy-benzamide, 2-[[[[1-[3(1Fluoro-2-phenylethyl)oxy]phenyl]ethylidene]amino]oxy]methyl]-alpha-(methoxyimino)-N-methyl-alphaE-benzeneacetamide, N-(2-[3-chloro-5-(trifluoromethyl)pyridin-2-yl]ethyl)-2-(trifluoromethyl)benzamide, N-(3',4'-dichloro-5-fluorobiphenyl-2-yl)-3-(difluoromethyl)-1-methyl-1H-pyrazole-4-carboxamide, 2-(2-{6-(3-chloro-2-methylphenoxy)-5-fluoropyrimidin-4-yl]oxy}phenyl)-2-(methoxyimino)-N-methylacetamide, 1-[(4-methoxyphenoxy)methyl]-2,2-dimethylpropyl]-1H-imidazole-1-carboxylic acid, O-[1-[(4-methoxyphenoxy)methyl]-2,2-dimethylpropyl]-1H-imidazole-1-carbothioic acid The composition according to the invention comprising a mixture with a bactericide compound may also be particularly advantageous. Examples of suitable bactericide mixing partners may be selected in the list consisting of bronopol, dichlorophen, nitrapyrin, nickel dimethyldithiocarbamate, kasugamycin, octhilinone, furancarboxylic acid, oxytetracydine, probenazole, streptomycin, tecloftalam, copper sulphate and other copper preparations.

The compound of formula (I) and the fungicide composition according to the invention can be used to curatively or preventively control phytopathogenic fungi of plants and crops. Thus, according to a further aspect according to the invention, there is provided a method for curatively or preventively controlling phytopathogenic fungi of plants or crops characterised in that a compound of formula (I) or a fungicide composition according to the invention is applied to the seed, the plant or to the fruit of the plant or to the soil wherein the plant is growing or wherein it is desired to grow.

The method of treatment according to the invention may also be useful to treat propagation material such as tubers or rhizomes, but also seeds, seedlings or seedlings pricking out and plants or plants pricking out. This method of treatment can also be useful to treat roots. The method of treatment according to the invention can also be useful to treat the overground parts of the plant such as trunks, stems or stalks, leaves, flowers and fruit of the concerned plant.

Among the plants that can be protected by the method according to the invention, mention may be made of cotton; flax; vine; fruit or vegetable crops such as *Rosaceae* sp. (for instance pip fruit such as apples and pears, but also stone fruit such as apricots, almonds and peaches), *Ribesioidae* sp., *Juglandaceae* sp., *Betulaceae* sp., *Anacardiaceae* sp., *Fagaceae* sp., *Moraceae* sp., *Oleaceae* sp., *Actinidaceae* sp., *Lauraceae* sp., *Musaceae* sp. (for instance banana trees and plantins), *Rubiaceae* sp., *Theaceae* sp., *Sterculiceae* sp., *Rutaceae* sp. (for instance lemons, oranges and grapefruit); leguminous crops such as *Solanaceae* sp. (for instance tomatoes), *Liliaceae* sp., *Asteraceae* sp. (for instance lettuces), *Umbelliferae* sp., *Cruciferae* sp., *Chenopodiaceae* sp., *Cucurbitaceae* sp., *Papilionaceae* sp. (for instance peas), *Rosaceae* sp. (for instance strawberries); big crops such as *Graminae* sp. (for instance maize, lawn or cereals such as wheat, rice, barley and triticale), *Asteraceae* sp. (for instance sunflower), *Cruciferae* sp. (for instance colza), *Papilionaceae* sp. (for instance soja), *Solanaceae* sp. (for instance potatoes), *Chenopodiaceae* sp. (for instance beetroots); horticultural and forest crops; as well as genetically modified homologues of these crops. Among the plants or crops and the possible diseases of these plants or crops protected by the method according to the invention, mention may be made of:

wheat, as regards controlling the following seed diseases: fusaria (*Microdochium nivale* and *Fusarium roseum*), stinking smut (*Tilletia caries, Tilletia controversa* or *Tilletia* indica), septoria disease (*Septoria nodorum*) and loose smut;

wheat, as regards controlling the following diseases of the aerial parts of the plant: cereal eyespot (*Tapesia yallundae, Tapesia acuifomis*), take-all (*Gaeumannomyces graminis*), foot blight (*F. culmorum, F. graminearum*), black speck (*Rhizoctonia cerealis*), powdery mildew (*Erysiphe graminis* form a specie titici), rusts (*Puccinia striiformis* and *Puccinia recondita*) and septoria diseases (*Septoria tritici* and *Septoria nodorum*);

wheat and barley, as regards controlling bacterial and viral diseases, for example barley yellow mosaic;

barley, as regards controlling the following seed diseases: net blotch (*Pyrenophora graminea, Pyrenophora teres* and *Cochliobolus sativus*), loose smut (*Ustilago nuda*) and fusaria (*Microdochium nivale* and *Fusarium roseum*);

barley, as regards controlling the following diseases of the aerial parts of the plant: cereal eyespot (*Tapesia yallundae*), net blotch (*Pyrenophora teres* and *Cochliobolus sativus*), powdery mildew (*Erysiphe graminis forna specie hordei*), dwarf leaf rust (*Puccinia hordei*) and leaf blotch (*Rhynchosporium secalis*);

potato, as regards controlling tuber diseases (in particular *Helminthosporium solani, Phoma tuberosa, Rhizoctonia solani, Fusarum solani*), mildew (*Phytopthora infestans*) and certain viruses (virus Y);

potato, as regards controlling the following foliage diseases: early blight (*Alternaria solani*), mildew (*Phytophthora infestans*);

cotton, as regards controlling the following diseases of young plants grown from seeds: damping-off and collar rot (*Rhizoctonia solani, Fusarium oxysporum*) and black root rot (*Thielaviopsis basicola*);

protein yielding crops, for example peas, as regards controlling the following seed diseases: anthracnose (*Ascochyta pisi, Mycosphaerella pinodes*), fusaria (*Fusarium oxysporum*), grey mould (*Botrytis cinerea*) and mildew (*Peronospora pisi*);

oil-bearing crops, for example rape, as regards controlling the following seed diseases: *Phoma lingam, Alternaria brassicae* and *Sclerotfnia sclerotiorum;* corn, as regards controlling seed diseases: (*Rhizopus* sp., *Penicillium* sp., *Trichoderma* sp., *Aspergillus* sp., and *Gibberella fujikuroi*);

flax, as regards controlling the seed disease: *Alternadia linicola;* forest trees, as regards controlling damping-off (*Fusarium oxysporum, Rhizoctonia solani*);

rice, as regards controlling the following diseases of the aerial parts: blast disease (*Magnaporthe grisea*), bordered sheath spot (*Rhizoctonia solani*);

leguminous crops, as regards controlling the following diseases of seeds or of young plants grown from seeds: damping-off and collar rot (*Fusarium oxysporum, Fusarium roseum, Rhizoctonia solani, Pythium* sp.);

leguminous crops, as regards controlling the following diseases of the aerial parts: grey mould (*Botrytis* sp.), powdery mildews (in particular *Erysiphe cichoracearum, Sphaerotheca fuliginea* and *Leveillula taunca*), fusaria (*Fusarium oxysporum, Fusarium roseum*), leaf spot (*Cladosporium* sp.), alternaria leaf spot (*Alternaria* sp.), anthracnose (*Colletotrichum* sp.), septoria leaf spot (*Septoria* sp.), black speck (*Rhizoctonia solani*), mildews (for example *Bremia lactucae, Peronospora* sp., *Pseudoperonospora* sp., *Phytophthora* sp.);

fruit trees, as regards diseases of the aerial parts: monilia disease (*Monilia fructigenae, M. laxa*), scab (*Venturia inaequalis*), powdery mildew (*Podosphaera leucotricha*);

vine, as regards diseases of the foliage: in particular grey mould (*Botrytis cinerea*), powdery mildew (*Uncinula necator*), black rot (*Guignardia biwelli*) and mildew (*Plasmopara viticola*);

beetroot, as regards the following diseases of the aerial parts: *cercospora* blight (*Cercospora beticola*), powdery mildew (*Erysiphe beficola*), leaf spot (*Ramularia beticola*).

The fungicide composition according to the invention may also be used against fungal diseases liable to grow on or inside timber. The term "timber" means all types of species of wood, and all types of working of this wood intended for construction, for example solid wood, high-density wood, laminated wood, and plywood. The method for treating timber according to the invention mainly consists in contacting one or more compounds according to the invention, or a composition according to the invention; this includes for example direct application, spraying, dipping, injection or any other suitable means.

The dose of active compound usually applied in the method of treatment according to the invention is generally and advantageously from 10 to 800 g/ha, preferably from 50 to 300 g/ha for applications in foliar treatment. The dose of active substance applied is generally and advantageously from 2 to 200 g per 100 kg of seed, preferably from 3 to 150 g per 100 kg of seed in the case of seed treatment.

It is clearly understood that the doses indicated above are given as illustrative examples of the method according to the invention. A person skilled in the art will know how to adapt the application doses, notably according to the nature of the plant or crop to be treated.

The fungicide composition according to the invention may also be used in the treatment of genetically modified organisms with the compounds according to the invention or the agrochemical compositions according to the invention. Genetically modified plants are plants into genome of which a heterologous gene encoding a protein of interest has been stably integrated. The expression "heterologous gene encoding a protein of interest" essentially means genes which give the transformed plant new agronomic properties, or genes for improving the agronomic quality of the modified plant.

The compositions according to the invention may also be used for the preparation of composition useful to curatively or preventively treat human and animal fungal diseases such as, for example, mycoses, dermatoses, *trichophyton* diseases and candidiases or diseases caused by *Aspergillus* spp., for example *Aspergillus fumigatus*.

The various aspects of the invention will now be illustrated with reference to the following tables of compounds and examples. The following tables illustrate in a non-limiting manner examples of fungicide compounds according to the invention.

In the following examples, M+1 (or M−1) means the molecular ion peak, plus or minus 1 a.m.u. (atomic mass unit) respectively, as observed in mass spectroscopy and M (Apcl+) means the molecular ion peak as it was found via positive atmospheric pressure chemical ionisation in mass spectroscopy.

In the following examples, the logP values were determined in accordance with EEC Directive 79/B31 Annex V.A8 by HPLC (High Performance Liquid Chromatography) on a reversed-phase column (C 18), using 2 methods as described below:

Method A: Temperature: 43° C.; Mobile phases: 0.1% aqueous phosphoric acid, acetonitrile; linear gradient from 10% acetonitrile to 90% acetonitrile;

Method B: Temperature: 40° C.; Mobile phases: 0.1% aqueous formic acid and acetonitrile; linear gradient from 10% acetonitrile to 90% acetonitrile.

Calibration was carried out using unbranched alkan-2-ones (having 3 to 16 carbon atoms) with known logP values (determination of the logP values by the retention times using linear interpolation between two successive alkanones).

The lambda max values were determined in the maxima of the chromatographic signals using the UV spectra from 190 nm to 400 nm.

TABLE 1

| N° | A | L | LogP | LogP method | M + 1 |
|----|---|---|------|-------------|-------|
| 1 | 2,3-dibromofuran-5-yl | 2-substituted phenoxy | 3.58 | A | |
| 2 | 2-(trifluoromethyl)-5-methylfuran-3-yl | 2-substituted phenoxy | | | 408 |
| 3 | 2-methylfuran-3-yl | 3-substituted phenoxy | 3.27 | A | |

TABLE 1-continued

| N° | A | L | LogP | LogP method | M + 1 |
|---|---|---|---|---|---|
| 4 | 2-methylfuran-3-yl | 2-hydroxyphenyl | 2.77 | A | |
| 5 | 2,5-dimethylfuran-3-yl | 2,3-dihydroxyphenyl | 3.8 | B | |
| 6 | 2,5-dimethylfuran-3-yl | 2,3,4-trihydroxyphenyl | 4.4 | B | |
| 7 | 2,5-dimethylfuran-3-yl | 4-(4-bromophenoxy)phenyl | 4.9 | B | |
| 8 | 3-oxothiophen-2-yl | 4-methylphenyl | | | 356 |
| 9 | 3-oxothiophen-2-yl | 4-hydroxyphenyl | | | 376 |
| 10 | 3-oxothiophen-2-yl | 2,4-dihydroxyphenyl | | | 410 |

TABLE 1-continued

| N° | A | L | LogP | LogP method | M + 1 |
|----|---|---|------|-------------|-------|
| 11 | 3-methylthiophen-2-yl | 2,3-dihydroxyphenyl | | | 424 |
| 12 | 3-methylthiophen-2-yl | 4-phenoxyphenyl | | | 414 |
| 13 | 3-methylthiophen-2-yl | 3-hydroxyphenyl | 3.64 | A | |
| 14 | 3-methylthiophen-2-yl | 2-hydroxyphenyl | 3.12 | A | |
| 15 | 3,4-dibromothiophen-2-yl | 2-hydroxyphenyl | 4.07 | A | |
| 16 | 3-chloro-4,5-dihydroxythiophen-2-yl | 4-methylphenyl | | | 424 |
| 17 | 3-chloro-4,5-dihydroxythiophen-2-yl | 4-hydroxyphenyl | | | 444 |

TABLE 1-continued

| N° | A | L | LogP | LogP method | M + 1 |
|---|---|---|---|---|---|
| 18 | thiophene | dihydroxyphenyl | | | 478 |
| 19 | iodothiophene | dihydroxyphenyl | 3.8 | B | |
| 20 | dihydroxythiophene | hydroxyphenyl | | | 409 |
| 21 | iodothiophene | phenoxyphenyl | 4.3 | B | |
| 22 | iodothiophene | (4-bromophenoxy)phenyl | 4.9 | B | |
| 23 | iodothiophene | trihydroxyphenyl | | | 535 |

TABLE 1-continued

| N° | A | L | LogP | LogP method | M + 1 |
|----|---|---|------|-------------|-------|
| 24 | (2-methoxy-thiophen-3-yl, 5-oxo) | 2-hydroxyphenyl | | | 405 |
| 25 | 4-methoxy-thiophen-3-yl | 2,3-dihydroxyphenyl | 3.3 | B | |
| 26 | 4-methoxy-thiophen-3-yl | 4-phenoxyphenyl | 3.9 | B | |
| 27 | 4-methoxy-thiophen-3-yl | 2,3,4-trihydroxyphenyl | 3.9 | B | |
| 28 | 4-methoxy-thiophen-3-yl | 4-(4-bromophenoxy)phenyl | 4.4 | B | |

TABLE 1-continued
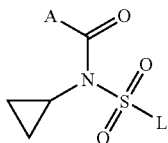
| N° | A | L | LogP | LogP method | M + 1 |
|----|---|---|------|-------------|-------|
| 29 | 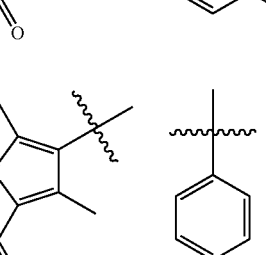 | 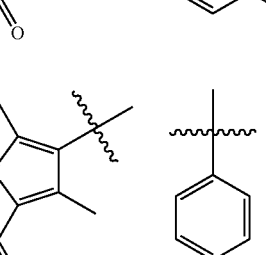 | 3.46 | A | |
| 30 | 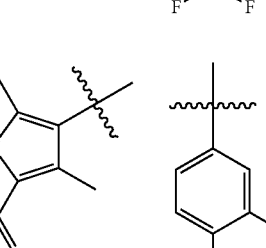 | 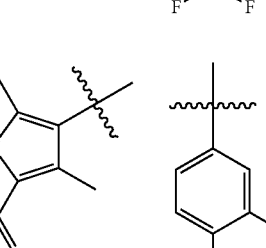 | 3.72 | A | |
| 31 | 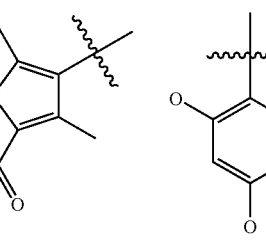 | 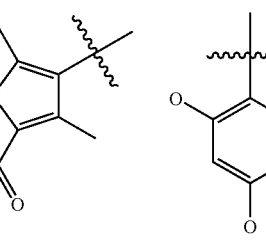 | 4.08 | A | |
| 32 | 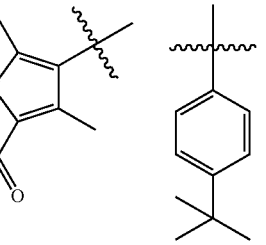 | 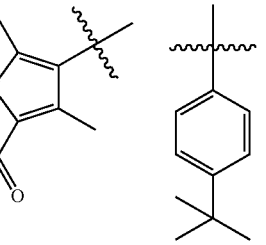 | 3.63 | A | |
| 33 | 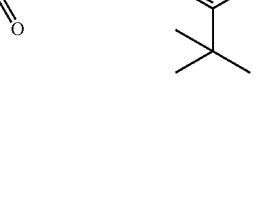 | 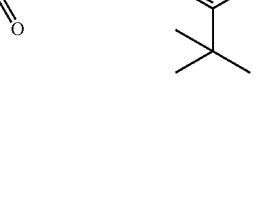 | 4.13 | A | |

TABLE 1-continued

| N° | A | L | LogP | LogP method | M + 1 |
|---|---|---|---|---|---|
| 34 | ethyl 3,4-dimethyl-1H-pyrrole-2-carboxylate (attached at 4-position) | 2,3-dihydroxyphenyl | 3.5 | B | |
| 35 | 1-methyl-4-(trifluoromethyl)-1H-pyrrol-3-yl | 2-hydroxyphenyl | | | 407 |
| 36 | 1-methyl-4-(trifluoromethyl)-1H-pyrrol-3-yl | 2,3-dihydroxyphenyl | 3.3 | B | |
| 37 | 1-methyl-4-(trifluoromethyl)-1H-pyrrol-3-yl | 2,3,4-trihydroxyphenyl | 3.9 | B | |
| 38 | 1-methyl-4-(trifluoromethyl)-1H-pyrrol-3-yl | 4-phenoxyphenyl | 4.0 | B | |

TABLE 1-continued

| N° | A | L | LogP | LogP method | M + 1 |
|---|---|---|---|---|---|
| 39 | 1-methyl-4-(trifluoromethyl)pyrrol-3-yl | 4-(4-bromophenoxy)phenyl | 4.5 | B | |
| 40 | 2-methyl-4-(trifluoromethyl)oxazol-5-yl | 2,4-dihydroxyphenyl | | | 442 |
| 41 | 2-methyl-4-(trifluoromethyl)oxazol-5-yl | 2-hydroxyphenyl | | | 409 |
| 42 | 2-methyl-4-(trifluoromethyl)oxazol-5-yl | 2,3-dihydroxyphenyl | | | 442 |
| 43 | 2-methyl-4-(trifluoromethyl)oxazol-5-yl | 2,3,4-trihydroxyphenyl | | | 476 |
| 44 | 2,5-dimethyloxazol-4-yl | 2,3,4-trihydroxyphenyl | | | 423 |

TABLE 1-continued

| N° | A | L | LogP | LogP method | M + 1 |
|---|---|---|---|---|---|
| 45 | 2,5-dimethyloxazol-4-yl | 4-phenoxyphenyl | | | 413 |
| 46 | 2,5-dimethyloxazol-4-yl | 4-benzylphenyl | | | 411 |
| 47 | 2,5-dimethyloxazol-4-yl | 4-(3-trifluoromethylphenoxy)phenyl | | | 481 |
| 48 | 2-methyl-5-trifluoromethyloxazol-4-yl | 2,3-dihydroxyphenyl | | | 477 |
| 49 | 2-methyl-5-trifluoromethyloxazol-4-yl | 4-phenoxyphenyl | | | 467 |
| 50 | 2-phenyl-4-methylthiazol-5-yl | 2-hydroxyphenyl | | | 433 |

TABLE 1-continued

| N° | A | L | LogP | LogP method | M + 1 |
|---|---|---|---|---|---|
| 51 | 2-Cl-thiazol-5-yl | 2-hydroxyphenyl | | | 376 |
| 52 | 4-methyl-2-oxo-thiazol-5-yl | 2,3,4-trihydroxyphenyl | | | |
| 53 | 4-methyl-2-oxo-thiazol-5-yl | 2,3-dihydroxyphenyl | | | |
| 54 | 2-Br-4-methyl-thiazol-5-yl | 2,3,4-trihydroxyphenyl | | | 502 |
| 55 | 2-Br-4-methyl-thiazol-5-yl | 2,3-dihydroxyphenyl | | | 468 |
| 56 | 2-Br-4-methyl-thiazol-5-yl | 4-phenoxyphenyl | | | 492 |

TABLE 1-continued

| N° | A | L | LogP | LogP method | M + 1 |
|---|---|---|---|---|---|
| 57 | 2-bromo-4-methylthiazol-5-yl | 4-(4-bromophenoxy)phenyl | | | 570 |
| 58 | 4-(difluoromethyl)-2-methylthiazol-5-yl | 2-hydroxyphenyl | | | 407 |
| 59 | 2-methyl-4-(trifluoromethyl)thiazol-5-yl | 2-hydroxyphenyl | 3.2 | A | |
| 60 | 2-methylthiazol-5-yl | 3-hydroxyphenyl | 2.8 | A | |
| 61 | 2-methylthiazol-5-yl | 4-(trifluoromethyl)phenyl | 3.1 | A | |

TABLE 1-continued
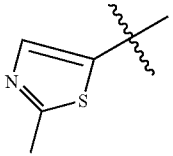
| N° | A | L | LogP | LogP method | M + 1 |
|----|---|---|------|-------------|-------|
| 62 | 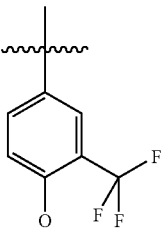 | 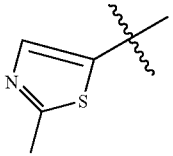 | 3.46 | A | |
| 63 | 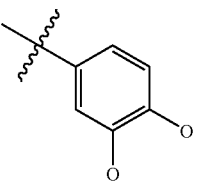 | 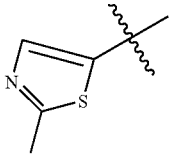 | 3.33 | A | |
| 64 | 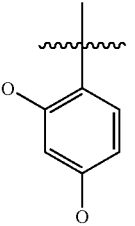 | 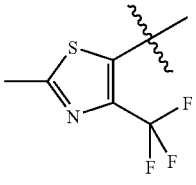 | 2.91 | A | |
| 65 | 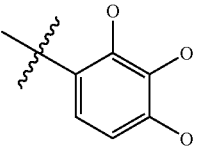 | 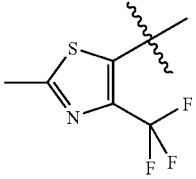 | | | 493 |
| 66 | 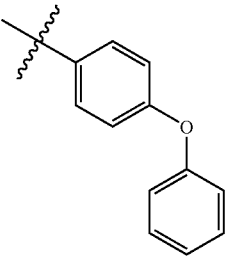 | 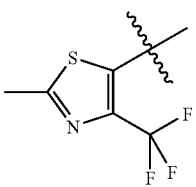 | 4.4 | B | |
| 67 | 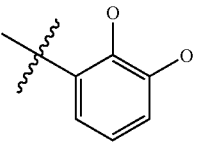 | | | | 459 |

TABLE 1-continued

| N° | A | L | LogP | LogP method | M + 1 |
|---|---|---|---|---|---|
| 68 | 2-methylthiazol-4-yl | 4-(trifluoromethyl)phenyl | 3.18 | A | |
| 69 | 2-methylthiazol-4-yl | 4-hydroxy-3-(trifluoromethyl)phenyl | 3.63 | A | |
| 70 | 2-methylthiazol-4-yl | 3,4-dihydroxyphenyl | 3.46 | A | |
| 71 | 2-methylthiazol-4-yl | 2,4-dihydroxyphenyl | 3.03 | A | |
| 72 | 2-methylthiazol-4-yl | 4-tert-butylphenyl | 3.59 | A | |
| 73 | 1,5-dimethyl-1H-pyrazol-3-yl | 2-hydroxyphenyl | | | 354 |

TABLE 1-continued
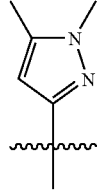
| N° | A | L | LogP | LogP method | M + 1 |
|---|---|---|---|---|---|
| 74 | 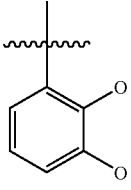 | 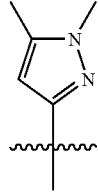 | 2.7 | B | |
| 75 | 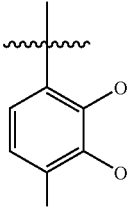 | 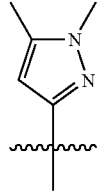 | 3.3 | B | |
| 76 | 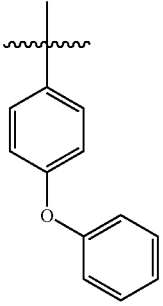 | 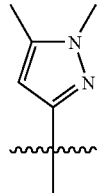 | 3.4 | B | |
| 77 | 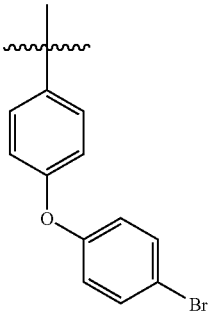 | 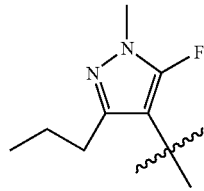 | 4.0 | B | |
| 78 | 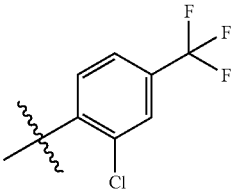 | | | | 468 |

TABLE 1-continued

| N° | A | L | LogP | LogP method | M + 1 |
|---|---|---|---|---|---|
| 79 | | | | | 458 |
| 80 | | | | | 517 |
| 81 | | | | | 489 |
| 82 | | | | | 547 |
| 83 | | | | | 533 |
| 84 | | | | | 531 |

TABLE 1-continued

| N° | A | L | LogP | LogP method | M + 1 |
|----|---|---|------|-------------|-------|
| 85 | | | | | 503 |
| 86 | | | | | 440 |
| 87 | | | | | 525 |
| 88 | | | | | 509 |
| 89 | | | | | 543 |
| 90 | | | | | 544 |

TABLE 1-continued

| N° | A | L | LogP | LogP method | M + 1 |
|----|---|---|------|-------------|-------|
| 91 | | | | | 510 |
| 92 | | | | | 534 |
| 93 | | | 3.6 | B | |
| 94 | | | | | 468 |
| 95 | | | 3.1 | B | |
| 96 | | | 3.8 | B | |

TABLE 1-continued

| N° | A | L | LogP | LogP method | M + 1 |
|---|---|---|---|---|---|
| 97 | 3-isopropyl-5-fluoro-1-methyl-pyrazol-4-yl (with methyl) | 2-hydroxy-5-trifluoromethyl-phenyl | 4.0 | B | |
| 98 | 3-isopropyl-5-fluoro-1-methyl-pyrazol-4-yl (with methyl) | 2-trifluoromethyl-phenyl | 3.4 | B | |
| 99 | 3-isopropyl-5-fluoro-1-methyl-pyrazol-4-yl (with methyl) | 4-phenoxy-phenyl | | | 458 |
| 100 | 5-fluoro-1-methyl-3-phenyl-pyrazol-4-yl (with methyl) | 2,3-dimethoxy-phenyl | 4.3 | B | |
| 101 | 5-fluoro-1-methyl-3-phenyl-pyrazol-4-yl (with methyl) | 2,3-methylenedioxy-phenyl | 3.7 | B | |

TABLE 1-continued

| N° | A | L | LogP | LogP method | M + 1 |
|----|---|---|------|-------------|-------|
| 102 | | | | | 434 |
| 103 | | | 2.8 | B | |
| 104 | | | 3.2 | B | |
| 105 | | | 3.4 | B | |
| 106 | | | 3.0 | B | |
| 107 | | | 3.8 | B | |

TABLE 1-continued

| N° | A | L | LogP | LogP method | M + 1 |
|---|---|---|---|---|---|
| 108 | (1-methyl-5-fluoro-3-trifluoromethyl-pyrazol-4-yl) | (2,3-dihydroxyphenyl) | 4.1 | B | |
| 109 | (1-methyl-5-fluoro-3-methyl-pyrazol-4-yl) | (4,5-difluoro-2-hydroxyphenyl) | | | 408 |
| 110 | (1-methyl-3-methoxy-5-fluoro-pyrazol-4-yl) | (2,3-dihydroxyphenyl) | | | 455 |
| 111 | (1-methyl-5-fluoro-3-methyl-pyrazol-4-yl) | (3-phenoxyphenyl) | | | 430 |
| 112 | (1-methyl-5-fluoro-3-trifluoromethyl-pyrazol-4-yl) | (3-hydroxyphenyl) | | | 426 |
| 113 | (1-methyl-5-fluoro-pyrazol-4-yl) | (2-hydroxyphenyl) | | | 386 |

TABLE 1-continued

| N° | A | L | LogP | LogP method | M + 1 |
|---|---|---|---|---|---|
| 114 | | | | | 426 |
| 115 | | | | | 459 |
| 116 | | | | | 386 |
| 117 | | | | | 386 |
| 118 | | | | | 420 |
| 119 | | | 2.8 | B | |

TABLE 1-continued

| N° | A | L | LogP | LogP method | M + 1 |
|---|---|---|---|---|---|
| 120 | | | 3.4 | B | |
| 121 | | | 3.5 | B | |
| 122 | | | 4.1 | B | |
| 123 | | | | | 480 |
| 124 | | | | | 400 |

TABLE 1-continued
| N° | A | L | LogP | LogP method | M + 1 |
|---|---|---|---|---|---|
| 125 | 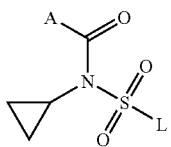 | 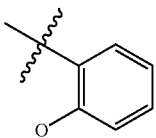 | | | 374 |
| 126 | 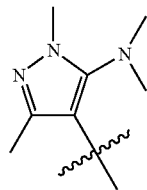 | 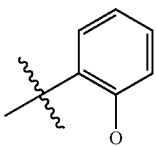 | | | 397 |
| 127 | 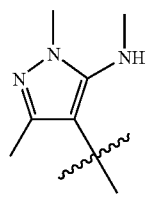 | 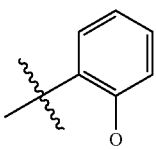 | | | 383 |
| 128 | 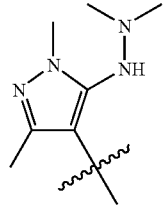 | 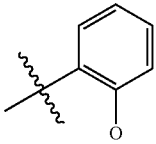 | | | 412 |
| 129 | 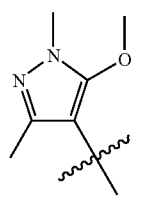 | 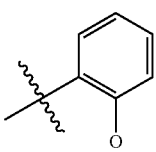 | | | 384 |
| 130 | 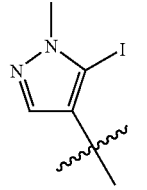 | 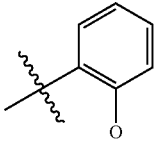 | | | 465 |
| 131 | 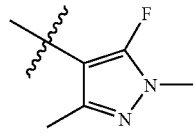 | 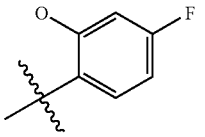 | | | 390 |

TABLE 1-continued
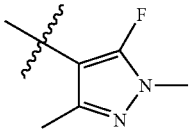
| N° | A | L | LogP | LogP method | M + 1 |
|---|---|---|---|---|---|
| 132 | 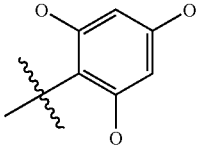 | 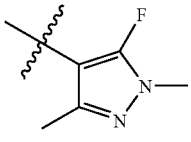 | | | 439 |
| 133 | 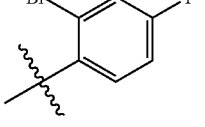 | 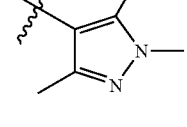 | | | 433 |
| 134 | 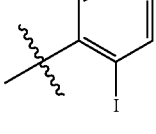 | 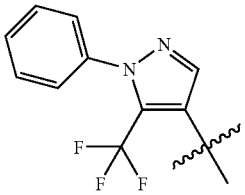 | | | 463 |
| 135 | 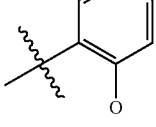 | 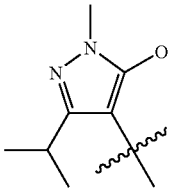 | | | 470 |
| 136 | 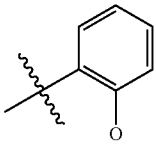 | 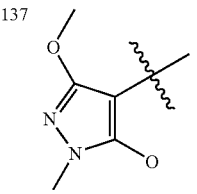 | | | 416 |
| 137 | 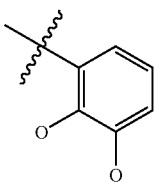 | 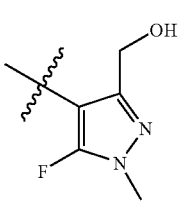 | | | 481 |
| 138 | 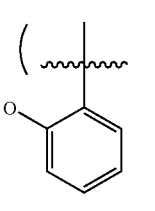 | | | | 388 |

TABLE 1-continued

| N° | A | L | LogP | LogP method | M + 1 |
|---|---|---|---|---|---|
| 139 | 3-methyl-5-fluoro-1H-pyrazol-4-yl | 2-hydroxyphenyl | | | 358 |
| 140 | 3-methoxy-1-methyl-1H-pyrazol-4-yl | 2,3-dihydroxyphenyl | | | 404 |
| 141 | 3-methoxy-1-methyl-1H-pyrazol-4-yl | 2,4-dihydroxyphenyl | | | 404 |
| 142 | 3-methoxy-1-methyl-1H-pyrazol-4-yl | 2,3,4-trihydroxyphenyl | | | 437 |
| 143 | 3-methoxy-1-methyl-1H-pyrazol-4-yl | 4-phenoxyphenyl | | | 428 |
| 144 | 3-methoxy-1-methyl-5-bromo-1H-pyrazol-4-yl | 2,4-dihydroxyphenyl | | | 481 |

TABLE 1-continued

| N° | A | L | LogP | LogP method | M + 1 |
|----|---|---|------|-------------|-------|
| 145 | | | | | 515 |
| 146 | | | | | 506 |
| 147 | | | | | 447 |
| 148 | | | | | 481 |
| 149 | | | | | 497 |
| 150 | | | | | 430 |

TABLE 1-continued
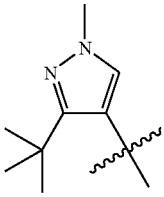
| N° | A | L | LogP | LogP method | M + 1 |
|---|---|---|---|---|---|
| 151 | 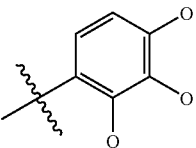 | 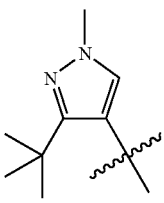 | | | 464 |
| 152 | 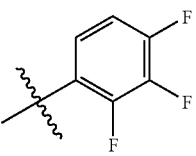 | 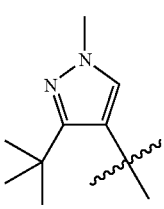 | | | 416 |
| 153 | 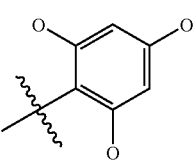 | 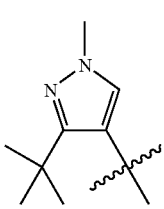 | | | 464 |
| 154 | 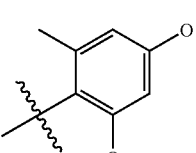 | 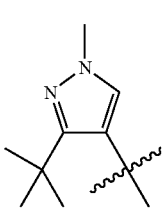 | | | 444 |
| 155 | 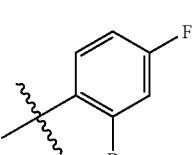 | 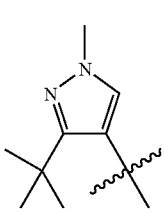 | | | 458 |
| 156 | 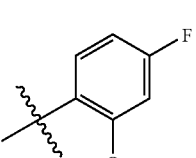 | | | | 414 |

TABLE 1-continued

| N° | A | L | LogP | LogP method | M + 1 |
|---|---|---|---|---|---|
| 157 | | | | | 454 |
| 158 | | | | | 420 |
| 159 | | | | | 453 |
| 160 | | | | | 420 |
| 161 | | | | | 453 |
| 162 | | | | | 386 |

TABLE 1-continued

| N° | A | L | LogP | LogP method | M + 1 |
|---|---|---|---|---|---|
| 163 | 1-methyl-3-ethyl-5-fluoro-pyrazol-4-yl | 2-hydroxy-4-(trifluoromethyl)phenyl | | | 454 |
| 164 | 1-ethyl-3-methyl-5-fluoro-pyrazol-4-yl | 2-hydroxy-4-(trifluoromethyl)phenyl | | | 454 |
| 165 | 1-ethyl-3-methyl-5-fluoro-pyrazol-4-yl | naphthalen-1-yl | | | 402 |
| 166 | 1-ethyl-3-methyl-5-fluoro-pyrazol-4-yl | 4-phenoxyphenyl | | | 444 |
| 167 | 1-ethyl-3-methyl-5-fluoro-pyrazol-4-yl | 2,6-dihydroxy-4-(trifluoromethyl)phenyl | | | 488 |
| 168 | 1-ethyl-3-methyl-5-fluoro-pyrazol-4-yl | 3-bromo-2,5-dihydroxythiophen-4-yl | | | 504 |

TABLE 1-continued

| N° | A | L | LogP | LogP method | M + 1 |
|---|---|---|---|---|---|
| 169 | | | | | 421 |
| 170 | | | | | 416 |
| 171 | | | | | 390 |
| 172 | | | | | 394 |
| 173 | | | | | 475 |
| 174 | | | | | 452 |

TABLE 1-continued

| N° | A | L | LogP | LogP method | M + 1 |
|---|---|---|---|---|---|
| 175 | pyrazole (3-methyl, 1-methyl, 5-F) | 3-methylphenyl | 2.61 | A | |
| 176 | pyrazole (5-F, 1-methyl, 3-methyl) | 3-methoxyphenyl | 2.82 | A | |
| 177 | pyrazole (5-F, 1-methyl, 3-methyl) | 3-(trifluoromethyl)phenyl | 3.03 | A | |
| 178 | pyrazole (5-F, 1-methyl, 3-methyl) | 3,4-dimethoxyphenyl | 3.35 | A | |
| 179 | pyrazole (5-F, 1-methyl, 3-methyl) | 4-fluorophenyl | 2.46 | A | |
| 180 | pyrazole (5-F, 1-methyl, 3-methyl) | 2-hydroxyphenyl | 2.34 | A | |
| 181 | pyrazole (5-F, 1-methyl, 3-methyl) | phenyl | 2.28 | A | |
| 182 | pyrazole (5-F, 1-methyl, 3-methyl) | 2-methoxyphenyl | 2.06 | A | |

TABLE 1-continued

| N° | A | L | LogP | LogP method | M + 1 |
|----|---|---|------|-------------|-------|
| 183 | 5-fluoro-1,3-dimethyl-1H-pyrazol-4-yl | 4-methylphenyl | 2.59 | A | |
| 184 | 5-fluoro-1,3-dimethyl-1H-pyrazol-4-yl | 4-methoxyphenyl | 2.35 | A | |
| 185 | 5-fluoro-1,3-dimethyl-1H-pyrazol-4-yl | 4-nitrophenyl | 2.54 | A | |
| 186 | 5-fluoro-1,3-dimethyl-1H-pyrazol-4-yl | 2,4-dihydroxyphenyl | 2.94 | A | |
| 187 | 5-fluoro-1,3-dimethyl-1H-pyrazol-4-yl | 4-phenoxyphenyl | 3.42 | A | |
| 188 | 5-fluoro-1,3-dimethyl-1H-pyrazol-4-yl | 4-(trifluoromethyl)phenyl | 3.1 | A | |
| 189 | 5-fluoro-1,3-dimethyl-1H-pyrazol-4-yl | 2,4,6-trimethylphenyl | 3.05 | A | |
| 190 | 5-fluoro-1,3-dimethyl-1H-pyrazol-4-yl | 4-hydroxyphenyl | 2.83 | A | |

TABLE 1-continued

| N° | A | L | LogP | LogP method | M + 1 |
|---|---|---|---|---|---|
| 191 | 4-(5-fluoro-1,3-dimethyl-pyrazol-4-yl) | 2,5-dihydroxyphenyl | 2.91 | A | |
| 192 | 4-(5-fluoro-1,3-dimethyl-pyrazol-4-yl) | 4-tert-butylphenyl | 3.55 | A | |
| 193 | 4-(5-fluoro-1,3-dimethyl-pyrazol-4-yl) | 3,5-dihydroxyphenyl | 3.48 | A | |
| 194 | 4-(5-fluoro-1,3-dimethyl-pyrazol-4-yl) | 4-hydroxy-3-trifluoromethylphenyl | 3.5 | A | |
| 195 | 4-(5-fluoro-1,3-dimethyl-pyrazol-4-yl) | 3-nitrophenyl | 2.48 | A | |
| 196 | 4-(5-fluoro-1,3-dimethyl-pyrazol-4-yl) isomer | 2-methylphenyl | 2.43 | A | |
| 197 | 4-(1,3-dimethyl-pyrazol-4-yl) | 2-hydroxyphenyl | 1.95 | A | |

TABLE 1-continued
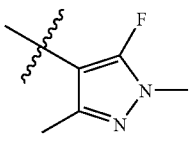
| N° | A | L | LogP | LogP method | M + 1 |
|----|---|---|------|-------------|-------|
| 198 | 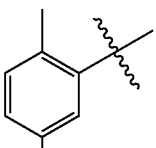 | 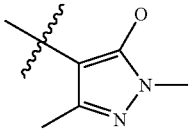 | 2.78 | A | |
| 199 | 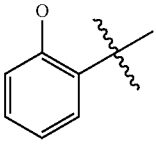 | 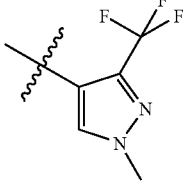 | 2.58 | A | |
| 200 | 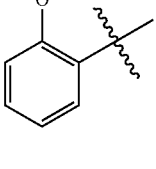 | 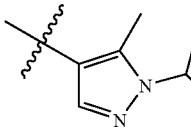 | 2.71 | A | |
| 201 | 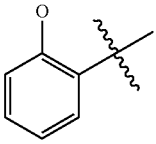 | 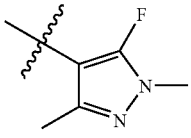 | 2.97 | A | |
| 202 | 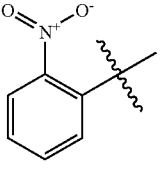 | 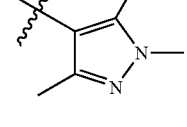 | 2.25 | A | |
| 203 | 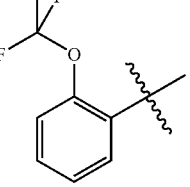 | 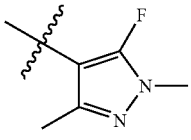 | 2.75 | A | |
| 204 | 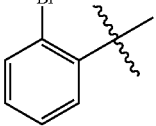 | 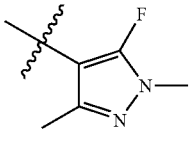 | 2.37 | A | |
| 205 | 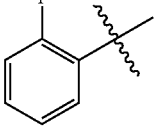 | | 2.25 | A | |

TABLE 1-continued
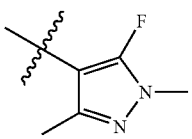
| N° | A | L | LogP | LogP method | M + 1 |
|---|---|---|---|---|---|
| 206 | 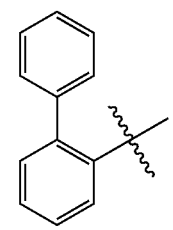 | 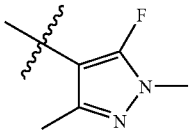 | 2.96 | A | |
| 207 | 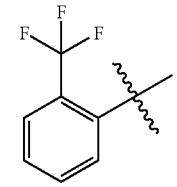 | 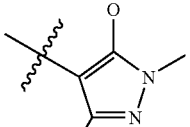 | 2.6 | A | |
| 208 | 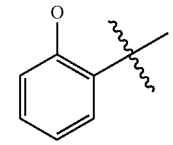 | 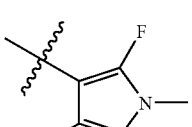 | 3.27 | A | |
| 209 | 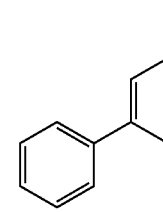 | 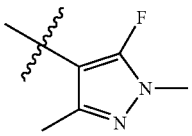 | 3.39 | A | |
| 210 | 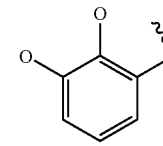 | 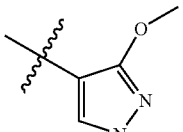 | 2.77 | A | |
| 211 | 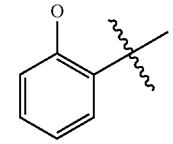 | 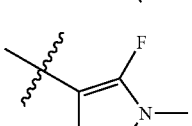 | 1.94 | A | |
| 212 | 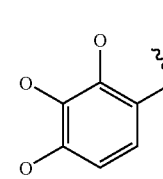 | | 3.35 | A | |

TABLE 1-continued

| N° | A | L | LogP | LogP method | M + 1 |
|---|---|---|---|---|---|
| 213 | 4-(5-fluoro-3-methyl-1-methylpyrazolyl) | 2-(trifluoromethyl)-phenoxy | 3.19 | A | |
| 214 | 4-(3-methyl-1-methylpyrazolyl) | phenoxy | 2.31 | A | |
| 215 | 4-(3,5-dimethyl-1-methylpyrazolyl) | phenoxy | 2.17 | A | |
| 216 | 4-(5-fluoro-3-methyl-1-methylpyrazolyl) | 2-cyanophenyl | 2.07 | A | |
| 217 | 4-(5-fluoro-3-methyl-1-methylpyrazolyl) | 2,6-difluorophenyl | 2.25 | A | |
| 218 | 4-(5-fluoro-3-methyl-1-methylpyrazolyl) | 2,6-dioxyphenyl | 2.52 | A | |
| 219 | 4-(5-fluoro-3-methyl-1-methylpyrazolyl) | 4-(trifluoromethyl)-2,6-dioxyphenyl | | | 474 |

TABLE 1-continued

| N° | A | L | LogP | LogP method | M + 1 |
|---|---|---|---|---|---|
| 220 | 1-methyl-5-fluoro-3-propyl-pyrazol-4-yl | 4-[3-hydroxy-5-(trifluoromethyl)pyridin-2-yloxy]phenyl | | | 561 |
| 221 | 1-methyl-3-(difluoromethyl)-pyrazol-4-yl | 2,3-dimethoxyphenyl | 2.9 | B | |
| 222 | 1,3-dimethyl-5-cyano-pyrazol-4-yl | 2-methoxyphenyl | | | 379 |
| 223 | 1-methyl-3-cyclopropyl-5-oxo-pyrazol-4-yl | 2,3,4-trimethoxyphenyl | 4.2 | B | |
| 224 | 1-methyl-5-fluoro-3-cyclopropyl-pyrazol-4-yl | 2,3,4-trimethoxyphenyl | 3.9 | B | |
| 225 | 1-methyl-5-chloro-3-cyclopropyl-pyrazol-4-yl | 2,3-dimethoxyphenyl | 4.7 | B | |

TABLE 1-continued

| N° | A | L | LogP | LogP method | M + 1 |
|---|---|---|---|---|---|
| 226 | | | | | 456 |
| 227 | | | | | 432 |
| 228 | | | 3.9 | B | |
| 229 | | | 3.6 | B | |
| 230 | | | 3.2 | B | |
| 231 | | | | | 456 |

TABLE 1-continued
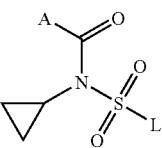
| N° | A | L | LogP | LogP method | M + 1 |
|---|---|---|---|---|---|
| 232 | 1-methyl-3-methoxy-pyrazol-4-yl | 4-bromophenyl | | | 414 |
| 233 | 1-methyl-3-methoxy-pyrazol-4-yl | 3'-(trimethylsilyl)biphenyl-4-yl | | | 484 |
| 234 | 1-methyl-3-methoxy-pyrazol-4-yl | 3'-(trifluoromethyl)biphenyl-4-yl | | | 480 |
| 235 | 1-methyl-3-ethoxy-pyrazol-4-yl | 4-phenoxyphenyl | | | 442 |
| 236 | 1-methyl-3-isopropoxy-pyrazol-4-yl | 4-phenoxyphenyl | | | 456 |

TABLE 1-continued

| N° | A | L | LogP | LogP method | M + 1 |
|---|---|---|---|---|---|
| 237 | | | | | 500 |
| 238 | | | | | 452 |
| 239 | | | | | 466 |
| 240 | | | | | 524 |
| 241 | | | | | 534 |
| 242 | | | | | 392 |

TABLE 1-continued

| N° | A | L | LogP | LogP method | M + 1 |
|---|---|---|---|---|---|
| 243 | (1-methyl-3-methoxy-pyrazol-4-yl) | 4'-(benzyloxy)biphenyl-4-yl | | | 518 |
| 244 | (1-methyl-3-difluoromethyl-pyrazol-4-yl) | 2,3-methylenedioxy-phenyl type (2,3-dihydroxy) | | | 458 |
| 245 | (1-methyl-3-trifluoromethyl-pyrazol-4-yl) | 4-phenoxyphenyl | | | 466 |
| 246 | (1-methyl-3-trifluoromethyl-pyrazol-4-yl) | 2,3-methylenedioxy-phenyl | | | 476 |
| 247 | (1-methyl-3-trifluoromethyl-pyrazol-4-yl) | 4-bromophenyl | | | 452 |
| 248 | (1-methyl-3-methoxy-pyrazol-4-yl) | 4-(prop-2-ynyloxy)phenyl | | | 390 |

TABLE 1-continued

| N° | A | L | LogP | LogP method | M + 1 |
|---|---|---|---|---|---|
| 249 | 3-(difluoromethyl)-1-methyl-1H-pyrazol-4-yl | 4-phenoxyphenyl | | | 448 |
| 250 | 3-(difluoromethyl)-1-methyl-1H-pyrazol-4-yl | 4-bromophenyl | | | 434 |
| 251 | 3-(difluoromethyl)-1-methyl-1H-pyrazol-4-yl | 4-benzylphenyl | | | 446 |
| 252 | 3-(difluoromethyl)-1-methyl-1H-pyrazol-4-yl | 3-phenoxyphenyl | | | 448 |
| 253 | 3-(difluoromethyl)-1-methyl-1H-pyrazol-4-yl | 4-(pyridin-4-yloxy)phenyl | | | 449 |
| 254 | 3-(difluoromethyl)-1-methyl-1H-pyrazol-4-yl | 4-(3-methylphenoxy)phenyl | | | 462 |

TABLE 1-continued
| N° | A | L | LogP | LogP method | M + 1 |
|---|---|---|---|---|---|
| 255 | 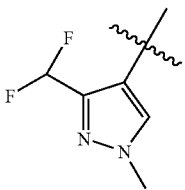 | 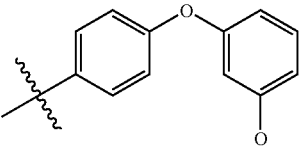 | | | 482 |
| 256 | 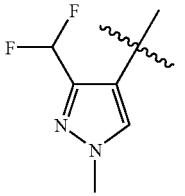 | 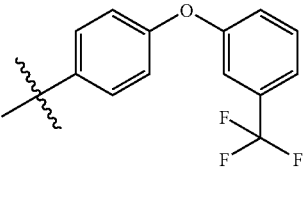 | | | 516 |
| 257 | 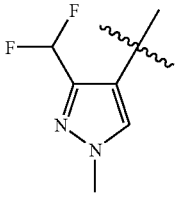 | 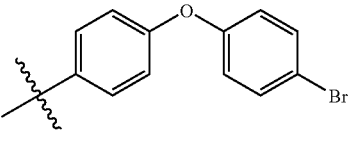 | | | 526 |
| 258 | 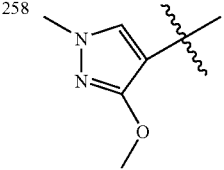 | 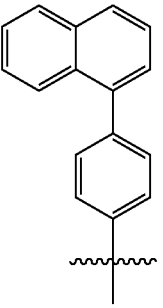 | | | 462 |
| 259 | 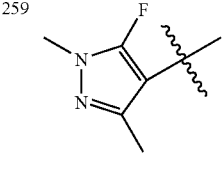 | 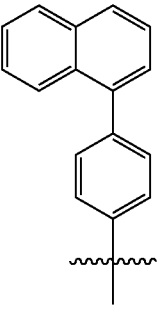 | | | 464 |

TABLE 1-continued
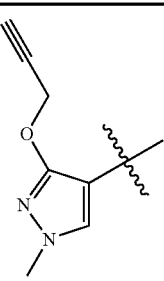
| N° | A | L | LogP | LogP method | M + 1 |
|---|---|---|---|---|---|
| 260 | 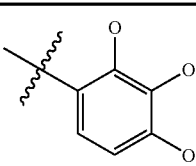 | 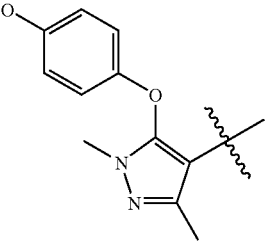 | | | 462 |
| 261 | 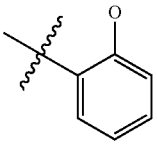 | 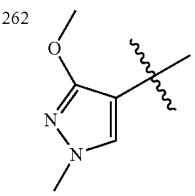 | 3.6 | B | |
| 262 | 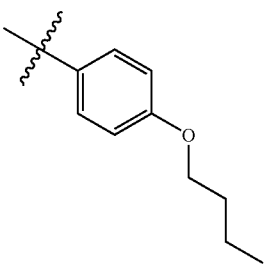 | 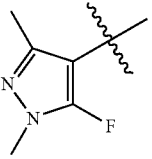 | | | 408 |
| 263 | 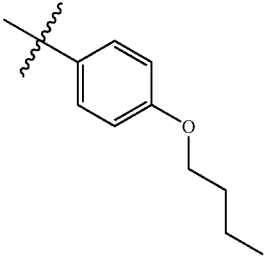 | 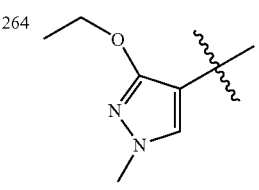 | | | 410 |
| 264 | 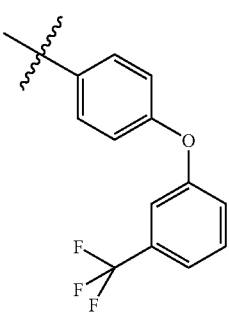 |  | | | 510 |

TABLE 1-continued
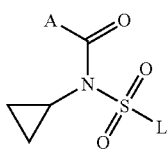
| N° | A | L | LogP | LogP method | M + 1 |
|---|---|---|---|---|---|
| 265 | | | | | 428 |
| 266 | | | | | 444 |
| 267 | | | | | 478 |
| 268 | | | | | 496 |
| 269 | | | | | 506 |
| 270 | | | | | 462 |

TABLE 1-continued

| N° | A | L | LogP | LogP method | M + 1 |
|---|---|---|---|---|---|
| 271 | 3-methoxy-1-methylpyrazol-4-yl | 4-(3-(trifluoromethyl)phenoxy)phenyl | | | 496 |
| 272 | 1-methyl-3-methoxypyrazol-4-yl | 4-((3,4-dioxophenyl)thio)phenyl | | | 512 |
| 273 | 3-methoxy-1-methylpyrazol-4-yl | 2-phenoxyphenyl | | | 428 |
| 274 | 3-methoxy-1-methylpyrazol-4-yl | 3-(2-oxophenoxy)phenyl | | | 462 |
| 275 | 3-methoxy-1-methylpyrazol-4-yl | 4-(3-chloro-5-oxophenoxy)phenyl | | | 496 |
| 276 | 3-methoxy-1-methylpyrazol-4-yl | 4-(2-oxophenoxy)phenyl | | | 462 |

TABLE 1-continued
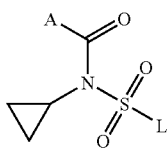
| N° | A | L | LogP | LogP method | M + 1 |
|---|---|---|---|---|---|
| 277 | | | | | 496 |
| 278 | | | 3.2 | B | |
| 279 | | | | | 490 |
| 280 | | | 3.8 | B | |
| 281 | | | | | 456 |

TABLE 1-continued
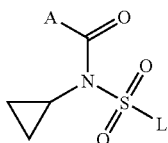
| N° | A | L | LogP | LogP method | M + 1 |
|---|---|---|---|---|---|
| 282 | 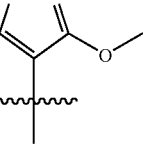 | 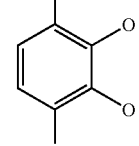 | 3.8 | B | |
| 283 |  | 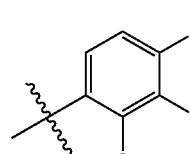 | | | 466 |
| 284 | 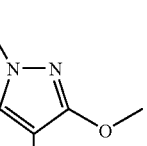 | 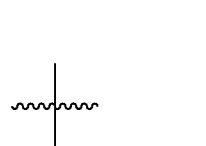 | 4.3 | B | |
| 285 |  | 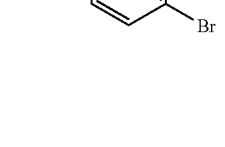 | 2.7 | B | |

TABLE 1-continued

| N° | A | L | LogP | LogP method | M + 1 |
|---|---|---|---|---|---|
| 286 | | | 3.0 | B | |
| 287 | | | 3.4 | B | |
| 288 | | | 3.6 | B | |
| 289 | | | 4.0 | B | |

TABLE 1-continued

| N° | A | L | LogP | LogP method | M + 1 |
|---|---|---|---|---|---|
| 290 | propoxy-methylpyrazole | 2-bromo-4-phenoxyphenyl | 4.1 | B | |
| 291 | propoxy-methylpyrazole | 2-bromo-4-(2-hydroxyphenoxy)phenyl | 4.2 | B | |
| 292 | propoxy-methylpyrazole | 2-bromo-4-(3-dimethylaminophenoxy)phenyl | 4.4 | B | |
| 293 | propoxy-methylpyrazole | 2-bromo-4-(4-methylphenoxy)phenyl | 4.5 | B | |

TABLE 1-continued
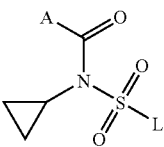
| N° | A | L | LogP | LogP method | M + 1 |
|---|---|---|---|---|---|
| 294 | | | 4.5 | B | |
| 295 | | | 4.5 | B | |
| 296 | | | 4.5 | B | |
| 297 | | | 4.5 | B | |

TABLE 1-continued
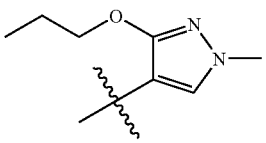
| N° | A | L | LogP | LogP method | M + 1 |
|---|---|---|---|---|---|
| 298 | 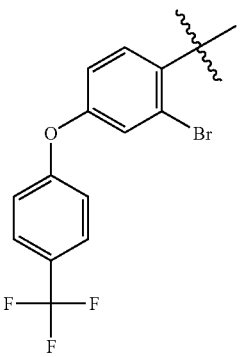 | 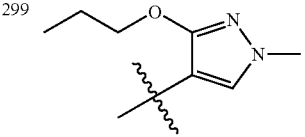 | 4.6 | B | |
| 299 | 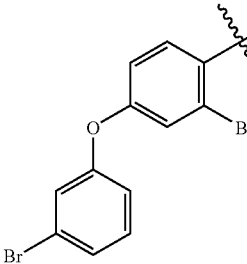 | 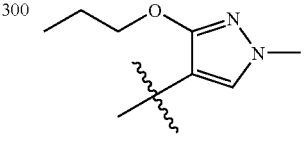 | 4.6 | B | |
| 300 | 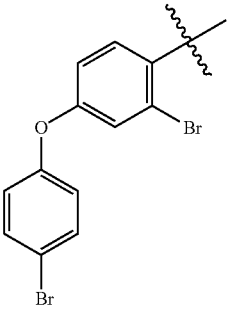 | 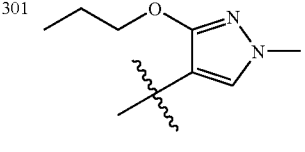 | 4.6 | B | |
| 301 | 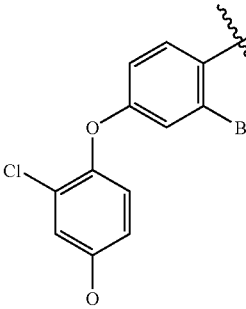 | | 4.9 | B | |

TABLE 1-continued

| N° | A | L | LogP | LogP method | M + 1 |
|----|---|---|------|-------------|-------|
| 302 | propoxy-pyrazole | 4-(4-hydroxy-3-trifluoromethylphenoxy)-2-bromophenyl | 4.9 | B | |
| 303 | propoxy-pyrazole | 4-(3,4-dichlorophenoxy)-2-bromophenyl | 4.9 | B | |
| 304 | propoxy-pyrazole | 4-(3-hydroxy-4-fluorophenoxy)-2-bromophenyl | 5.0 | B | |
| 305 | propoxy-pyrazole | 4-(3,5-dihydroxyphenoxy)-2-bromophenyl | 5.1 | B | |

TABLE 1-continued
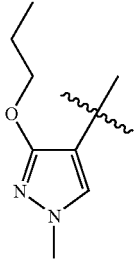
| N° | A | L | LogP | LogP method | M + 1 |
|---|---|---|---|---|---|
| 306 | 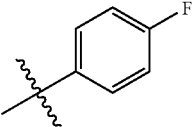 | 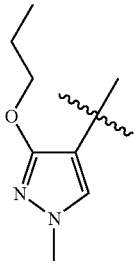 | | | 382 |
| 307 | 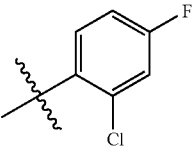 | 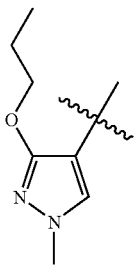 | | | 416 |
| 308 | 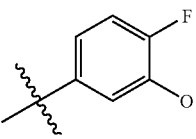 | 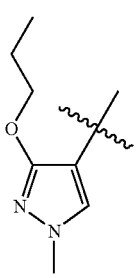 | | | 416 |
| 309 | 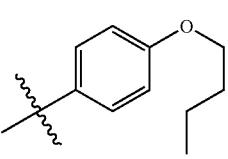 | 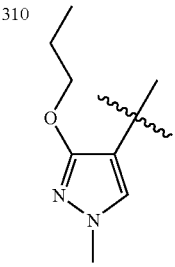 | | | 436 |
| 310 | 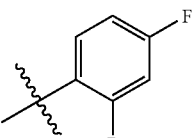 | | | | 460 |

TABLE 1-continued

| N° | A | L | LogP | LogP method | M + 1 |
|----|---|---|------|-------------|-------|
| 311 | (propoxy-pyrazole) | (phenoxy-phenol) | | | 490 |
| 312 | (propoxy-pyrazole) | (phenoxy-phenol) | | | 490 |
| 313 | (propoxy-pyrazole) | (tolyloxy-phenol) | | | 504 |
| 314 | (propoxy-pyrazole) | (methylpyridyloxy-bromophenyl) | | | 505 |

TABLE 1-continued
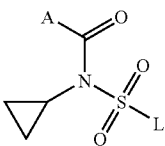
| N° | A | L | LogP | LogP method | M + 1 |
|----|---|---|------|-------------|-------|
| 315 | | | | | 505 |
| 316 | | | | | 520 |
| 317 | | | | | 520 |
| 318 | | | | | 524 |

TABLE 1-continued

| N° | A | L | LogP | LogP method | M + 1 |
|---|---|---|---|---|---|
| 319 | | | | | 524 |
| 320 | | | | | 524 |
| 321 | | | | | 524 |
| 322 | | | | | 524 |
| 323 | | | | | 524 |

TABLE 1-continued
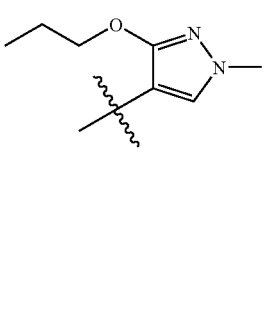
| N° | A | L | LogP | LogP method | M + 1 |
|---|---|---|---|---|---|
| 324 | 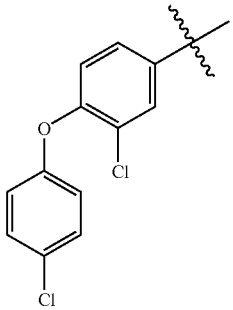 | 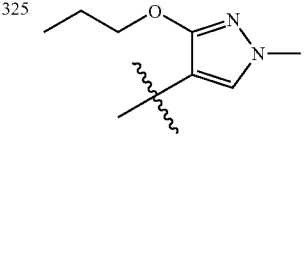 | | | 524 |
| 325 | 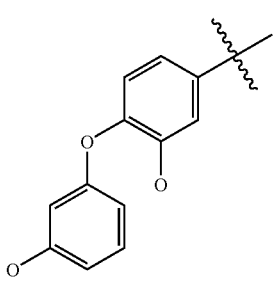 | 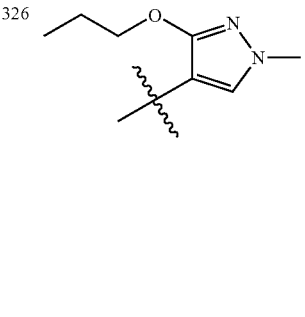 | | | 524 |
| 326 | 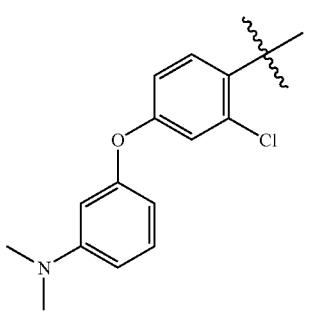 | 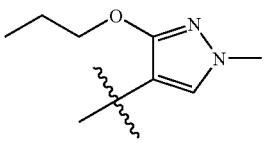 | | | 533 |
| 327 | 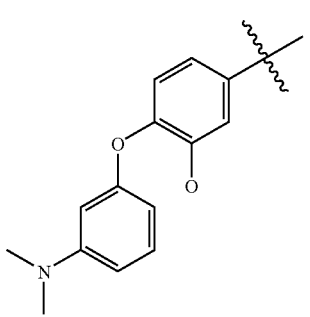 | | | | 533 |

TABLE 1-continued

| N° | A | L | LogP | LogP method | M + 1 |
|----|---|---|------|-------------|-------|
| 328 | (3-propoxy-1-methyl-1H-pyrazol-4-yl) | 4-(4-bromophenoxy)phenyl | | | 534 |
| 329 | (3-propoxy-1-methyl-1H-pyrazol-4-yl) | 4-(4-fluoro-3-hydroxyphenoxy)-3-hydroxyphenyl | | | 542 |
| 330 | (3-propoxy-1-methyl-1H-pyrazol-4-yl) | 4-(4-fluoro-3-hydroxyphenoxy)-2-hydroxyphenyl | | | 542 |
| 331 | (3-propoxy-1-methyl-1H-pyrazol-4-yl) | 4-(3,4-dimethoxyphenoxy)-3-hydroxyphenyl | | | 550 |

TABLE 1-continued

| N° | A | L | LogP | LogP method | M + 1 |
|---|---|---|---|---|---|
| 332 | propoxy-pyrazole | 2-chloro-4-(3,4-dimethoxyphenoxy)phenyl | | | 550 |
| 333 | propoxy-pyrazole | 2-chloro-4-(3-trifluoromethylphenoxy)phenyl | | | 558 |
| 334 | propoxy-pyrazole | 2-methoxy-4-(4-trifluoromethylphenoxy)phenyl | | | 558 |
| 335 | propoxy-pyrazole | 4-(2-chloro-4-methoxyphenoxy)-2-methoxyphenyl | | | 558 |

US 7,932,283 B2
TABLE 1-continued
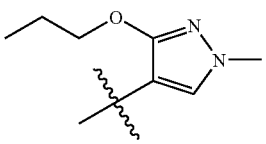
| N° | A | L | LogP | LogP method | M + 1 |
|----|---|---|------|-------------|-------|
| 336 | 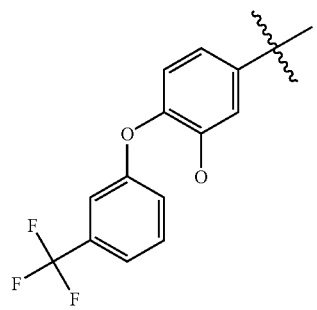 | 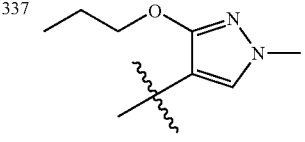 | | | 558 |
| 337 | 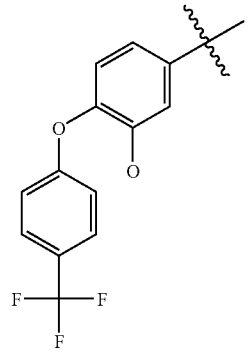 | 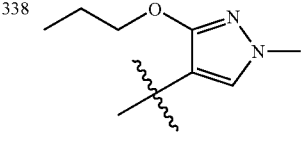 | | | 558 |
| 338 | 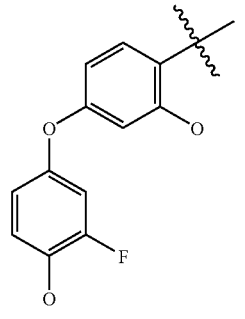 | 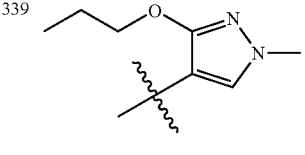 | | | 558 |
| 339 | 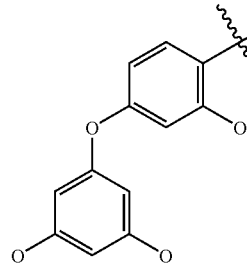 | | | | 558 |

TABLE 1-continued

| N° | A | L | LogP | LogP method | M + 1 |
|---|---|---|---|---|---|
| 340 | | | | | 558 |
| 341 | | | | | 558 |
| 342 | | | | | 558 |
| 343 | | | | | 560 |

TABLE 1-continued

| N° | A | L | LogP | LogP method | M + 1 |
|---|---|---|---|---|---|
| 344 | propoxy-pyrazole | phenoxy-phenyl with pentyl | | | 560 |
| 345 | propoxy-pyrazole | (3-bromophenoxy)phenyl | | | 568 |
| 346 | propoxy-pyrazole | (4-bromophenoxy)phenyl | | | 568 |
| 347 | propoxy-pyrazole | (3-bromophenoxy)phenyl | | | 568 |

TABLE 1-continued

| N° | A | L | LogP | LogP method | M + 1 |
|---|---|---|---|---|---|
| 348 | propoxy-pyrazole | 2-chloro-4-...phenol with Br substituent | | | 568 |
| 349 | propoxy-pyrazole | 3-(trifluoromethoxy)phenoxy-phenol | | | 574 |
| 350 | propoxy-pyrazole | 3-(trifluoromethoxy)phenoxy-phenol | | | 574 |
| 351 | propoxy-pyrazole | 2-fluoro-3-(trifluoromethyl)phenoxy-chlorophenyl | | | 576 |

TABLE 1-continued

| N° | A | L | LogP | LogP method | M + 1 |
|---|---|---|---|---|---|
| 352 | | | | | 592 |
| 353 | | | | | 592 |
| 354 | | | | | 592 |
| 355 | | | | | 602 |

TABLE 1-continued

| N° | A | L | LogP | LogP method | M + 1 |
|---|---|---|---|---|---|
| 356 | (propoxy-pyrazolyl group) | (bromo-dihydroxy-diphenyl ether group) | | | 602 |
| 357 | (1-methyl-5-fluoro-3-trifluoromethyl-pyrazol-4-yl) | (2,3-dihydroxyphenyl) | 3.3 | B | |
| 358 | (1-methyl-5-fluoro-3-trifluoromethyl-pyrazol-4-yl) | (3-chloro-2-fluorophenyl) | 3.2 | B | |
| 359 | (1-methyl-5-fluoro-3-trifluoromethyl-pyrazol-4-yl) | (4-butylphenyl) | 4.3 | B | |
| 360 | (1-methyl-5-fluoro-3-trifluoromethyl-pyrazol-4-yl) | (2,6-dihydroxyphenyl) | 3.1 | B | |

TABLE 1-continued

| N° | A | L | LogP | LogP method | M + 1 |
|---|---|---|---|---|---|
| 361 | 1-methyl-5-fluoro-3-(trifluoromethyl)pyrazol-4-yl | 2,5-dihydroxyphenyl | 4.0 | B | |
| 362 | 1-methyl-5-fluoro-3-(trifluoromethyl)pyrazol-4-yl | 4-fluoro-2-hydroxyphenyl | 3.1 | B | |
| 363 | 1-methyl-5-fluoro-3-(trifluoromethyl)pyrazol-4-yl | 2,6-dihydroxy-4-hydroxyphenyl | 3.7 | B | |
| 364 | 1-methyl-5-fluoro-3-(trifluoromethyl)pyrazol-4-yl | 2-(trifluoromethyl)phenyl | 3.1 | B | |
| 365 | 1-methyl-5-fluoro-3-(trifluoromethyl)pyrazol-4-yl | 2-(trifluoromethoxy)phenyl | 3.2 | B | |
| 366 | 1-methyl-5-fluoro-3-(trifluoromethyl)pyrazol-4-yl | 2,3,4-trifluorophenyl | | | 446 |

TABLE 1-continued
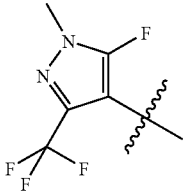
| N° | A | L | LogP | LogP method | M + 1 |
|---|---|---|---|---|---|
| 367 | 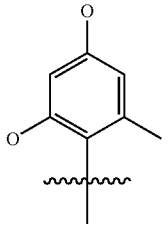 | 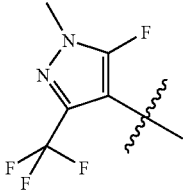 | 2.6 | B | |
| 368 | 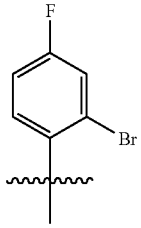 | 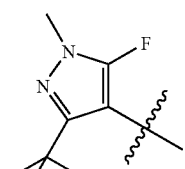 | 3.2 | B | |
| 369 | 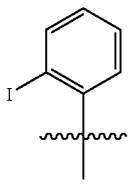 | 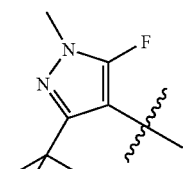 | 3.0 | B | |
| 370 | 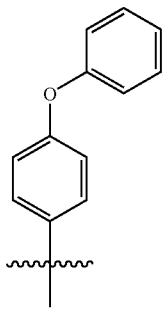 | 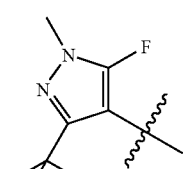 | 3.9 | B | |
| 371 | 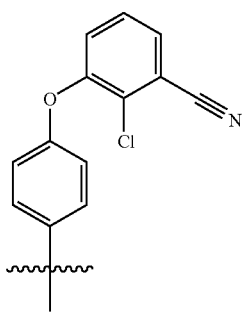 | | 3.7 | B | |

TABLE 1-continued

| N° | A | L | LogP | LogP method | M + 1 |
|---|---|---|---|---|---|
| 372 | | | 4.2 | B | |
| 373 | | | 3.9 | B | |
| 374 | | | 2.7 | B | |
| 375 | | | 3.6 | B | |
| 376 | | | 3.9 | B | |

TABLE 1-continued
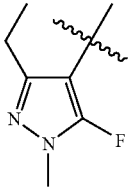
| N° | A | L | LogP | LogP method | M + 1 |
|---|---|---|---|---|---|
| 377 | 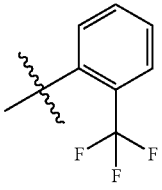 | 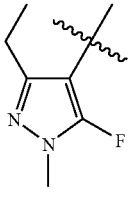 | 2.9 | B | |
| 378 | 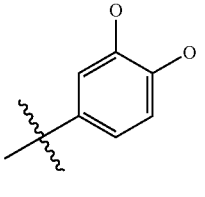 | 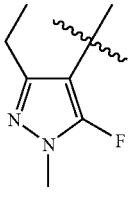 | 3.8 | B | |
| 379 | 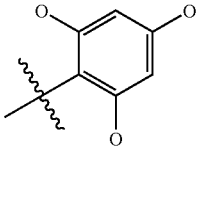 | 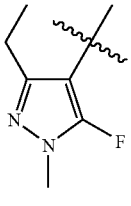 | 3.6 | B | |
| 380 | 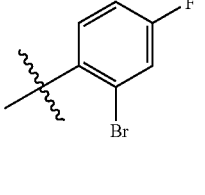 | 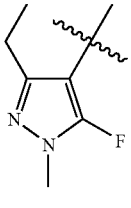 | 2.9 | B | |
| 381 | 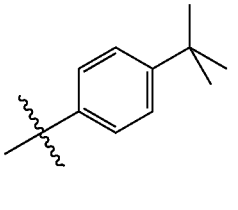 | 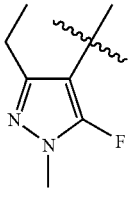 | | | 408 |
| 382 | 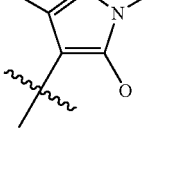 | 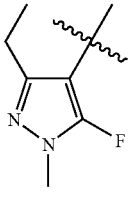 | 2.3 | B | |
| 383 | 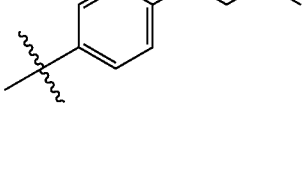 | | 4.2 | B | |

TABLE 1-continued
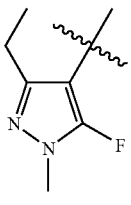
| N° | A | L | LogP | LogP method | M + 1 |
|---|---|---|---|---|---|
| 384 | 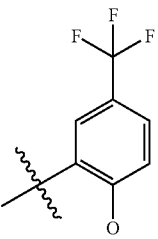 | 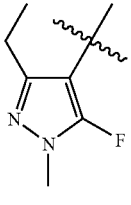 | 3.5 | B | |
| 385 | 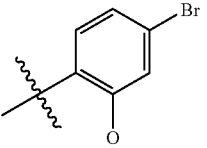 | 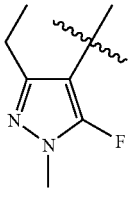 | 3.4 | B | |
| 386 | 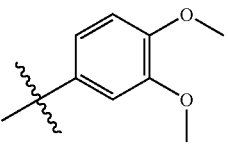 | 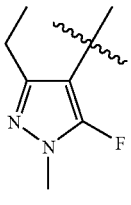 | 2.5 | B | |
| 387 | 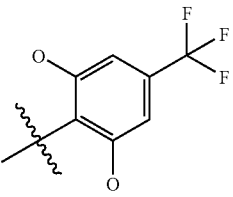 | 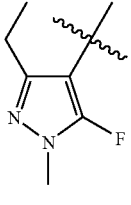 | 3.8 | B | |
| 388 | 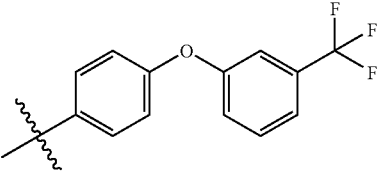 | 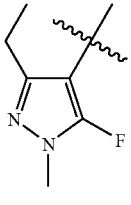 | 4.2 | B | |
| 389 | | 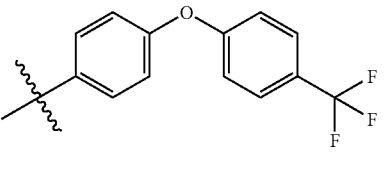 | 4.3 | B | |

TABLE 1-continued
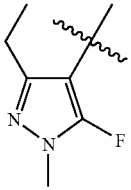
| N° | A | L | LogP | LogP method | M + 1 |
|---|---|---|---|---|---|
| 390 | 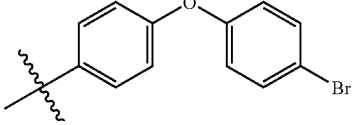 | 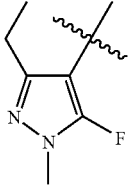 | 4.4 | B | |
| 391 | 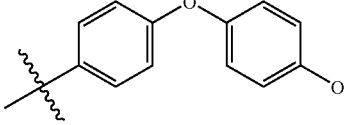 | 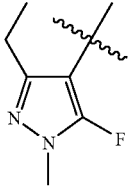 | 4.2 | B | |
| 392 | 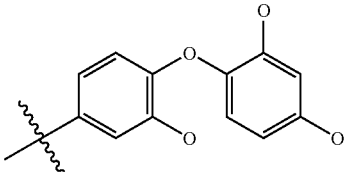 | 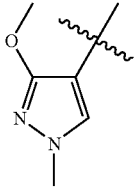 | | | 546 |
| 393 | 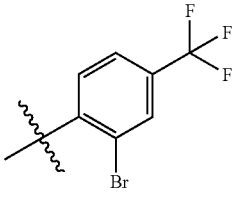 | 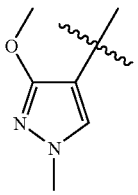 | | | 481 |
| 394 | 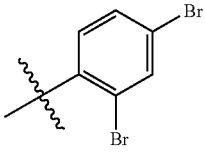 | 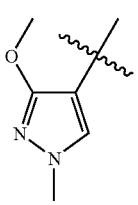 | | | 491 |
| 395 | 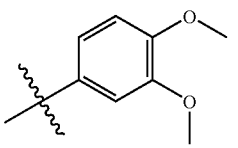 | 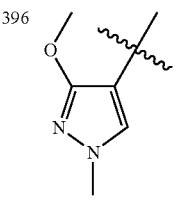 | 1.9 | B | |
| 396 | 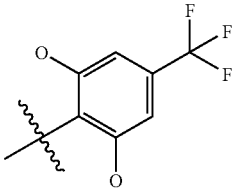 |  | 3.0 | B | |

TABLE 1-continued

| N° | A | L | LogP | LogP method | M + 1 |
|---|---|---|---|---|---|
| 397 | 3-ethoxy-1-methyl-1H-pyrazol-4-yl | 4-butoxyphenyl | | | 422 |
| 398 | 3-ethoxy-1-methyl-1H-pyrazol-4-yl | 4-(3,5-dioxophenoxy)phenyl | | | 510 |
| 399 | 1,3-dimethyl-5-(3-oxophenoxy)-1H-pyrazol-4-yl | 3-oxophenyl | 3.94 | A | |
| 400 | 5-(3-chlorophenoxy)-1,3-dimethyl-1H-pyrazol-4-yl | 4-(trifluoromethyl)phenyl | 4.13 | A | |
| 401 | 3,5-dimethyl-1H-pyrazol-4-yl | 3-chlorophenyl | 2.45 | A | |

TABLE 1-continued

| N° | A | L | LogP | LogP method | M + 1 |
|---|---|---|---|---|---|
| 402 | 3,5-dimethyl-1H-pyrazol-4-yl | 4-(trifluoromethyl)phenyl | 2.50 | A | |
| 403 | 1,3-dimethyl-1H-pyrazol-4-yl (or 1,5-dimethyl) | 4-(trifluoromethyl)phenyl | 3 | A | |
| 404 | 5-(3-chlorophenoxy)-1,3-dimethyl-1H-pyrazol-4-yl | 4-(trifluoromethoxy)-3-(trifluoromethyl)phenyl | 4.56 | A | |
| 405 | 5-(3-hydroxyphenoxy)-1,3-dimethyl-1H-pyrazol-4-yl | 3,4-methylenedioxyphenyl | 4.46 | A | |
| 406 | 5-hydroxy-1,3-dimethyl-1H-pyrazol-4-yl | 4-(trifluoromethoxy)-3-(trifluoromethyl)phenyl | 3.76 | A | |

TABLE 1-continued

| N° | A | L | LogP | LogP method | M + 1 |
|---|---|---|---|---|---|
| 407 | 1,3-dimethyl-5-oxo-pyrazol-4-yl | 3,4-dimethoxyphenyl | 3.63 | A | |
| 408 | 3,5-dimethyl-1H-pyrazol-4-yl | 4-methoxy-3-(trifluoromethyl)phenyl | 3 | A | |
| 409 | 3,5-dimethyl-1H-pyrazol-4-yl | 3,4-dimethoxyphenyl | 2.74 | A | |
| 410 | 3,5-dimethyl-1H-pyrazol-4-yl | 4-tert-butylphenyl | 3.04 | A | |
| 411 | 1,3,5-trimethyl-pyrazol-4-yl | 4-methoxy-3-(trifluoromethyl)phenyl | 3.37 | A | |
| 412 | 1,3,5-trimethyl-pyrazol-4-yl | 3,4-dimethoxyphenyl | 3.21 | A | |

TABLE 1-continued

| N° | A | L | LogP | LogP method | M + 1 |
|---|---|---|---|---|---|
| 413 | 1,3,5-trimethylpyrazol-4-yl | 2,4-dihydroxyphenyl | 2.8 | A | |
| 414 | 1,3,5-trimethylpyrazol-4-yl | 4-tert-butylphenyl | 3.41 | A | |
| 415 | 3-ethyl-5-fluoro-1-methylpyrazol-4-yl | 2,3,4-trifluorophenyl | | | 406 |
| 416 | 3-ethyl-5-fluoro-1-methylpyrazol-4-yl | 4-phenoxyphenyl | | | 444 |
| 417 | 3-ethyl-5-fluoro-1-methylpyrazol-4-yl | 4-fluoro-2-hydroxyphenyl | | | 404 |
| 418 | 3-ethyl-5-fluoro-1-methylpyrazol-4-yl | 2,4,5-trichlorophenyl | | | 453 |

TABLE 1-continued
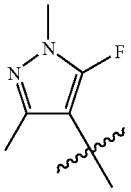
| N° | A | L | LogP | LogP method | M + 1 |
|---|---|---|---|---|---|
| 419 | 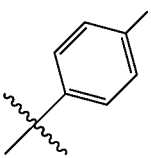 | 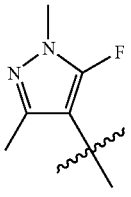 | | | 416 |
| 420 | 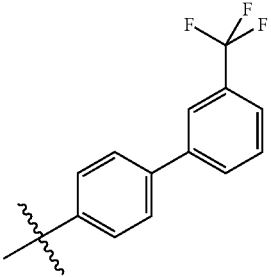 | 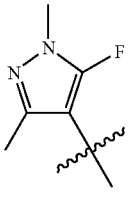 | | | 482 |
| 421 | 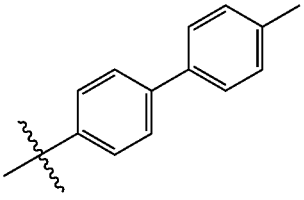 | 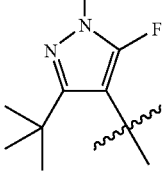 | | | 428 |
| 422 | 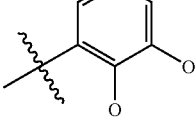 | 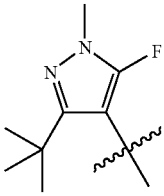 | | | 448 |
| 423 | 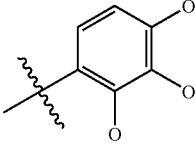 | 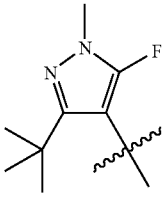 | | | 482 |
| 424 | 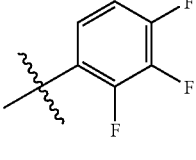 | | | | 434 |

TABLE 1-continued

| N° | A | L | LogP | LogP method | M + 1 |
|---|---|---|---|---|---|
| 425 | | | | | 432 |
| 426 | | | | | 472 |
| 427 | | | | | 482 |
| 428 | | | | | 414 |
| 429 | | | | | 434 |
| 430 | | | | | 468 |

TABLE 1-continued
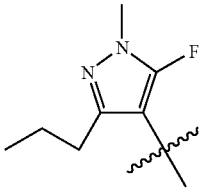
| N° | A | L | LogP | LogP method | M + 1 |
|---|---|---|---|---|---|
| 431 | 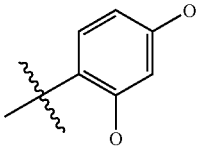 | 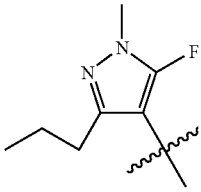 | | | 434 |
| 432 | 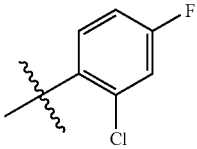 | 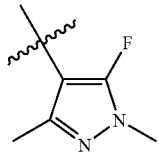 | | | 418 |
| 433 | 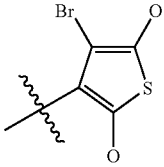 | 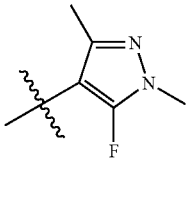 | | | 489 |
| 434 | 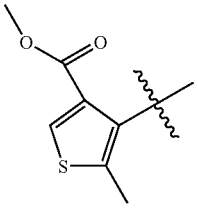 | 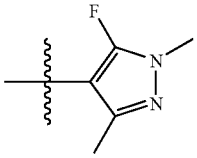 | 2.24 | A | |
| 435 | 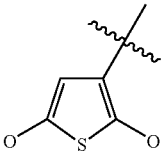 | 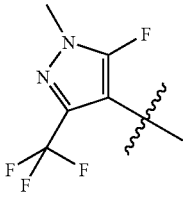 | 3.16 | A | |
| 436 | 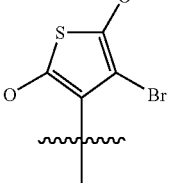 | 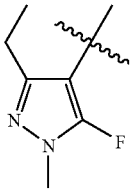 | 3.9 | B | |
| 437 | 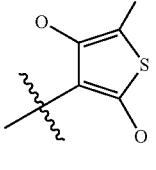 |  | 3.85 | B | |

TABLE 1-continued

| N° | A | L | LogP | LogP method | M + 1 |
|---|---|---|---|---|---|
| 438 | | | 4.0 | B | |
| 439 | | | | | 487 |
| 440 | | | 3.1 | B | |
| 441 | | | | | 393 |
| 442 | | | | | 390 |
| 443 | | | 2.6 | B | |
| 444 | | | 1.7 | B | |

TABLE 1-continued

| N° | A | L | LogP | LogP method | M + 1 |
|---|---|---|---|---|---|
| 445 | | | | | 441 |
| 446 | | | 1.96 | A | |
| 447 | | | 3.08 | A | |
| 448 | | | 3.5 | B | |
| 449 | | | 2.0 | B | |
| 450 | | | | | 464 |
| 451 | | | | | 394 |

TABLE 1-continued

| N° | A | L | LogP | LogP method | M + 1 |
|----|---|---|------|-------------|-------|
| 452 | | | | | 450 |
| 453 | | | | | 478 |
| 454 | | | | | 448 |
| 455 | | | | | 380 |
| 456 | | | | | 422 |
| 457 | | | | | 420 |

TABLE 1-continued

| N° | A | L | LogP | LogP method | M + 1 |
|---|---|---|---|---|---|
| 458 | | | 2.0 | B | |
| 459 | | | 2.2 | B | |
| 460 | | | 2.3 | B | |
| 461 | | | 2.7 | B | |
| 462 | | | 2.9 | B | |

TABLE 1-continued

| N° | A | L | LogP | LogP method | M + 1 |
|----|---|---|------|-------------|-------|
| 463 | 3-methoxy-1-methyl-1H-pyrazol-4-yl | 2-bromo-4-(4-methoxyphenoxy)phenyl | 3.3 | B | |
| 464 | 3-methoxy-1-methyl-1H-pyrazol-4-yl | 2-bromo-4-phenoxyphenyl | 3.3 | B | |
| 465 | 3-methoxy-1-methyl-1H-pyrazol-4-yl | 2-bromo-4-(2-hydroxyphenoxy)phenyl | 3.5 | B | |
| 466 | 3-methoxy-1-methyl-1H-pyrazol-4-yl | 2-bromo-4-(3-(dimethylamino)phenoxy)phenyl | 3.5 | B | |

TABLE 1-continued

| N° | A | L | LogP | LogP method | M + 1 |
|----|---|---|------|-------------|-------|
| 467 | methoxy-methylpyrazole | 3-bromo-4-(4-methylphenoxy)phenyl | 3.7 | B | |
| 468 | methoxy-methylpyrazole | 3-bromo-4-(3-hydroxyphenoxy)phenyl | 3.7 | B | |
| 469 | methoxy-methylpyrazole | 3-bromo-4-(4-chlorophenoxy)phenyl | 3.8 | B | |
| 470 | methoxy-methylpyrazole | 3-bromo-4-(3-hydroxy-4-methylphenoxy)phenyl | 3.8 | B | |

TABLE 1-continued
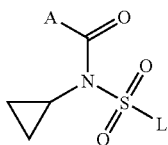
| N° | A | L | LogP | LogP method | M + 1 |
|---|---|---|---|---|---|
| 471 | | | 3.8 | B | |
| 472 | | | 3.8 | B | |
| 473 | | | 3.8 | B | |
| 474 | | | 3.9 | B | |

TABLE 1-continued
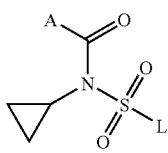
| N° | A | L | LogP | LogP method | M + 1 |
|---|---|---|---|---|---|
| 475 | | | 3.9 | B | |
| 476 | | | 4.0 | B | |
| 477 | | | 4.1 | B | |
| 478 | | | 4.2 | B | |

TABLE 1-continued

| N° | A | L | LogP | LogP method | M + 1 |
|---|---|---|---|---|---|
| 479 | methoxy-methylpyrazole | 4-(4-chloro-3-(trifluoromethyl)phenoxy)-2-bromophenyl | 4.2 | B | |
| 480 | methoxy-methylpyrazole | 4-(4-bromo-3-hydroxyphenoxy)-2-bromophenyl | 4.2 | B | |
| 481 | methoxy-methylpyrazole | 4-(3,5-dihydroxyphenoxy)-2-bromophenyl | 4.3 | B | |
| 482 | methoxy-methylpyrazole | 4-(4-pentylphenoxy)-2-bromophenyl | 5.4 | B | |

TABLE 1-continued

| N° | A | L | LogP | LogP method | M + 1 |
|---|---|---|---|---|---|
| 483 | | | | | 354 |
| 484 | | | | | 388 |
| 485 | | | | | 388 |
| 486 | | | | | 426 |
| 487 | | | | | 442 |
| 488 | | | | | 446 |
| 489 | | | | | 448 |

TABLE 1-continued

| N° | A | L | LogP | LogP method | M + 1 |
|---|---|---|---|---|---|
| 490 | | | | | 458 |
| 491 | | | | | 460 |
| 492 | | | | | 462 |
| 493 | | | | | 462 |
| 494 | | | | | 476 |

TABLE 1-continued

| N° | A | L | LogP | LogP method | M + 1 |
|---|---|---|---|---|---|
| 495 | methoxy-methyl-pyrazole | phenoxyphenyl with OMe | | | 476 |
| 496 | methoxy-methyl-pyrazole | phenoxyphenyl with Cl | | | 477 |
| 497 | methoxy-methyl-pyrazole | (4-methoxyphenoxy)phenyl with O | | | 492 |
| 498 | methoxy-methyl-pyrazole | (4-methoxyphenoxy)methylphenyl | | | 492 |

TABLE 1-continued

| N° | A | L | LogP | LogP method | M + 1 |
|---|---|---|---|---|---|
| 499 | | | | | 496 |
| 500 | | | | | 496 |
| 501 | | | | | 496 |
| 502 | | | | | 505 |
| 503 | | | | | 512 |

TABLE 1-continued

| N° | A | L | LogP | LogP method | M + 1 |
|---|---|---|---|---|---|
| 504 | | | | | 514 |
| 505 | | | | | 514 |
| 506 | | | | | 522 |
| 507 | | | | | 522 |

TABLE 1-continued

| N° | A | L | LogP | LogP method | M + 1 |
|---|---|---|---|---|---|
| 508 | methoxy-methylpyrazole | 4-(3-trifluoromethylphenoxy)-3-chlorophenyl | | | 530 |
| 509 | methoxy-methylpyrazole | 4-(4-trifluoromethylphenoxy)-3-hydroxyphenyl | | | 530 |
| 510 | methoxy-methylpyrazole | 4-(2-bromo-4-chlorophenoxy)-3-hydroxyphenyl | | | 530 |
| 511 | methoxy-methylpyrazole | 4-(3,4-dihydroxyphenoxy)-3-hydroxyphenyl | | | 530 |

TABLE 1-continued
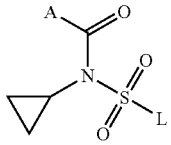
| N° | A | L | LogP | LogP method | M + 1 |
|---|---|---|---|---|---|
| 512 | 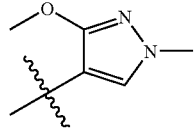 | 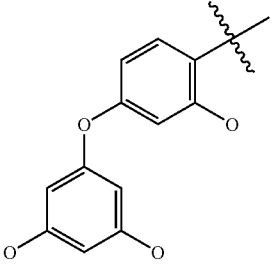 | | | 530 |
| 513 | 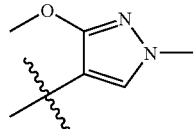 | 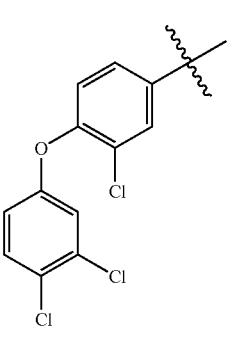 | | | 530 |
| 514 | 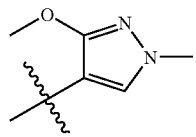 | 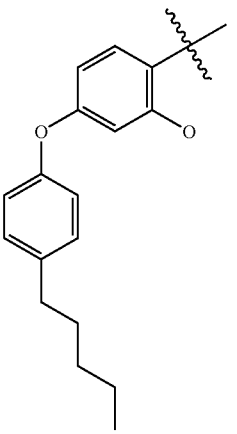 | | | 532 |

TABLE 1-continued
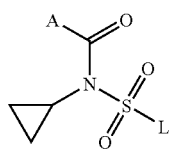
| N° | A | L | LogP | LogP method | M + 1 |
|----|---|---|------|-------------|-------|
| 515 | | | | | 532 |
| 516 | | | | | 541 |
| 517 | | | | | 541 |
| 518 | | | | | 546 |

TABLE 1-continued
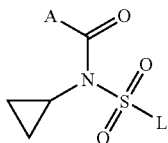
| N° | A | L | LogP | LogP method | M + 1 |
|---|---|---|---|---|---|
| 519 | | | | | 548 |
| 520 | | | | | 548 |
| 521 | | | | | 554 |
| 522 | | | | | 564 |

TABLE 1-continued
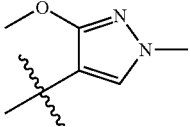
| N° | A | L | LogP | LogP method | M + 1 |
|----|---|---|------|-------------|-------|
| 523 | 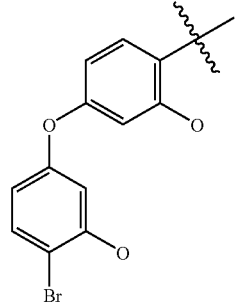 | 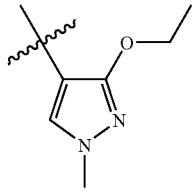 | | | 575 |
| 524 | 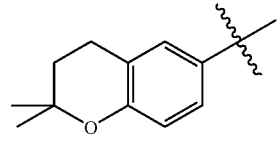 | 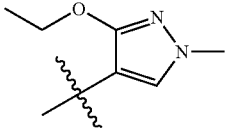 | | | 434 |
| 525 | 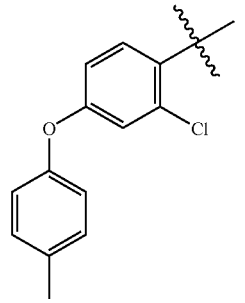 | 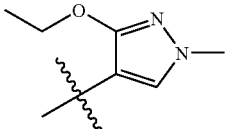 | 2.2 | B | |
| 526 | 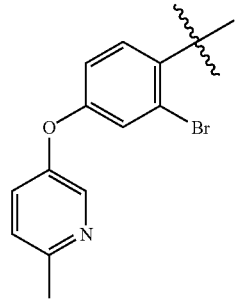 | | 2.3 | B | |

TABLE 1-continued

| N° | A | L | LogP | LogP method | M + 1 |
|---|---|---|---|---|---|
| 527 | ethoxy-methylpyrazole | 4-(3-hydroxy-3,4-dimethoxyphenoxy)phenyl | 3.2 | B | |
| 528 | ethoxy-methylpyrazole | 4-(3,4-dimethoxyphenoxy)-3-hydroxyphenyl | 3.5 | B | |
| 529 | ethoxy-methylpyrazole | 3-hydroxy-4-(4-methoxyphenoxy)phenyl | 3.5 | B | |
| 530 | ethoxy-methylpyrazole | 3-hydroxy-4-phenoxyphenyl | 3.6 | B | |

TABLE 1-continued

| N° | A | L | LogP | LogP method | M + 1 |
|---|---|---|---|---|---|
| 531 | 3-ethoxy-1-methylpyrazol-4-yl | 4-(4-methoxyphenoxy)-3-hydroxyphenyl | 3.8 | B | |
| 532 | 3-ethoxy-1-methylpyrazol-4-yl | 4-(3-dimethylamino-phenoxy)-... (hydroxy-substituted phenyl) | 3.8 | B | |
| 533 | 3-ethoxy-1-methylpyrazol-4-yl | 4-phenoxy-3-hydroxyphenyl | 3.9 | B | |
| 534 | 3-ethoxy-1-methylpyrazol-4-yl | 4-(3-hydroxyphenoxy)-3-hydroxyphenyl | 3.9 | B | |

TABLE 1-continued

| N° | A | L | LogP | LogP method | M + 1 |
|---|---|---|---|---|---|
| 535 | | | 4.0 | B | |
| 536 | | | 4.0 | B | |
| 537 | | | 4.1 | B | |
| 538 | | | 4.1 | B | |

TABLE 1-continued

| N° | A | L | LogP | LogP method | M + 1 |
|---|---|---|---|---|---|
| 539 | ethoxy-pyrazole | 3-(dimethylamino)phenoxy-phenyl | 4.1 | B | |
| 540 | ethoxy-pyrazole | 3-bromophenoxy-bromophenyl | 4.2 | B | |
| 541 | ethoxy-pyrazole | 4-bromophenoxy-bromophenyl | 4.2 | B | |
| 542 | ethoxy-pyrazole | 4-methylphenoxy-phenyl | 4.3 | B | |

TABLE 1-continued

| N° | A | L | LogP | LogP method | M + 1 |
|---|---|---|---|---|---|
| 543 | 3-ethoxy-1-methyl-1H-pyrazol-4-yl | 4-(2-chloro-4-hydroxyphenoxy)-2-hydroxyphenyl | 4.3 | B | |
| 544 | 3-ethoxy-1-methyl-1H-pyrazol-4-yl | 4-(4-bromo-3-hydroxyphenoxy)-3-hydroxyphenyl | 4.3 | B | |
| 545 | 3-ethoxy-1-methyl-1H-pyrazol-4-yl | 3-hydroxy-4-(4-hydroxyphenoxy)phenyl | 4.3 | B | |
| 546 | 3-ethoxy-1-methyl-1H-pyrazol-4-yl | 3-hydroxy-4-(3-hydroxyphenoxy)phenyl | 4.3 | B | |

TABLE 1-continued

| N° | A | L | LogP | LogP method | M + 1 |
|---|---|---|---|---|---|
| 547 | 3-ethoxy-1-methyl-1H-pyrazol-4-yl | 4-(2-fluoro-3-(trifluoromethyl)phenoxy)-3-hydroxyphenyl | 4.3 | B | |
| 548 | 3-ethoxy-1-methyl-1H-pyrazol-4-yl | 4-(4-fluoro-3-hydroxyphenoxy)-3-hydroxyphenyl | 4.4 | B | |
| 549 | 3-ethoxy-1-methyl-1H-pyrazol-4-yl | 3-hydroxy-4-(3-(trifluoromethyl)phenoxy)phenyl | 4.4 | B | |
| 550 | 3-ethoxy-1-methyl-1H-pyrazol-4-yl | 3-bromo-4-(4-(trifluoromethyl)phenoxy)phenyl | 4.4 | B | |

TABLE 1-continued

| N° | A | L | LogP | LogP method | M + 1 |
|----|---|---|------|-------------|-------|
| 551 | ethoxy-methylpyrazole | 4-(3-bromophenoxy)phenyl | 4.5 | B | |
| 552 | ethoxy-methylpyrazole | 4-(4-bromophenoxy)phenyl | 4.5 | B | |
| 553 | ethoxy-methylpyrazole | 2-bromo-4-(4-chloro-3-trifluoromethylphenoxy)phenyl | 4.5 | B | |
| 554 | ethoxy-methylpyrazole | 4-(3-trifluoromethoxyphenoxy)phenyl | 4.5 | B | |

TABLE 1-continued

| N° | A | L | LogP | LogP method | M + 1 |
|---|---|---|---|---|---|
| 555 | | | 4.7 | B | |
| 556 | | | 4.8 | B | |
| 557 | | | 4.8 | B | |
| 558 | | | 4.9 | B | |

US 7,932,283 B2
TABLE 1-continued
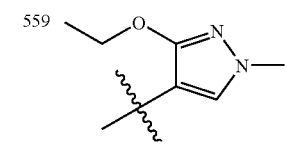
| N° | A | L | LogP | LogP method | M + 1 |
|---|---|---|---|---|---|
| 559 | 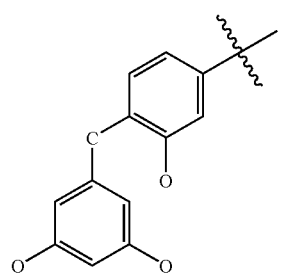 | 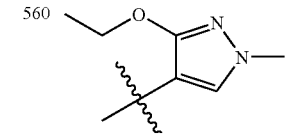 | 5.0 | B | |
| 560 | 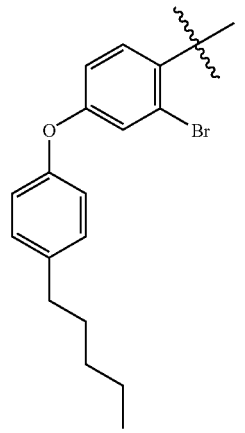 | 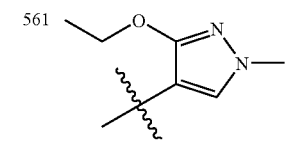 | 5.6 | B | |
| 561 | 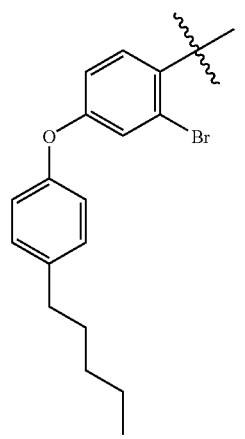 | 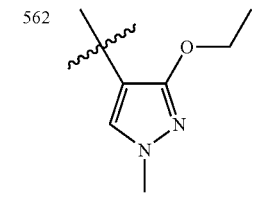 | 5.8 | B | |
| 562 | 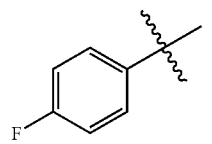 | | | | 368 |

TABLE 1-continued

| N° | A | L | LogP | LogP method | M + 1 |
|---|---|---|---|---|---|
| 563 | 3-ethoxy-1-methylpyrazol-4-yl | 2-chloro-4-fluorophenyl | | | 402 |
| 564 | 3-ethoxy-1-methylpyrazol-4-yl | 4-fluoro-3-hydroxyphenyl | | | 402 |
| 565 | 3-ethoxy-1-methylpyrazol-4-yl | 4-phenoxyphenyl | | | 443 |
| 566 | 3-ethoxy-1-methylpyrazol-4-yl | 2-bromo-4-fluorophenyl | | | 446 |
| 567 | 3-ethoxy-1-methylpyrazol-4-yl | 2-hydroxy-4-(4-methylphenoxy)phenyl | | | 490 |

TABLE 1-continued

| N° | A | L | LogP | LogP method | M + 1 |
|---|---|---|---|---|---|
| 568 | 3-ethoxy-1-methyl-pyrazol-4-yl | 4-(3-hydroxyphenoxy)-2-hydroxyphenyl | | | 510 |
| 569 | 3-ethoxy-1-methyl-pyrazol-4-yl | 2-chloro-4-(3-trifluoromethylphenoxy)phenyl | | | 544 |
| 570 | 3-ethoxy-1-methyl-pyrazol-4-yl | 4-(4-chloro-3-hydroxyphenoxy)-2-hydroxyphenyl | | | 544 |
| 571 | 3-ethoxy-1-methyl-pyrazol-4-yl | 4-(3,5-dihydroxyphenoxy)-2-hydroxyphenyl | | | 544 |

TABLE 1-continued

| N° | A | L | LogP | LogP method | M + 1 |
|---|---|---|---|---|---|
| 572 | | | | | 560 |
| 573 | | | | | 562 |
| 574 | | | | | 578 |
| 575 | | | | | 432 |
| 576 | | | | | 342 |

US 7,932,283 B2
TABLE 1-continued
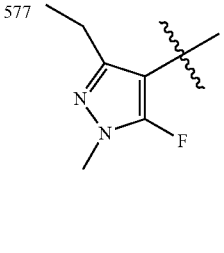
| N° | A | L | LogP | LogP method | M + 1 |
|---|---|---|---|---|---|
| 577 | 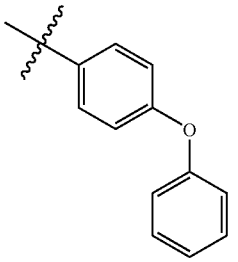 | 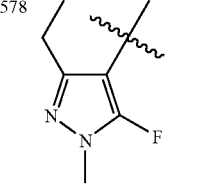 | | | 445 |
| 578 | 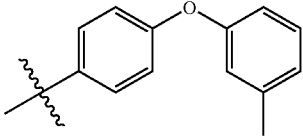 | 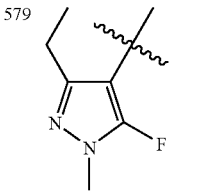 | | | 458 |
| 579 | 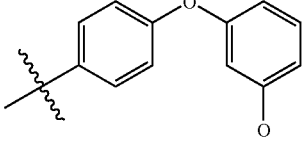 | 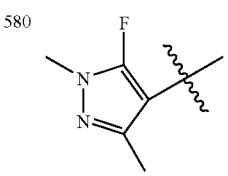 | | | 478 |
| 580 | 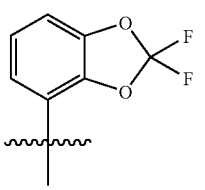 | 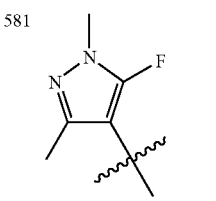 | | | 418 |
| 581 | 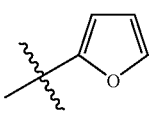 | 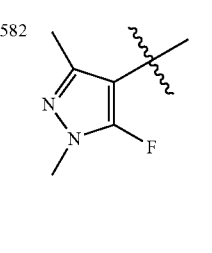 | | | 328 |
| 582 | 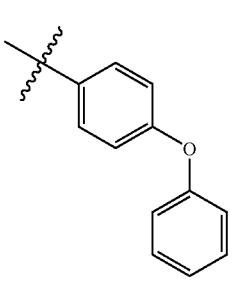 | | | | 431 |

TABLE 1-continued

| N° | A | L | LogP | LogP method | M + 1 |
|---|---|---|---|---|---|
| 583 | | | | | 444 |
| 584 | | | | | 482 |
| 585 | | | | | 464 |
| 586 | | | 3.7 | B | |
| 587 | | | | | 354 |
| 588 | | | 3.46 | A | |
| 589 | | | 4.18 | A | |

TABLE 1-continued

| N° | A | L | LogP | LogP method | M + 1 |
|---|---|---|---|---|---|
| 590 | 5-ethyl-3-isopropylisoxazol-4-yl | 4-(trifluoromethyl)phenyl | 4.37 | A | |
| 591 | 3,5-dimethylisoxazol-4-yl | 3,4-dimethoxyphenyl | 3.72 | A | |
| 592 | 3,5-dimethylisoxazol-4-yl | 2,4-dimethoxyphenyl | 3.41 | A | |
| 593 | 3,5-dimethylisoxazol-4-yl | 4-tert-butylphenyl | 4.03 | A | |
| 594 | 5-ethyl-3-isopropylisoxazol-4-yl | 4-methoxy-3-(trifluoromethyl)phenyl | 4.82 | A | |

TABLE 1-continued

| N° | A | L | LogP | LogP method | M + 1 |
|---|---|---|---|---|---|
| 595 | | | 4.77 | A | |
| 596 | | | 4.41 | A | |
| 597 | | | 4.98 | A | |
| 598 | | | | | 341 |
| 599 | | | 3.0 | B | |
| 600 | | | 3.6 | B | |

TABLE 1-continued

| N° | A | L | LogP | LogP method | M + 1 |
|---|---|---|---|---|---|
| 601 | 3-methylisoxazol-4-yl | 4-phenoxyphenyl | 3.7 | B | |
| 602 | 3-methylisoxazol-4-yl | 4-(4-bromophenoxy)phenyl | 4.2 | B | |
| 603 | 5-methylisoxazol-4-yl | 2,3-methylenedioxyphenyl | 2.2 | B | |
| 604 | 5-methylisoxazol-4-yl | 2,3,4-trioxyphenyl | 2.6 | B | |
| 605 | 5-methylisoxazol-4-yl | 4-(4-bromophenoxy)phenyl | 3.4 | B | |

TABLE 1-continued
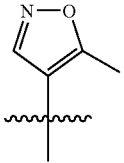
| N° | A | L | LogP | LogP method | M + 1 |
|---|---|---|---|---|---|
| 606 | 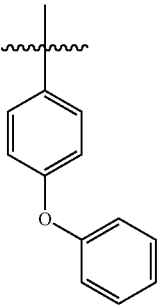 | 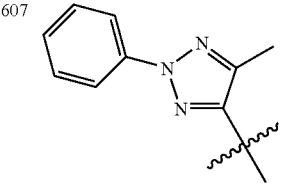 | 3.7 | B | |
| 607 | 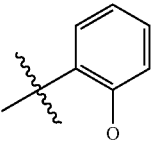 | 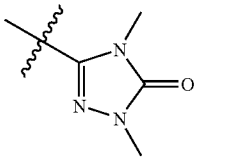 | | | 417 |
| 608 | 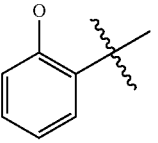 | 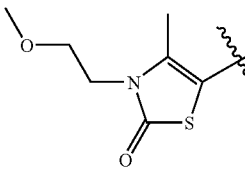 | 1.97 | A | |
| 609 | 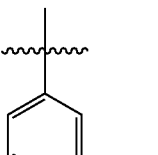 | 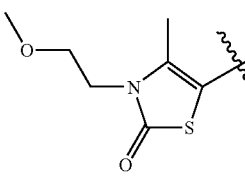 | 2.01 | A | |
| 610 | 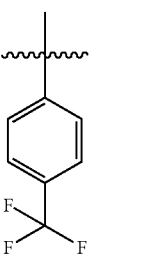 | 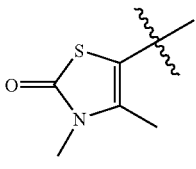 | 2.01 | A | |
| 611 | 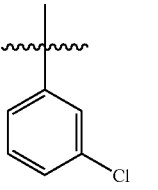 | | 1.01 | A | |

TABLE 1-continued

| N° | A | L | LogP | LogP method | M + 1 |
|---|---|---|---|---|---|
| 612 | | | 2.01 | A | |
| 613 | | | 2.01 | A | |
| 614 | | | 4.08 | A | |
| 615 | | | 2.01 | A | |
| 616 | | | 2.01 | A | |
| 617 | | | 2.01 | A | |

TABLE 1-continued
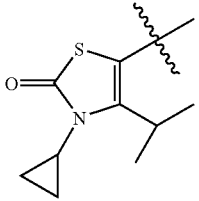
| N° | A | L | LogP | LogP method | M + 1 |
|---|---|---|---|---|---|
| 618 | 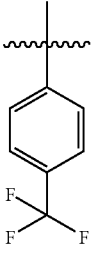 | 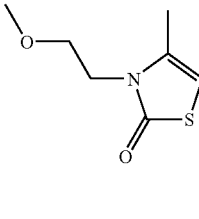 | 4.03 | A | |
| 619 | 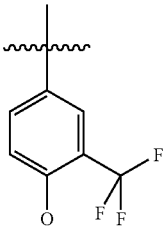 | 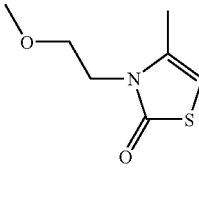 | 2.01 | A | |
| 620 | 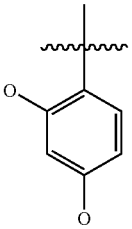 | 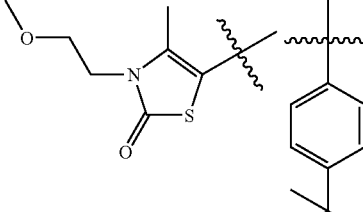 | 2.01 | A | |
| 621 | 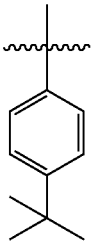 | 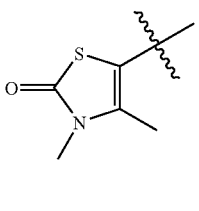 | 2.01 | A | |
| 622 | 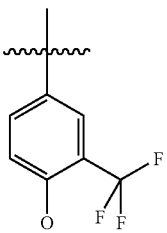 | | 2.01 | A | |

TABLE 1-continued
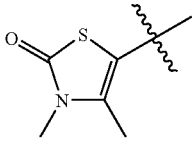
| N° | A | L | LogP | LogP method | M + 1 |
|----|---|---|------|-------------|-------|
| 623 | 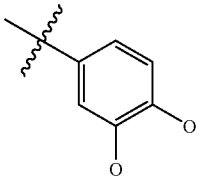 | 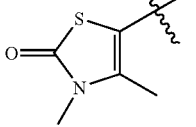 | 2.01 | A | |
| 624 | 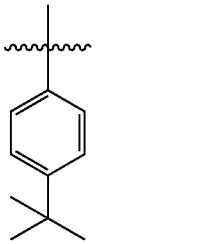 | 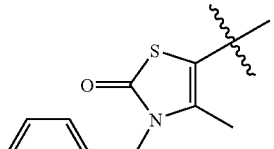 | 2.01 | A | |
| 625 | 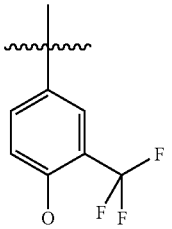 | 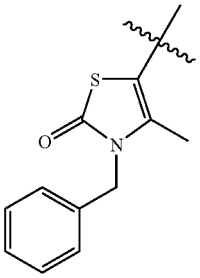 | 3.01 | A | |
| 626 | 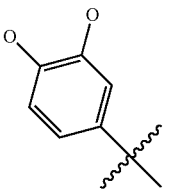 | 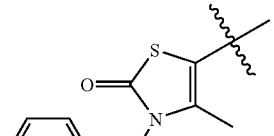 | 3.01 | A | |
| 627 | 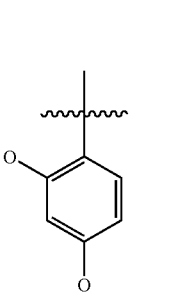 | | 4.03 | A | |

TABLE 1-continued
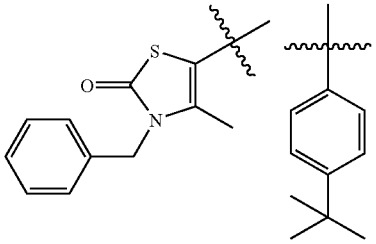
| N° | A | L | LogP | LogP method | M + 1 |
|----|---|---|------|-------------|-------|
| 628 | 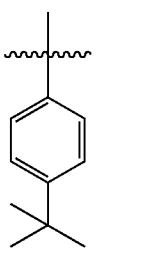 | 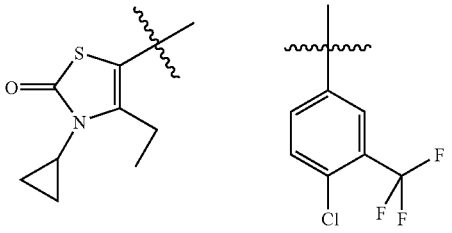 | 3.01 | A | |
| 629 | 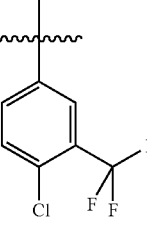 | 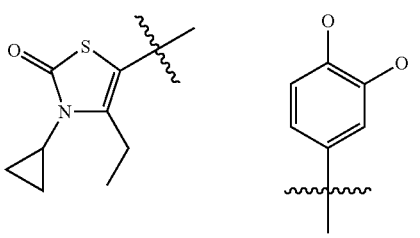 | 3.01 | A | |
| 630 | 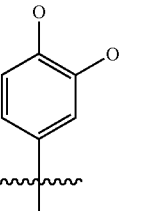 | 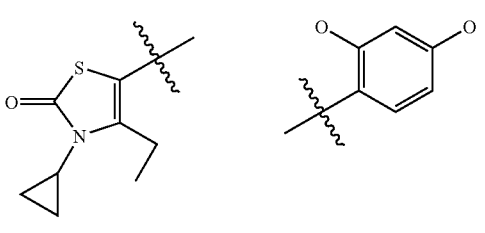 | 4.08 | A | |
| 631 | 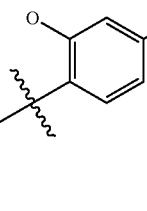 | 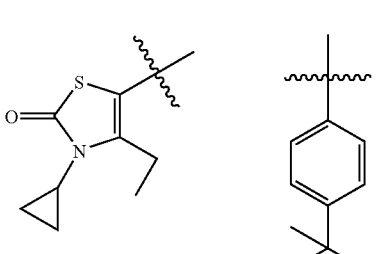 | 2.01 | A | |
| 632 | 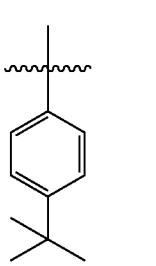 | | 3.01 | A | |

TABLE 1-continued
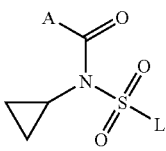
| N° | A | L | LogP | LogP method | M + 1 |
|---|---|---|---|---|---|
| 633 | | | 3.01 | A | |
| 634 | | | 3.01 | A | |
| 635 | | | 2.01 | A | |
| 636 | | | 3.01 | A | |
| 637 | | | 2.74 | A | |
| 638 | | | 3.1 | A | |

TABLE 1-continued

| N° | A | L | LogP | LogP method | M + 1 |
|---|---|---|---|---|---|
| 639 | 3-pyridyl | 3,4-dioxy-phenyl | 2.91 | A | |
| 640 | 2-chloro-6-methyl-pyridin-3-yl | 2-oxy-phenyl | | | 385 |
| 641 | 2-oxo-6-methyl-1,2-dihydropyridin-3-yl | 2,3-dioxy-phenyl | | | 418 |
| 642 | 3-pyridyl | 3-oxy-phenyl | 2.3 | A | |
| 643 | 2-chloropyridin-3-yl | 3-oxy-phenyl | 2.91 | A | |
| 644 | 2-chloropyridin-3-yl | 2-oxy-phenyl | 2.58 | A | |
| 645 | 2-oxo-1,2-dihydropyridin-3-yl | 2,3-dioxy-phenyl | 3.2 | B | |

TABLE 1-continued

| N° | A | L | LogP | LogP method | M + 1 |
|---|---|---|---|---|---|
| 646 | 3-(2-oxopyridinyl) with methyl | phenyl-4-O-phenyl | 3.7 | B | |
| 647 | 3-(2-oxopyridinyl) with methyl | 2,3-dioxyphenyl (methylenedioxy) | 3.7 | B | |
| 648 | 3-(2-oxopyridinyl) with methyl | phenyl-4-O-(4-bromophenyl) | 4.3 | B | |
| 649 | 2-fluoropyridin-3-yl | 2,3-(methylenedioxy)phenyl | 2.4 | B | |
| 650 | 4,6-dimethyl-2-oxopyridin-3-yl | 2,3-(methylenedioxy)phenyl | 3.57 | A | |
| 651 | 2-chloro-4,6-dimethylpyridin-3-yl | 2,3-(methylenedioxy)phenyl | 4.16 | A | |

TABLE 1-continued

| N° | A | L | LogP | LogP method | M + 1 |
|---|---|---|---|---|---|
| 652 | | | 2.78 | A | |
| 653 | | | 3.2 | A | |
| 654 | | | 2.93 | A | |
| 655 | | | | | 448 |
| 656 | | | | | 457 |
| 657 | | | | | 410 |
| 658 | | | 3.1 | B | |

TABLE 1-continued

| N° | A | L | LogP | LogP method | M + 1 |
|---|---|---|---|---|---|
| 659 | (1,4-dimethylpyrazol-5-yl) | 2,3,4-trioxyphenyl | 3.6 | B | |
| 660 | (1,4-dimethylpyrazol-5-yl) | 4-phenoxyphenyl | 3.6 | B | |
| 661 | (1,4-dimethylpyrazol-5-yl) | 4-(4-bromophenoxy)phenyl | 4.2 | B | |
| 662 | (4-iodo-1-methylpyrazol-5-yl) | 2,3-dioxyphenyl | 2.8 | B | |
| 663 | (4-iodo-1-methylpyrazol-5-yl) | 2,3,4-trioxyphenyl | 3.4 | B | |

TABLE 1-continued
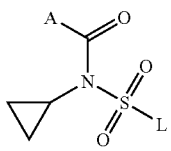
| N° | A | L | LogP | LogP method | M + 1 |
|---|---|---|---|---|---|
| 664 | 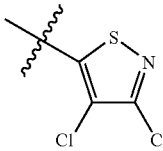 | 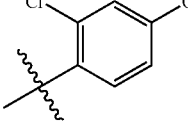 | | | 445 |
TABLE 2
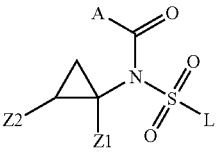
| | A | L | Z1 | Z2 | LogP | LogP method | M + 1 | M − 1 |
|---|---|---|---|---|---|---|---|---|
| 665 | 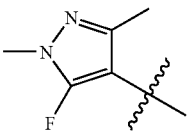 | 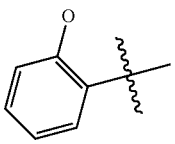 | 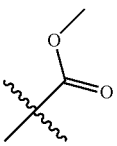 | 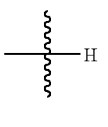 | | | 430 | |
| 666 | 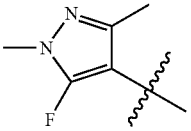 | 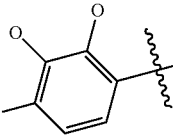 | 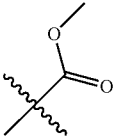 | 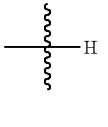 | | | | 496 |
| 667 | 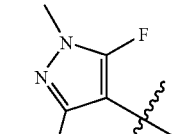 | 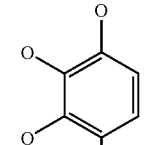 | 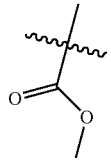 | 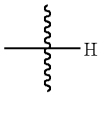 | 4.04 | B | | |
| 668 | 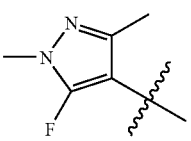 | 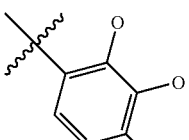 | 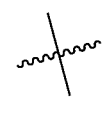 | 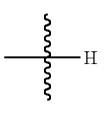 | | | 454 | |

TABLE 2-continued

| | A | L | Z1 | Z2 | LogP | LogP method | M + 1 | M − 1 |
|---|---|---|---|---|---|---|---|---|
| 669 | | | | H | 4.44 | A | | |
| 670 | | | | H | 4.1 | B | | |
| 671 | | | | H | | | 448 | |
| 672 | | | H | | | | 452 | |
| 673 | | | H | | | | 434 | |
| 674 | | | H | | | | 442 | |

TABLE 2-continued

| | | | | | LogP | | |
|---|---|---|---|---|---|---|---|
| A | L | Z1 | Z2 | LogP | method | M + 1 | M − 1 |
| 675 (ethoxy-methyl-pyrazole) | phenoxy-phenyl | —H | (cyclopropyl substituent) | | | 456 | |
| 676 (fluoro-methyl-pyrazole) | phenoxy | —H | phenyl | 3.27 | A | | |

The following examples illustrate in a non-limiting manner the preparation and efficacy of the compounds of formula (I) according to the invention.

PREPARATION EXAMPLE 1

N-[(4-bromophenyl)sulfonyl]-N-cyclopropyl-3-methoxy-1-methyl-1H-pyrazole-4-carboxamide (Compound 232)

Preparation of 4-bromo-N-cyclopropylbenzenesulfonamide

To a solution of 5.02 g (88.05 mmol) of cyclopropylamine in DCM (150 ml) at room temperature is added dropwise a solution of 7.50 g (29.35 mmol) of 4-bromobenzenesulfonyl chloride in DCM (20 ml).
After 1 hr the reaction mixture is poured over 100 mL of hydrochloric acid 1N and shaken. Organic phase is separated, dried over magnesium sulphate and solvent evaporated to give 7.27 g of desired product 4-bromo-N-cyclopropylbenzenesulfonamide as a white solid (85%).
RMN $^1$H (ppm) 0.1 (2H, m); 0.2 (2H, m), 1.85 (1H, m), 7.5 (2H, m), 7.62 (2H, m), 7.8 (1H, s)

Preparation of N-[(4-bromophenyl)sulfonyl]-N-cyclopropyl-3-methoxy-1-methyl-1H-pyrazole-4-carboxamide A solution of 1.64 g (5.96 mmol) of 4-bromo-N-cyclopropylbenzenesulfonamide and 7.69 g (6.86 mmol) of potassium terbutoxide is stirred in THF (35 ml) for 15 mins and 1.25 g (7.16 mmol) of 3 methoxy-1-methyl-1H-pyrazole-4-carbonyl chloride is added in one portion. 6 ml of DMF is added to solubilize the mixture and the reaction mixture is stirred for 45 mins at room temperature.
THF is removed under reduce pressure and the residue is partitioned between aqueous potassium carbonate and ethyl acetate. Organic phase is dried over magnesium sulphate and solvent evaporated. The white solid is washed with diethyl ether and dried to give 1.95 g of desired N-[(4-bromophenyl) sulfonyl]-N-cyclopropyl-3-methoxy-1-methyl-1H-pyrazole-4-carboxamide (76%).
Mass spectrum: [M+1]=414

PREPARATION EXAMPLE 2

N-cyclopropyl-3-methoxy-1-methyl-N-{[3'-(trimethylsilyl)biphenyl-4-yl]sulfonyl}-1H-pyrazole-4-carboxamide (Compound 233)

A suspension of 0.25 g (0.60 mmol) of N-[(4-bromophenyl)sulfonyl]-N-cyclopropyl-3-methoxy-1-methyl-1H-pyrazole-4-carboxamide (prepared in ex. 1), 0.17 g (0.90 mmol) of [3-(trimethylsilyl)phenyl]boronic acid and 0.014 g (0.012 mmol) of tetrakis(triphenyl-phosphine)palladium in a mixture of 20% aqueous potassium carbonate (15 ml) and THF (15 ml) are stirred at 80° C. for 2 hrs.
The reaction mixture is added to aqueous potassium carbonate and extracted into diethyl ether which is dried over magnesium sulphate and solvent evaporated. The crude material obtained is purified over a column of silica by using a diethyl ether as eluent, to give a colourless viscous oil. A 50:50 DiPE/heptane solution (10 ml) is added to this oil and allowed to evaporate over the W/E. Resultant crystalline material is washed with heptane, filtered off and dried to give 0.27 g of desired N-cyclopropyl-3-methoxy-1-methyl-N-([3'-(trimethylsilyl)biphenyl-4-yl]sulfonyl)-1H-pyrazole-4-carboxamide (91%)
Mass spectrum: [M+1]=484

PREPARATION EXAMPLE 3

N-cyclopropyl-3-methoxy-1-methyl-N-{[4-(phenylthio)phenyl]sulfonyl}-1H-pyrazole-4-carboxamide (Compound 266)

A suspension of 0.10 g (0.24 mmol) of N-[(4-bromophenyl)sulfonyl]N-cyclopropyl-3-methoxy-1-methyl-1H-pyrazole-4-carboxamide (prepared in ex 1), 0.026 g (0.24 mmol) of thiophenol, 0.0046 g (0.024 mmol) of copper iodide and 0.16 g (0.48 mmol) of cesium carbonate in N-methylpyrrolidone (2 ml) is heated under microwave irradiation at 140° C. for 5 mins.

The reaction mixture is purified over a column of silica by using a mixture of heptane and ethyl acetate as eluent to give 0.053 g of desired N-cyclopropyl-3-methoxy-1-methyl-N-{[4-(phenylthio)phenyl]sulfonyl}-1H-pyrazole-4-carboxamide (47%)

Mass spectrum: [M+1]=444

EFFICACY EXAMPLE A

In Vivo Test on *Alternaria Solani* (Tomato Leaf Spot)

| | |
|---|---|
| Solvent: | 49 parts by weight of N,N-dimethylformamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

Young plants are sprayed with the preparation of active compound at the stated rate of application. After the spray coating has dried on, the plants are inoculated with an aqueous spore suspension of *Alternaria solani*. The plants remain for one day in an incubation cabinet at approximately 20° C. and a relative atmospheric humidity of 100%. Then the plants are placed in an incubation cabinet at approximately 20° C. and a relative atmospheric humidity of 96%.

The test is evaluated 7 days after the inoculation. Under these conditions, good (at least 70%) to total protection is observed at a dose of 500 ppm with the following compounds 110, 143, 160, 175, 176, 178, 179, 180, 186, 187, 189, 192, 196, 198, 203, 204, 205, 209, 210, 212, 214, 215 and 652.

EFFICACY EXAMPLE B

In Vivo Test on *Podosphaera leucotncha* (Apple Mildew)

| | |
|---|---|
| Solvent: | 24.5 parts by weight of acetone |
| | 24.5 parts by weight of dimethylacetamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

Young plants are sprayed with the preparation of active compound at the stated rate of application. After the spray coating has dried on, the plants are inoculated with an aqueous spore suspension of the causal agent of apple mildew (*Podosphaera leucobicha*). The plants are then placed in a greenhouse at approximately 23° C. and a relative atmospheric humidity of approximately 70%.

The test is evaluated 10 days after the inoculation. Under these conditions, good (at least 70%) to total protection is observed at a dose of 100 ppm with the following compounds: 104, 160, 176, 177, 180, 186, 187, 188, 192, 194, 196, 198, 203, 204, 205, 207, 209, 210, 211, 212, 213, 218 and 446.

EFFICACY EXAMPLE C

In Vivo Test on *Erysiphe Graminis* (Barley Mildew)

| | |
|---|---|
| Solvent: | 50 parts by weight of N,N-dimethylacetamid |
| Emulsifier: | 1.0 part by weight of alkylaryl polyglycol ether |

To produce a suitable preparation of active compound, 1 part by weight of active compound or active compound combination is mixed with the stated amounts of solvent and emulsifier, and the concentrate is diluted with water to the desired concentration.

Young plants are sprayed with the preparation of active compound or active compound combination at the stated rate of application. After the spray coating has dried on, the plants are dusted with spores of *Erysiphe graminis* f.sp. horde. The plants are placed in a greenhouse at a temperature of approximately 20° C. and a relative atmospheric humidity of approximately 80% to promote the development of mildew pustules.

The test is evaluated 7 days after the inoculation. Under these conditions, good (at least 70%) to total protection is observed at a dose of 1000 ppm with the following compounds: 104, 160, 177, 178, 186, 192, 194, 203, 204, 205, 207, 210, 212, 213 and 435.

EFFICACY EXAMPLE D

In Vivo Test on *Pyrenophore teres* (Barley Net Blotch)

The active ingredients tested are prepared by homogenisation in a mixture of acetone/tween/DMSO, then diluted with water to obtain the desired active material concentration. Barley plants (Express variety) in starter cups, sown on a 50/50 peat soil-pozzolana substrate and grown at 12° C., are treated at the 1-leaf stage (10 cm tall) by spraying with the active ingredient prepared as described above. Plants, used as controls, are treated with the mixture of acetone/tween/DMSO/water not containing the active material.

After 24 hours, the plants are contaminated by spraying them with an aqueous suspension of *Pyrenophora teres* spores (12,000 spores per ml). The spores are collected from a 12-day-old culture. The contaminated barley plants are incubated for 24 hours at about 20° C. and at 100% relative humidity, and then for 12 days at 80% relative humidity.

Grading is carried out 12 days after the contamination, in comparison with the control plants. Under these conditions, good (at least 70%) or total protection is observed at a dose of 500 ppm with the following compounds: 104, 160, 180, 210, 244, 254, 255, 258, 262, 263, 266, 267, 268, 269, 270, 272, 274, 311, 357, 374, 375, 381, 387, 393, 396, 398, 436, 456, 492, 501, 516, 517, 531, 542, 546 and 673

EXAMPLE E

In vivo Test on *Mycosphaerella graminicola* (Wheat Leaf Spot)

The active ingredients tested are prepared by homogenisation in a mixture of acetone/tween/DMSO, and then diluted with water to obtain the desired active material concentration.

Wheat plants (Scipion variety), sown on a 50/50 peat soil-pozzolana substrate in starter cups and grown at 12° C., are treated at the 1-leaf stage (10 cm tall) by spraying with the active ingredient prepared as described above.

Plants, used as controls, are treated with the mixture of acetone/tween/DMSO/water not containing the active material.

After 24 hours, the plants are contaminated by spraying them with an aqueous suspension of *Mycosphaerella graminicola* spores (500 000 spores per ml). The spores are collected from a 7-day-old culture. The contaminated wheat plants are incubated for 72 hours at 18° C. and at 100% relative humidity, and then for 21 to 28 days at 90% relative humidity.

Grading (% of efficacy) is carried out 21 to 28 days after the contamination, in comparison with the control plants.

Under these conditions, good (at least 70%) or total protection is observed at a dose of 500 ppm with the following compounds: 45, 49, 244, 249, 254, 255, 258, 262, 263, 264, 311, 316, 358, 374, 375, 377, 387, 392, 394, 398, 438, 456, 457, 488, 492, 493, 494, 495, 496, 497, 498, 499, 500, 501, 502, 504, 505, 506, 507, 508, 509, 510, 511, 512, 514, 515, 516, 517, 518, 519, 521, 522, 523, 524, 528, 530, 531, 535, 538, 539, 542, 547, 550, 552, 556, 559, 578, 579, 583, 584, 585, 673 and 675.

EFFICACY EXAMPLE F

In vivo Test on *Puccinia reconditef.* Sp. *tritici* (Wheat Brown Rust)

The active ingredients tested are prepared by homogenisation in a mixture of acetone/tween/DMSO, then diluted with water to obtain the desired active material concentration. Wheat plants (Scipion variety) in starter cups, sown on 50/50 peat soil-pozzolana substrate and grown at 12° C., are treated at the 1-leaf stage (10 cm tall) by spraying with the active ingredient prepared as described above. Plants, used as controls, are treated with the mixture of acetone/tween/DMSO/water not containing the active material.

After 24 hours, the plants are contaminated by spraying the leaves with an aqueous suspension of *Puccinia recondita* spores (100,000 spores per ml). The spores are collected from a 10-day-old contaminated wheat and are suspended in water containing 2.5 ml/of tween 80 10%. The contaminated wheat plants are incubated for 24 hours at 20° C. and at 100% relative humidity, and then for 10 days at 20° C. and at 70% relative humidity. Grading is carried out 10 days after the contamination, in comparison with the control plants.

Under these conditions, good (at least 70%) or total protection is observed at a dose of 500 ppm with the following compounds: 49, 104, 160, 262, 264, 266, 269, 270, 272, 279, 281, 308, 309, 316, 318, 320, 328, 336, 337, 344, 366, 380, 398, 448, 456, 457, 493, 495, 498, 502, 507, 513, 514, 515, 524, 528, 531, 533, 539, 542, 545, 546, 547, 548, 550, 551, 552, 554, 555, 556, 557, 558 and 559.

The invention claimed is:
1. A compound of formula (I)

(I)

wherein
A is a carbon linked, substituted or non substituted, 5-membered, aromatic or non aromatic, fused or non fused heterocycle comprising two nitrogen atoms;
E is a substituted or non substituted cyclopropyl;
L is
(A) a substituted or non substituted phenyl or
(B) a substituted or non substituted 5-, 6- or 7-membered aromatic or non aromatic heterocycle comprising up to three heteroatoms which can be the same or different, optionally fused to a substituted or non substituted phenyl ring;
provided that when E is a non-substituted cyclopropyl, A and L cannot be simultaneously respectively a 2-bromo-4-methyl-1,3-thiazol-5-yl and a 4-chloro-phenyl; a 2-chloro-4-methyl-1,3-thiazol-5-yl and a 4-chloro-phenyl; a 2-bromo-4-ethyl-1,3-thiazol-5-yl and a 4-chloro-phenyl; a 2-chloro-4-ethyl-1,3-thiazol-5-yl and a 4-chloro-phenyl; a 2-bromo-4-methyl-1,3-thiazol-5-yl and a phenyl; a 2-chloro-4-methyl-1,3-thiazol-5-yl and a phenyl; a 2-bromo-4-ethyl-1,3-thiazol-5-yl and a phenyl; a 2-chloro-4-ethyl-1,3-thiazol-5-yl and a phenyl.

2. The compound of claim 1 wherein E can be substituted by up to five groups Z which can be the same or different and are selected from the group consisting of halogen atoms; $C_1$-$C_5$-alkyl; $C_1$-$C_5$-halogenoalkyl comprising up to 5 halogen atoms which can be the same or different; phenyl substituted by up to 5 halogen atoms which can be the same or different; and $C_1$-$C_5$-alkoxycarbonyl.

3. The compound of claim 1 wherein E is a non-substituted cyclopropyl.

4. The compound of claim 1 wherein A is substituted by up to three groups R which can be the same or different and are selected from the group consisting of halogen atoms; cyano; nitro; hydroxy; amino; sulfanyl; pentafluoro-$\lambda^6$-sulfanyl; formyl; formyloxy; formylamino; carboxy; carbamoyl; N-hydroxycarbamoyl; carbamate; (hydroxyimino)-$C_1$-$C_6$-alkyl; $C_1$-$C_5$-alkylamino; di-$C_1$-$C_5$-alkylamino; tri($C_1$-$C_5$-alkyl)silyl; $C_1$-$C_5$-alkylsulfanyl; $C_1$-$C_5$-halogenoalkylsulfanyl comprising up to 5 halogen atoms which can be the same or different; $C_1$-$C_5$-alkyl; $C_1$-$C_5$-halogenoalkyl comprising up to 5 halogen atoms which can be the same or different; $C_2$-$C_5$-alkenyl; $C_2$-$C_5$-halogenoalkenyl comprising up to 5 halogen atoms which can be the same or different; $C_2$-$C_5$-alkynyl; $C_2$-$C_5$-halogenoalkynyl comprising up to 5 halogen atoms which can be the same or different; $C_1$-$C_5$-alkoxy; $C_1$-$C_5$-halogenoalkoxy comprising up to 5 halogen atoms which can be the same or different; $C_2$-$C_5$-alkenyloxy; $C_2$-$C_5$-halogenoalkenyloxy comprising up to 5 halogen atoms which can be the same or different; $C_2$-$C_5$-alkynyloxy; $C_2$-$C_5$-halogenoalkynyloxy comprising up to 5 halogen atoms which can be the same or different; $C_3$-$C_7$-cycloalkyl; $C_3$-$C_7$-halogenocycloalkyl comprising up to 5 halogen atoms which can be the same or different; $C_1$-$C_5$-alkylcarbonyl; $C_1$-$C_5$-halogenoalkylcarbonyl comprising up to 5 halogen atoms which can be the same or different; $C_1$-$C_5$-alkylcarbamoyl; di-$C_1$-$C_5$-alkylcarbamoyl; N—$C_1$-$C_5$-alkyloxycarbamoyl; $C_1$-$C_5$-alkoxycarbamoyl; N—$C_1$-$C_5$-alkyl-$C_1$-$C_5$-alkoxycarbamoyl; $C_1$-$C_5$-alkoxycarbonyl; $C_1$-$C_5$-halogenoalkoxycarbonyl comprising up to 5 halogen atoms which can be the same or different; $C_1$-$C_5$-alkylcarbonyloxy; $C_1$-$C_5$-halogenoalkylcarbonyloxy comprising up to 5 halogen atoms which can be the same or different; $C_1$-$C_5$-alkylcarbonylamino; $C_1$-$C_5$-halogenoalkylcarbonylamino comprising up to 5 halogen atoms which can be the same or different; $C_1$-$C_5$-alkylaminocarbonyloxy; di-$C_1$-$C_5$-alkylaminocarbonyloxy; $C_1$-$C_5$-alkyloxycarbonyloxy; $C_1$-$C_5$-alkylsulfenyl; $C_1$-$C_5$-halogenoalkylsulfenyl comprising up to 5 halogen atoms which can be the same or different; $C_1$-$C_5$-alkylsulfinyl; $C_1$-$C_5$-halogenoalkylsulfinyl comprising up to 5 halogen atoms which can be the same or different; $C_1$-$C_5$-alkylsulfonyl; $C_1$-$C_5$-halogenoalkylsulfonyl comprising up to 5 halogen atoms which can be the same or different; $C_1$-$C_5$ alkoxyimino; ($C_1$-$C_5$-alkoxyimino)-$C_1$-$C_5$-alkyl; ($C_1$-$C_5$-alkenyloxyimino)-$C_1$-$C_5$-alkyl; ($C_1$-$C_5$-alkynyloxyimino)-$C_1$-$C_5$-alkyl; a (benzyloxyimino)-$C_1$-$C_5$-alkyl; benzyloxy; benzylsulfanyl; benzylamino; naphthyl; halogenophenyl comprising up to 5 halogen atoms which can be the same or different; and halogenophenoxy comprising up to 5 halogen atoms which can be the same or different.

5. The compound of claim 1 wherein A is substituted by up to three groups R independently selected from the group consisting of a halogen atom; cyano; $C_1$-$C_5$-alkyl; $C_1$-$C_5$-alkoxy; $C_2$-$C_5$-alkenyloxy; $C_2$-$C_5$-alkynyloxy; $C_3$-$C_5$-cycloalkyl; $C_1$-$C_5$-alkoxycarbonyl; $C_1$-$C_5$-alkylsulfanyl; $C_1$-$C_5$-alkylamino; di($C_1$-$C_5$-alkyl)amino; phenyl; phenoxy; benzyl; $C_1$-$C_5$-halogenoalkyl comprising up to 5 halogen atoms which can be the same or different; $C_1$-$C_5$-halogenocycloalkyl comprising up to 5 halogen atoms which can be the same or different; $C_1$-$C_5$-halogenoalkoxy comprising up to 5 halogen atoms which can be the same or different; halogenophenyl comprising up to 5 halogen atoms which can be the same or different and halogenophenoxy comprising up to 5 halogen atoms which can be the same or different.

6. The compound of claim 1 wherein A is selected from the group consisting of:

a heterocycle of formula ($A^{12}$)

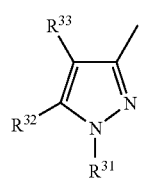

($A^{12}$)

wherein:
  $R^{31}$ is selected from the group consisting of a $C_1$-$C_5$-alkyl and a phenyl;
  $R^{32}$ is selected from the group consisting of a hydrogen atom, a halogen atom, a $C_1$-$C_5$-alkyl and a $C_1$-$C_5$-halogenoalkyl comprising up to 5 halogen atoms which can be the same or different;
  $R^{33}$ is selected from the group consisting of a hydrogen atom, a halogen atom, a nitro and a $C_1$-$C_5$-halogenoalkyl comprising up to 5 halogen atoms which can be the same or different;

a heterocycle of formula ($A^{13}$)

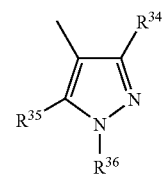

($A^{13}$)

wherein:
  $R^{34}$ is selected from the group consisting of a hydrogen atom, a halogen atom, a $C_1$-$C_5$-alkyl, a C3-$C_5$-cycloalkyl, a $C_1$-$C_5$-halogenoalkyl comprising up to halogen atoms which can be the same or different, a $C_1$-$C_5$-alkoxy, a $C_2$-$C_5$-alkynyloxy and a phenyl;
  $R^{35}$ is selected from the group consisting of a hydrogen atom, a halogen atom, a $C_1$-$C_5$-alkyl, a cyano, a $C_1$-$C_5$-alkoxy, a $C_1$-$C_5$-alkylthio, a $C_1$-$C_5$-halogenoalkyl comprising up to 5 halogen atoms which can be the same or different, a $C_1$-$C_5$-alkylamino, a di($C_1$-$C_5$-alkyl)amino and a halogenophenoxy comprising up to 5 halogen atoms which can be the same or different;
  $R^{36}$ is selected from the group consisting of a hydrogen atom, a C-$C_5$-alkyl and a phenyl;

a heterocycle of formula ($A^{14}$)

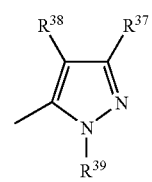

($A^{14}$)

wherein:
  $R^{37}$ and $R^{38}$ which can be the same or different represent a hydrogen atom, a halogen atom and a $C_1$-$C_5$-alkyl;
  $R^{39}$ is a $C_1$-$C_5$-alkyl;

a heterocycle of formula ($A^{19}$)

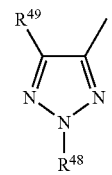

($A^{19}$)

wherein:
  $R^{48}$ is selected from the group consisting of a hydrogen atom and a halogenophenyl comprising up to 5 halogen atoms which can be the same or different;
  $R^{49}$ is selected from the group consisting of a hydrogen atom, a halogen atom and a $C_1$-$C_5$-alkyl;

a heterocycle of formula (A²⁰)

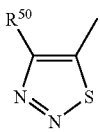

(A²⁰)

wherein
R⁵⁰ is selected from the group consisting of a hydrogen atom and a $C_1$-$C_5$-alkyl;
a heterocycle of formula (A²¹)

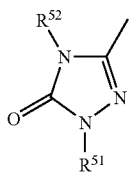

(A²¹)

wherein:
R⁵¹ and R⁵² are independently selected from the group consisting of a $C_1$-$C_5$-alkyl.

7. The compound of claim 1 wherein A is a fused heterocycle.

8. The compound of claim 7 wherein A is selected from the group consisting of:
a heterocycle of formula (A²⁹)

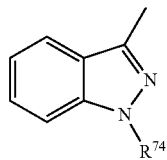

(A²⁹)

wherein:
R⁷⁴ is a $C_1$-$C_5$-alkyl; and
a heterocycle of formula (A³⁰)

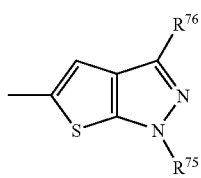

(A³⁰)

wherein:
R⁷⁵ and R⁷⁶ which can be the same or different are each a $C_1$-$C_5$-alkyl.

9. The compound of claim 1 wherein L is a phenyl substituted by up to five groups X independently selected from the group consisting of halogen atoms; cyano; nitro; hydroxy; amino; sulfanyl; pentafluoro-λ⁶-sulfanyl; formyl; formyloxy; formylamino; carboxy; carbamoyl; N-hydroxycarbamoyl; carbamate; (hydroxyimino)-$C_1$-$C_6$-alkyl; $C_1$-$C_5$-alkylamino; di-$C_1$-$C_5$-alkylamino; tri($C_1$-$C_5$-alkyl)silyl; $C_1$-$C_5$-alkylsulfanyl; $C_1$-$C_5$-halogenoalkylsulfanyl comprising up to 5 halogen atoms which can be the same or different; $C_1$-$C_5$-alkyl; $C_1$-$C_5$-halogenoalkyl comprising up to 5 halogen atoms which can be the same or different; $C_2$-$C_5$-alkenyl; $C_2$-$C_5$-halogenoalkenyl comprising up to 5 halogen atoms which can be the same or different; $C_2$-$C_5$-alkynyl; $C_2$-$C_5$-halogenoalkynyl comprising up to 5 halogen atoms which can be the same or different; $C_1$-$C_5$-alkoxy; $C_1$-$C_5$-halogenoalkoxy comprising up to 5 halogen atoms which can be the same or different; $C_2$-$C_5$-alkenyloxy; $C_2$-$C_5$-halogenoalkenyloxy comprising up to 5 halogen atoms which can be the same or different; $C_2$-$C_5$-alkynyloxy; $C_2$-$C_5$-halogenoalkynyloxy comprising up to 5 halogen atoms which can be the same or different; $C_3$-$C_7$-cycloalkyl; $C_3$-$C_7$-halogenocycloalkyl comprising up to 5 halogen atoms which can be the same or different; $C_1$-$C_5$-alkylcarbonyl; $C_1$-$C_5$-halogenoalkylcarbonyl comprising up to 5 halogen atoms which can be the same or different; $C_1$-$C_5$-alkylcarbamoyl; di-$C_1$-$C_5$-alkylcarbamoyl; N—$C_1$-$C_5$-alkyloxycarbamoyl; $C_1$-$C_5$-alkoxycarbamoyl; N—$C_1$-$C_5$-alkyl-$C_1$-$C_5$-alkoxycarbamoyl; $C_1$-$C_5$-alkoxycarbonyl; $C_1$-$C_5$-halogenoalkoxycarbonyl comprising up to 5 halogen atoms which can be the same or different; $C_1$-$C_5$-alkylcarbonyloxy; $C_1$-$C_5$-halogenoalkylcarbonyloxy comprising up to 5 halogen atoms which can be the same or different; $C_1$-$C_5$-alkylcarbonylamino; $C_1$-$C_5$-halogenoalkylcarbonylamino comprising up to 5 halogen atoms which can be the same or different; $C_1$-$C_5$-alkylaminocarbonyloxy; di-$C_1$-$C_5$-alkylaminocarbonyloxy; $C_1$-$C_5$-alkyloxycarbonyloxy, $C_1$-$C_5$-alkylsulphenyl, $C_1$-$C_5$-halogenoalkylsulphenyl comprising up to 5 halogen atoms which can be the same or different, $C_1$-$C_5$-alkylsulphinyl, $C_1$-$C_5$-halogenoalkylsulphinyl comprising up to 5 halogen atoms which can be the same or different, $C_1$-$C_5$-alkylsulphonyl, $C_1$-$C_5$-halogenoalkylsulphonyl comprising up to 5 halogen atoms which can be the same or different, $C_1$-$C_6$-alkoxyimino, ($C_1$-$C_6$-alkoxyimino)-$C_1$-$C_6$-alkyl, ($C_1$-$C_6$-alkenyloxyimino)-$C_1$-$C_6$-alkyl, ($C_1$-$C_6$-alkynyloxyimino)-$C_1$-$C_6$-alkyl, a (benzyloxyimino)-$C_1$-$C_6$-alkyl, benzylsulfanyl, benzylamino, naphthyl; phenyl which can be substituted by up to five groups Q which can be the same or different; phenoxy which can be substituted by up to five groups Q which can be the same or different; benzyloxy which can be substituted by up to five groups Q which can be the same or different; phenylamino which can be substituted by up to five groups Q which can be the same or different, phenylsulfanyl which can be substituted by up to five groups Q which can be the same or different; phenylmethylene which can be substituted by up to five groups Q which can be the same or different; pyridinyl which can be substituted by up to four groups Q which can be the same or different and pyridinyloxy which can be substituted by up to four groups Q which can be the same or different; wherein Q is selected from the group consisting of halogen atoms; cyano; nitro; $C_1$-$C_5$-alkyl; $C_1$-$C_5$-alkylamino; di-$C_1$-$C_5$-alkylamino; $C_1$-$C_5$-alkoxy; $C_1$-$C_5$-alkylsulfanyl; benzyloxy; $C_1$-$C_5$-halogenoalkyl comprising 1 to 5 halogen atoms which can be the same or different; $C_1$-$C_5$-halogenoalkoxy comprising 1 to 5 halogen atoms which can be the same or different and tri($C_1$-$C_5$)alkylsilyl.

10. The compound of claim 9 wherein L is a phenyl substituted by up to five groups X independently selected from the group consisting of halogen atoms; cyano; nitro; $C_1$-$C_5$-alkyl; $C_2$-$C_5$-alkenyl; $C_2$-$C_5$-alkynyl; $C_1$-$C_5$-halogenoalkyl comprising up to 5 halogen atoms which can be the same or different; $C_1$-$C_5$-alkoxy; $C_2$-$C_5$-alkenyloxy; $C_2$-$C_5$-alkynyloxy; $C_1$-$C_5$-halogenoalkoxy comprising up to 5 halogen atoms which can be the same or different; tri($C_1$-$C_5$-alkyl)silyl; naphthyl; phenyl which can be substituted by up to five groups Q which can be the same or different; phenoxy which can be substituted by up to five groups Q which can be the same or different; phenylsulfanyl which can be substituted by up to five groups Q which can be the same or different; phenylmethylene which can be substituted by up to five groups Q which can be the same or different; pyridinyl which can be substituted by up to four groups Q which can be the same or different and pyridinyloxy which can be substituted by up to four groups Q which can be the same or different.

11. The compound of claim 1 wherein L is a 5-, 6- or 7-membered aromatic or non aromatic heterocycle substituted by up to five groups X independently selected from the group consisting of halogen atoms; cyano; nitro; $C_1$-$C_5$-alkyl; $C_2$-$C_5$-alkenyl; $C_2$-$C_5$-alkynyl; $C_1$-$C_5$-halogenoalkyl comprising up to 5 halogen atoms which can be the same or different; $C_1$-$C_5$-alkoxy; $C_2$-$C_5$-alkenyloxy; $C_2$-$C_5$-alkynyloxy; $C_1$-$C_5$-halogenoalkoxy comprising up to 5 halogen atoms which can be the same or different; tri($C_1$-$C_5$-alkyl)silyl; phenyl which can be substituted by up to five groups Q which can be the same or different and phenoxy which can be substituted by up to five groups Q which can be the same or different; phenylsulfanyl which can be substituted by up to five groups Q which can be the same or different; wherein Q is selected from the group consisting of halogen atoms; cyano; nitro; $C_1$-$C_5$-alkyl; $C_1$-$C_5$-alkylamino; di-$C_1$-$C_5$-alkylamino; $C_1$-$C_5$-alkoxy; $C_1$-$C_5$-alkylsulfanyl; benzyloxy; $C_1$-$C_5$-halogenoalkyl comprising 1 to 5 halogen atoms which can be the same or different; $C_1$-$C_5$-halogenoalkoxy comprising 1 to 5 halogen atoms which can be the same or different and tri($C_1$-$C_5$)alkylsilyl.

12. The compound of claim 11 wherein L is a five membered heterocycle.

13. The compound of claim 12 wherein L is selected from the group consisting of
a heterocycle of formula ($L^{40}$):

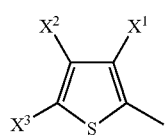

($L^1$)

wherein:
$X^1$ to $X^3$ are independently selected from the group consisting of a hydrogen atom; a halogen atom; and a $C_1$-$C_5$-alkyl;
a heterocycle of formula ($L^2$)

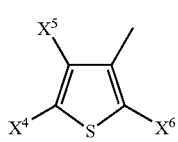

($L^2$)

wherein:
$X^4$ is selected from the group consisting of a hydrogen atom; a halogen atom; a $C_1$-$C_5$-alkyl; and a $C_1$-$C_5$-alkyloxycarbonyl;
$X^5$ is selected from the group consisting of a hydrogen atom and a halogen atom; and
$X^6$ is selected from the group consisting of a hydrogen atom; a halogen atom; and a $C_1$-$C_5$-alkyl;

a heterocycle of formula ($L^3$)

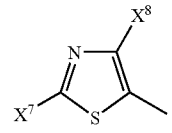

($L^3$)

wherein:
$X^7$ is selected from the group consisting of a hydrogen atom; a halogen atom; and a $C_1$-$C_5$-alkyl; and
$X^8$ is selected from the group consisting of a hydrogen atom and a $C_1$-$C_5$-alkyl; and
a heterocycle of formula ($L^4$)

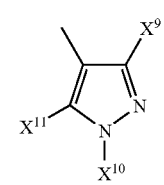

($L^4$)

wherein
$X^9$ is selected from the group consisting of a $C_1$-$C_5$-alkyl and a $C_1$-$C_5$-halogenoalkyl comprising up to 5 halogen atoms which can be the same or different;
$X^{10}$ is selected from the group consisting of a $C_1$-$C_5$-alkyl and a phenyl; and
$X^{11}$ is selected from the group consisting of a hydrogen atom; a halogen atom; and a $C_1$-$C_5$-alkyl.

14. The compound of claim 11 wherein L is a six membered heterocycle.

15. The compound of claim 14 wherein L is selected from the group consisting of
a heterocycle of formula ($L^5$)

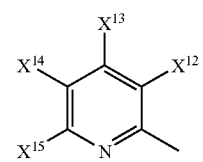

($L^5$)

wherein:
$X^{12}$, $X^{13}$ $X^{15}$ are independently selected from the group consisting of a hydrogen atom and a halogen atom; and
$X^{14}$ is selected from the group consisting of a hydrogen atom, a halogen atom and a $C_1$-$C_5$-halogenoalkyl comprising up to 5 halogen atoms which can be the same or different; and a heterocycle of formula (L⁶)

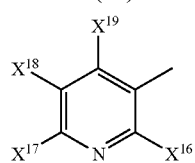
(L⁶)

wherein:
$X^{16}$ to $X^{19}$ are independently selected from the group consisting of a hydrogen atom, a halogen atom and a $C_1$-$C_5$-alkyl.

16. The compound of claim 1 wherein L is a fused heterocycle.

17. The compound of claim 16 wherein L is selected from the group consisting of
a heterocycle of formula (L⁷)

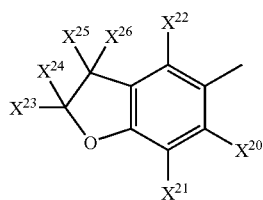
(L⁷)

wherein:
$X^{20}$ to $X^{22}$ are independently selected from the group consisting of a hydrogen atom, a halogen atom and a $C_1$-$C_5$ alkyl; and
$X^{23}$ to $X^{26}$ are independently selected from the group consisting of a hydrogen atom and a $C_1$-$C_5$ alkyl;
a heterocycle of formula (L⁸)

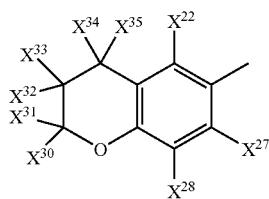
(L⁸)

wherein:
$X^{27}$ to $X^{29}$ are independently selected from the group consisting of a hydrogen atom, a halogen atom and a $C_1$-$C_5$ alkyl; and
$X^{30}$ to $X^{35}$ are independently selected from the group consisting of a hydrogen atom and a $C_1$-$C_5$ alkyl;
a heterocycle of formula (L⁹)

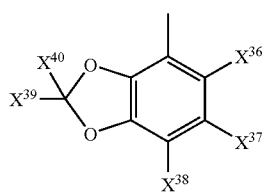
(L⁹)

wherein:
$X^{36}$ to $X^{38}$ are independently selected from the group consisting of a hydrogen atom, a halogen atom and a $C_1$-$C_5$ alkyl; and
$X^{39}$ and $X^{40}$ are independently selected from the group consisting of a hydrogen atom, a halogen atom and a $C_1$-$C_5$ alkyl; and
a heterocycle of formula (L¹⁰)

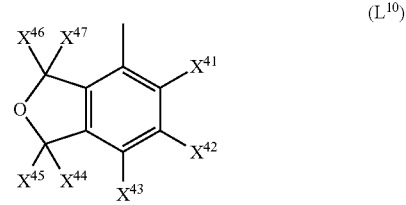
(L¹⁰)

wherein:
$X^{41}$ to $X^{43}$ are independently selected from the group consisting of a hydrogen atom, a halogen atom and a $C_1$-$C_5$ alkyl; and
$X^{44}$ to $X^{47}$ are independently selected from the group consisting of a hydrogen atom and a $C_1$-$C_5$ alkyl.

18. A method for controlling phytopathogenic fungi of plants or crops comprising applying a compound of formula (I) of claim 1 to the seed, the plant or to the fruit of the plant or to the soil wherein the plant is growing or wherein it is desired to grow.

19. The compound of claim 6 wherein A is a heterocycle of formula (A¹³)
wherein:
$R^{34}$ is a $C_1$-$C_5$-alkyl;
$R^{35}$ is a fluorine atom;
$R^{36}$ is a $C_1$-$C_5$-alkyl; or
wherein
$R^{34}$ is a $C_1$-$C_5$-halogenoalkyl comprising up to 5 halogen atoms;
$R^{35}$ is a hydrogen or fluorine atom;
$R^{36}$ is a $C_1$-$C_5$-alkyl; or
wherein:
$R^{34}$ represents is a $C_1$-$C_5$-alkoxy;
$R^{35}$ is hydrogen;
$R^{36}$ is a $C_1$-$C_5$-alkyl.

20. A compound of the formula

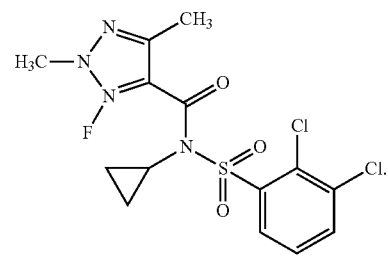

21. A method for controlling phytopathogenic fungi of plants or crops comprising applying the compound of claim 20 to the seed, the plant or to the fruit of the plant or to the soil wherein the plant is growing or wherein it is desired to grow.

* * * * *